US012629064B2

(12) United States Patent
Boo et al.

(10) Patent No.: US 12,629,064 B2
(45) Date of Patent: May 19, 2026

(54) GLUCOSE-SENSING DEVICE WITH MALTOSE BLOCKING LAYER

(71) Applicant: UXN CO., LTD, Suwon-si (KR)

(72) Inventors: Hankil Boo, Suwon-si (KR); Joungmin Lee, Suwon-si (KR); Rae Kyu Chang, Suwon-si (KR)

(73) Assignee: UXN Co., Ltd., Suwon-si (KR)

( * ) Notice: Subject to any disclaimer, the term of this patent is extended or adjusted under 35 U.S.C. 154(b) by 1066 days.

(21) Appl. No.: 17/493,467

(22) Filed: Oct. 4, 2021

(65) Prior Publication Data

US 2022/0031210 A1 Feb. 3, 2022

Related U.S. Application Data

(63) Continuation of application No. 16/167,298, filed on Oct. 22, 2018, now Pat. No. 11,134,873, which is a
(Continued)

(51) Int. Cl.
*A61B 5/145* (2006.01)
*A61B 5/00* (2006.01)
(Continued)

(52) U.S. Cl.
CPC ........ *A61B 5/14865* (2013.01); *A61B 5/0031* (2013.01); *A61B 5/14532* (2013.01);
(Continued)

(58) Field of Classification Search
CPC .............. A61B 5/14865; A61B 5/0031; A61B 5/14532; A61B 5/1473; A61B 5/72;
(Continued)

(56) References Cited

U.S. PATENT DOCUMENTS

| | | | |
|---|---|---|---|
| 3,869,354 A | 3/1975 | Montalvo, Jr. | |
| 7,236,812 B1 | 6/2007 | Ballerstadt et al. | |
| | (Continued) | | |

FOREIGN PATENT DOCUMENTS

| | | | |
|---|---|---|---|
| CN | 101298682 A | 11/2008 | |
| CN | 101303325 A | 11/2008 | |
| | (Continued) | | |

OTHER PUBLICATIONS

Attard et al., "Liquid-Crystalline Phases as Templates for the Synthesis of Mesoporous Silica", Nature (1995), vol. 378, No. 23, pp. 366-368.

(Continued)

*Primary Examiner* — Jacqueline Cheng
*Assistant Examiner* — Tho Q Tran
(74) *Attorney, Agent, or Firm* — K&L Gates LLP

(57) ABSTRACT

This disclosure relates to a glucose-sensing electrode including a nanoporous metal layer and a maltose-blocking layer formed over the nanoporous metal layer. The nanoporous metal layer is capable of oxidizing both glucose and maltose without an enzyme specific to glucose or maltose in the glucose-sensing electrode. The maltose-blocking layer has porosity that permits glucose to pass therethrough and inhibits maltose from passing therethrough toward the nanoporous metal layer.

31 Claims, 49 Drawing Sheets
(8 of 49 Drawing Sheet(s) Filed in Color)

Related U.S. Application Data continuation of application No. 15/844,515, filed on Dec. 15, 2017, now Pat. No. 10,107,776.

(60) Provisional application No. 62/599,631, filed on Dec. 15, 2017, provisional application No. 62/589,513, filed on Nov. 21, 2017.

(51) Int. Cl.

| | |
|---|---|
| *A61B 5/1473* | (2006.01) |
| *A61B 5/1486* | (2006.01) |
| *B01J 13/00* | (2006.01) |
| *B05D 5/00* | (2006.01) |
| *B05D 5/02* | (2006.01) |
| *B82Y 15/00* | (2011.01) |
| *B82Y 30/00* | (2011.01) |
| *B82Y 40/00* | (2011.01) |
| *C09D 5/02* | (2006.01) |
| *C09D 5/24* | (2006.01) |
| *C09D 7/40* | (2018.01) |
| *C12Q 1/00* | (2006.01) |
| *G01N 27/327* | (2006.01) |
| *G01N 27/333* | (2006.01) |
| *G01N 27/416* | (2006.01) |
| *G01N 33/49* | (2006.01) |
| *G01N 33/66* | (2006.01) |

(52) U.S. Cl.
CPC .............. *A61B 5/1473* (2013.01); *A61B 5/72* (2013.01); *A61B 5/742* (2013.01); *B01J 13/0013* (2013.01); *B05D 5/00* (2013.01); *B05D 5/02* (2013.01); *C09D 5/028* (2013.01); *C09D 5/24* (2013.01); *C09D 7/67* (2018.01); *C12Q 1/006* (2013.01); *G01N 27/327* (2013.01); *G01N 27/3271* (2013.01); *G01N 27/3335* (2013.01); *G01N 27/4168* (2013.01); *G01N 33/49* (2013.01); *A61B 5/1486* (2013.01); *A61B 2560/0475* (2013.01); *A61B 2562/0285* (2013.01); *A61B 2562/125* (2013.01); *B82Y 15/00* (2013.01); *B82Y 30/00* (2013.01); *B82Y 40/00* (2013.01); *G01N 33/66* (2013.01); *G01N 2400/00* (2013.01); *Y10S 977/773* (2013.01); *Y10S 977/81* (2013.01); *Y10S 977/896* (2013.01); *Y10S 977/92* (2013.01)

(58) Field of Classification Search
CPC .................. A61B 5/742; A61B 5/1486; A61B 2560/0475; A61B 2562/0285; A61B 2562/125; B01J 13/0013; B05D 5/00; B05D 5/02; C09D 5/028; C09D 5/24; C09D 7/67; C12Q 1/006; G01N 27/327; G01N 27/3271; G01N 27/3335; G01N 27/4168; G01N 33/49; G01N 33/66; G01N 2400/00; B82Y 15/00; B82Y 30/00; B82Y 40/00; Y10S 977/773; Y10S 977/81; Y10S 977/896; Y10S 977/92

See application file for complete search history.

(56) References Cited

U.S. PATENT DOCUMENTS

| | | | |
|---|---|---|---|
| 7,467,003 | B2 | 12/2008 | Brister et al. |
| 7,608,461 | B1 | 10/2009 | Simmons et al. |
| 7,715,893 | B2 | 5/2010 | Kamath et al. |
| 7,761,130 | B2 | 7/2010 | Simpson et al. |
| 7,892,415 | B2 | 2/2011 | Kim et al. |
| 7,896,809 | B2 | 3/2011 | Simpson et al. |
| 8,343,690 | B2 | 1/2013 | Kim et al. |
| 10,040,948 | B1 | 8/2018 | Boo et al. |
| 10,687,746 | B2 | 6/2020 | Boo et al. |
| 11,278,224 | B2 | 3/2022 | Boo et al. |
| 2002/0156355 | A1 | 10/2002 | Gough |
| 2003/0199837 | A1 | 10/2003 | Vachon |
| 2006/0008667 | A1 | 1/2006 | Kim et al. |
| 2006/0211005 | A1 | 9/2006 | Yaku et al. |
| 2006/0278537 | A1 | 12/2006 | Cai et al. |
| 2007/0037237 | A1 | 2/2007 | Kitabayashi et al. |
| 2007/0108068 | A1 | 5/2007 | Suh et al. |
| 2007/0134939 | A1 | 6/2007 | Brueck et al. |
| 2007/0135698 | A1 | 6/2007 | Shah et al. |
| 2008/0096089 | A1 | 4/2008 | Kim et al. |
| 2009/0084678 | A1 | 4/2009 | Joshi et al. |
| 2009/0099436 | A1 | 4/2009 | Brister et al. |
| 2009/0143658 | A1 | 6/2009 | Petisce et al. |
| 2009/0250353 | A1 | 10/2009 | Chen et al. |
| 2011/0034787 | A1 | 2/2011 | Hagino et al. |
| 2013/0217983 | A1 | 8/2013 | Rebec et al. |
| 2014/0061044 | A1 | 3/2014 | Thekkedath et al. |
| 2014/0305804 | A1* | 10/2014 | Madangopal ...... G01N 27/3271 204/403.01 |
| 2015/0090601 | A1 | 4/2015 | Kawde et al. |
| 2015/0230737 | A1 | 8/2015 | Heller |
| 2015/0241418 | A1 | 8/2015 | Wolfrum et al. |
| 2016/0114398 | A1 | 4/2016 | Kim et al. |
| 2016/0192496 | A1 | 6/2016 | Wang et al. |
| 2016/0235347 | A1* | 8/2016 | Baig ................. A61B 5/14532 |
| 2017/0219511 | A1 | 8/2017 | Wang et al. |
| 2019/0167112 | A1 | 6/2019 | Kane et al. |

FOREIGN PATENT DOCUMENTS

| | | |
|---|---|---|
| CN | 101975807 A | 2/2011 |
| CN | 105102972 A | 11/2015 |
| CN | 105353018 A | 2/2016 |
| CN | 106167912 A | 11/2016 |
| CN | 106770567 A | 5/2017 |
| CN | 108982631 A | 12/2018 |
| EP | 2990143 A1 | 3/2016 |
| JP | S62222158 A | 9/1987 |
| JP | 2006-500582 A | 1/2006 |
| JP | 2007-514930 A | 6/2007 |
| JP | 2009-68045 A | 4/2009 |
| JP | 2009544409 A | 12/2009 |
| JP | 2011111652 A | 6/2011 |
| JP | 2013154010 A | 8/2013 |
| JP | 2016-042032 A | 3/2016 |
| JP | 2016173293 A | 9/2016 |
| JP | 2016527388 A | 9/2016 |
| JP | 2016-180768 A | 10/2016 |
| KR | 10-2004-0026323 A | 3/2004 |
| KR | 20040026323 A | 3/2004 |
| KR | 10-0481663 B1 | 4/2005 |
| KR | 10-0736252 B1 | 7/2007 |
| KR | 10-0846456 B1 | 7/2008 |
| KR | 20130043372 A | 4/2013 |
| KR | 10-1288400 B1 | 8/2013 |
| KR | 102016014134 A | 2/2016 |
| KR | 102051811 B1 * | 12/2019 |
| WO | 0116023 A1 | 3/2001 |
| WO | 2004/029611 A1 | 4/2004 |
| WO | 2005045412 A1 | 5/2005 |
| WO | 2012/018777 A1 | 2/2012 |
| WO | 2014/010790 A1 | 1/2014 |

OTHER PUBLICATIONS

Attard et al., "Mesoporous Platinum Films from Lyotropic Liquid Crystalline Phases", Science (1997), vol. 278, pp. 838-840.

Barnickel et al., "Synthesis of Metal Colloids in Inverse Microemulsion," Molecular Physics (1990), vol. 69, No. 1, pp. 1-9.

Basu et al., "Direct Evidence of Acetaminophen Interference with Subcutaneous Glucose Sensing in Humans: A Pilot Study", Diabetes Technology & Therapeutics (2016), vol. 18, Supplement 2, pp. S2-43-S2-47.

(56)  References Cited

OTHER PUBLICATIONS

Boo et al., "Ionic Strength-Controlled Virtual Area of Mesoporous Platinum Electrode", Journal of the American Chemistry Society (2004), vol. 126, No. 14, pp. 4524-4525.

Chiang, "Controlled Growth of Gold Nanoparticles in AOT/C12E4/Isooctane Mixed Reverse Micelles", Journal of Colloid and Interface Science (2001), vol. 239, No. 2, pp. 334-341.

Gabriel et al., "Electrochemical Synthesis of Nanostructured Tellurium Films", Electrochemistry Communications (2002), vol. 4, No. 8, pp. 610-612.

Han et al., "Electrochemical Oxidation of Hydrogen Peroxide at Nanoporous Platinum Electrodes and the Application to Glutamate Microsensor", Electrochimica Acta (2006), vol. 52, pp. 1788-1791.

Herrera et al., "Synthesis and Agglomeration of Gold Nanoparticles in Reverse Micelles", Nanotechnology (2005), vol. 16, pp. S618-S625.

Hollamby et al., "Separation and Purification of Nanoparticles in a Single Step", Langmuir (2010), vol. 26, No. 10, pp. 6989-6994.

International Search Report of corresponding International Patent Application No. PCT/US2018/065838 mailed May 14, 2019.

Joo et al., "Integration of a Nanoporous Platinum Thin Film into a Microfluidic System for Non-enzymatic Electrochemical Glucose Sensing", Analytical Sciences (2007), vol. 23, pp. 277-281.

Jurek et al., "Nanoparticles Preparation Using Microemulsion Systems", Microemulsions: An Introduction to Properties and Applications (2012), pp. 229-250.

Kirwan et al., "Modifications of Poly(o-phenylenediamine) Permselective Layer of Pt—Ir for Biosensor Application in Neurochemical Monitoring", Sensors (2007), vol. 7, pp. 420-437.

Lee et al., "Disposable Non-Enzymatic Blood Glucose Sensing Strip Based on Nanoporous Platinum Particles", Applied Materials Today (2018), vol. 10, pp. 24-29.

Li et al., "Facile Synthesis of Concentrated Gold Nanoparticles with Low Size-Distribution in Water: Temperature and pH Controls", Nanoscale Research Letters (2011), vol. 6, No. 440, pp. 1-10.

Li et al., "Surfactant Removal for Colloidal Nanoparticles from Solution Synthesis: The Effect on Catalytic Performance", ACS Catalysis (2012), vol. 2, pp. 1358-1362.

Moussy et al., "Performance of Subcutaneously Implanted Needle-Type Glucose Sensors Employing a Novel Trilayer Coating", Analytical Chemistry (1993), vol. 65, No. 15, pp. 2072-2077.

Naresh et al., "Removal of Surfactant and Capping Agent from Pd Nanocubes (Pd-NCs) Using Tert-Butylamine: Its Effect on Electrochemical Characteristics", Journal of Materials Chemistry A (2013), vol. 1, pp. 8553-8559.

Office Action of corresponding Korean Patent Application No. 10-2016-0175894, mailed Aug. 10, 2018.

Park et al., "Apparent Electrocatalysis on 3D Nanoporous Platinum Film Electroplated from Hexagonal Lyotropic Liquid Crystalline Phase of Triton X-100", Electrochimica Acta (2008), vol. 53, pp. 6143-6148.

Park et al., "Arrayed Hybrid Nanoporous Pt Pillars", Electrochemistry Communications (2009), vol. 11, pp. 2225-2228.

Park et al., "Electrochemical Non-Enzymatic Glucose Sensors", Analytica Chimica Acta (2006), vol. 556, pp. 46-57.

Park et al., "Nonenzymatic Continuous Glucose Monitoring in Human Whole Blood Using Electrified Nanoporous Pt", Biosensors and Bioelectronics (2012), vol. 31, pp. 284-291.

Park et al., "Nonenzymatic Glucose Detection Using Mesoporous Platinum", Analytical Chemistry (2003), vol. 75, No. 13, pp. 3046-3049.

Park et al., "Structural and Electrochemical Features of 3D Nanoporous Platinum Electrodes", Electrochimica Acta (2010), vol. 55, pp. 2029-2035.

Park et al., Supporting Information for "Nonenzymatic Detection of Glucose Using Mesoporous Platinum", Analytical Chemistry (2003), vol. 75, No. 13, pp. S1-S5.

Park et al., "Three-Dimensional Interstitial Nanovoid of Nanoparticulate Pt Film Electroplated from Reverse Micelle Solution", Chemistry of Materials (2007), vol. 19, No. 14, pp. 3373-3375.

Sayyah et al., "Electropolymerization of O-Phenylenediamine on Pt-Electrode from Aqueous Acidic Solution: Kinetic, Mechanism, Electrochemical Studies and Characterization of the Polymer Obtained", Journal of Applied Polymer Science (2009), vol. 112, pp. 3695-3706.

Sayyah et al., "Electropolymerization of p-Phenylenediamine on Pt-Electrode from Aqueous Acidic Solution: Kinetics, Mechanism, Electrochemical Studies, and Characterization of the Polymer Obtained", Journal of Applied Polymer Science (2010), vol. 117, pp. 943-952.

Urata et al., "Dialysis Process for the Removal of Surfactants to Form Colloidal Mesoporous Silica Nanoparticles", Chemical Communications (2009), issue 34, pp. 5094-5096.

U.S. Appl. No. 15/844,484, filed Dec. 15, 2017.

U.S. Appl. No. 62/589,513, filed Nov. 21, 2017.

U.S. Appl. No. 62/599,631, filed Dec. 15, 2017.

U.S. Appl. No. 15/844,479, filed Dec. 15, 2017.

U.S. Appl. No. 15/844,507, filed Dec. 15, 2017.

U.S. Appl. No. 15/844,515, filed Dec. 15, 2017.

U.S. Appl. No. 15/845,668, filed Dec. 18, 2017.

U.S. Appl. No. 16/057,621, filed Aug. 7, 2018.

U.S. Appl. No. 16/195,271, filed Nov. 19, 2018.

U.S. Appl. No. 16/450,868, filed Jun. 24, 2019.

U.S. Appl. No. 16/450,763, filed Jun. 24, 2019.

U.S. Appl. No. 16/167,298, filed Oct. 22, 2019.

U.S. Appl. No. 16/809,110, filed Mar. 4, 2020.

U.S. Appl. No. 17/521,533, filed Nov. 9, 2021.

Hollamby, Separation and Purification of Nanoparticles in a Single Step, Langmuir 2010, 26(10), 6989-6994 (Year: 2010).

Li, Facile synthesis of concentrated gold nanoparticles with low size-distribution in water: temperature and pH controls, Nanoscale Research Letters, 2011, 6:440, p. 1-10 (Year: 2011).

KR20237040443—Written Decision on Registration mailed on Oct. 22, 2024, 15 pages.

JP2020533113—Search Report mailed on Nov. 19, 2021, 33 pages.

JP2020533113—Office Action mailed on May 24, 2022, 6 pages.

JP2020533113—Written Opinion mailed on Jun. 8, 2022, 7 pages.

JP2020533113—Decision to Grant a Patent mailed on Jul. 12, 2022, 5 pages.

CN201880073713.7—First Office Action mailed on Sep. 5, 2022, 10 pages.

CN201880073713.7—Notice of Grant of Patent mailed on Jan. 10, 2023, 3 pages.

KR20237040443—Request for the Submission of an Opinion mailed on Mar. 13, 2024, 6 pages.

KR20207020596—Request for the Submission of an Opinion mailed on Jul. 15, 2022, 6 pages.

KR20207020596—Request for the Submission of an Opinion mailed on Jan. 4, 2023, 5 pages.

KR20207020596—Written Decision on Registration mailed on Jul. 11, 2023, 14 pages.

KR20207020596—Written Decision on Registration mailed on Sep. 4, 2023, 6 pages.

U.S. Appl. No. 17/684,031—Non-Final Office Action mailed on Sep. 28, 2022, 7 pages.

U.S. Appl. No. 17/684,031—Notice of Allowance mailed on Mar. 13, 2023, 8 pages.

U.S. Appl. No. 16/450,763—Non-Final Office Action mailed on Aug. 16, 2022, 12 pages.

U.S. Appl. No. 16/450,763—Notice of Allowance mailed on Apr. 18, 2023, 11 pages.

U.S. Appl. No. 16/450,763—Corrected Notice of Allowability mailed on Jul. 26, 2023, 2 pages.

U.S. Appl. No. 15/845,668—Non-Final Office Action mailed on May 25, 2018, 8 pages.

U.S. Appl. No. 15/845,668—Notice of Allowance mailed on Jan. 30, 2019, 7 pages.

U.S. Appl. No. 16/167,298—Non-Final Office Action mailed on Oct. 7, 2020, 8 pages.

U.S. Appl. No. 16/167,298—Notice of Allowance mailed on May 19, 2021, 9 pages.

U.S. Appl. No. 15/844,515—Notice of Allowance mailed on Jul. 24, 2018, 10 pages.

(56)        References Cited

OTHER PUBLICATIONS

U.S. Appl. No. 15/844,515—Supplemental Notice of Allowability mailed on Aug. 27, 2018, 3 pages.
U.S. Appl. No. 16/195,271—Non-Final Office Action mailed on Oct. 9, 2020, 9 pages.
U.S. Appl. No. 16/195,271—Notice of Allowance mailed on Jun. 28, 2021, 9 pages.
U.S. Appl. No. 15/844,507—Non-Final Office Action mailed on Apr. 27, 2018, 8 pages.
U.S. Appl. No. 15/844,507—Notice of Allowance mailed on Jul. 18, 2018, 9 pages.
U.S. Appl. No. 16/450,868—Non-Final Office Action mailed on Mar. 15, 2023, 11 pages.
U.S. Appl. No. 16/450,868—Notice of Allowance mailed on Jul. 5, 2023, 8 pages.
U.S. Appl. No. 16/450,868—Corrected Notice of Allowability mailed on Aug. 9, 2023, 2 pages.
U.S. Appl. No. 15/844,479—Non-Final Office Action mailed on May 25, 2018, 8 pages.
U.S. Appl. No. 15/844,479—Notice of Allowance mailed on Jan. 30, 2019, 9 pages.
U.S. Appl. No. 16/809,110—Non-Final Office Action mailed on Apr. 27, 2021, 6 pages.
U.S. Appl. No. 16/809,110—Notice of Allowance mailed on Nov. 23, 2021, 9 pages.
U.S. Appl. No. 16/809,110—Final Office Action mailed on Aug. 10, 2021, 6 pages.
U.S. Appl. No. 16/057,621—Non-Final Office Action mailed on Feb. 7, 2019, 9 pages.
U.S. Appl. No. 16/057,621—Notice of Allowance mailed on Feb. 13, 2020, 8 pages.
U.S. Appl. No. 16/057,621—Final Office Action mailed on Nov. 8, 2019, 7 pages.
U.S. Appl. No. 16/057,621—Advisory Action mailed on Jan. 27, 2020, 3 pages.
U.S. Appl. No. 16/057,621—Corrected Notice of Allowability mailed on Apr. 9, 2020, 5 pages.

U.S. Appl. No. 15/844,484—Non-Final Office Action mailed on Mar. 16, 2018, 16 pages.
U.S. Appl. No. 15/844,484—Notice of Allowance mailed on May 14, 2018, 9 pages.
U.S. Appl. No. 15/844,484—Notice of Allowability mailed on Jun. 5, 2018, 6 pages.
U.S. Appl. No. 17/521,533—Non-Final Office Action mailed on Dec. 18, 2024, 16 pages.
Sattayasamitsathit et al., "Fabrication of Nanoporous Copper Film for Electrochemical Detection of Glucose", Electroanalysis., vol. 21, Issue No. 21, Jul. 6, 2009, pp. 2371-2377.
U.S. Appl. No. 18/229,571—Non-Final Office Action mailed on Feb. 20, 2025, 13 pages.
Zhang et al., On-chip highly sensitive saliva glucose sensing using multilayer films composed of single-walled carbon nanotubes, gold nanoparticles, and glucose oxidase, Sensing and Bio-Sensing Research, vol. 4, Jun. 2015, pp. 96-102.
IN202027024891—Office Action mailed on May 27, 2022, 6 pages.
IN202027024891—Intimation of Grant mailed on Mar. 14, 2024, 1 page.
EP18839787.1—Office Action mailed on Mar. 27, 2024, 5 pages.
EP18839787.1—Office Action mailed on Jun. 8, 2022, 5 pages.
EP18839787.1—Office Action mailed on May 28, 2024, 5 pages.
JP2023195941—Search Report mailed on Sep. 11, 2024, 31 pages.
JP2023195941—Office Action mailed on Sep. 10, 2024, 6 pages.
JP2023195941—Written Opinion mailed on Jan. 27, 2025, 2 pages.
JP2023195941—Decision to Grant a Patent mailed on Feb. 18, 2025, 5 pages.
KR20237040443—Written Opinion mailed on Apr. 25, 2024, 15 pages.
JP2022126106—Search Report mailed on Aug. 31, 2023, 26 pages.
JP2022126106—Decision to Grant a Patent mailed on Sep. 19, 2023, 5 pages.
KR20207020596—Written Opinion mailed on Sep. 13, 2022, 7 pages.
KR20207020596—Written Opinion mailed on Jan. 10, 2023, 4 pages.
KR20207020596—Written Opinion mailed on Aug. 16, 2023, 6 pages.

* cited by examiner

117

119

118

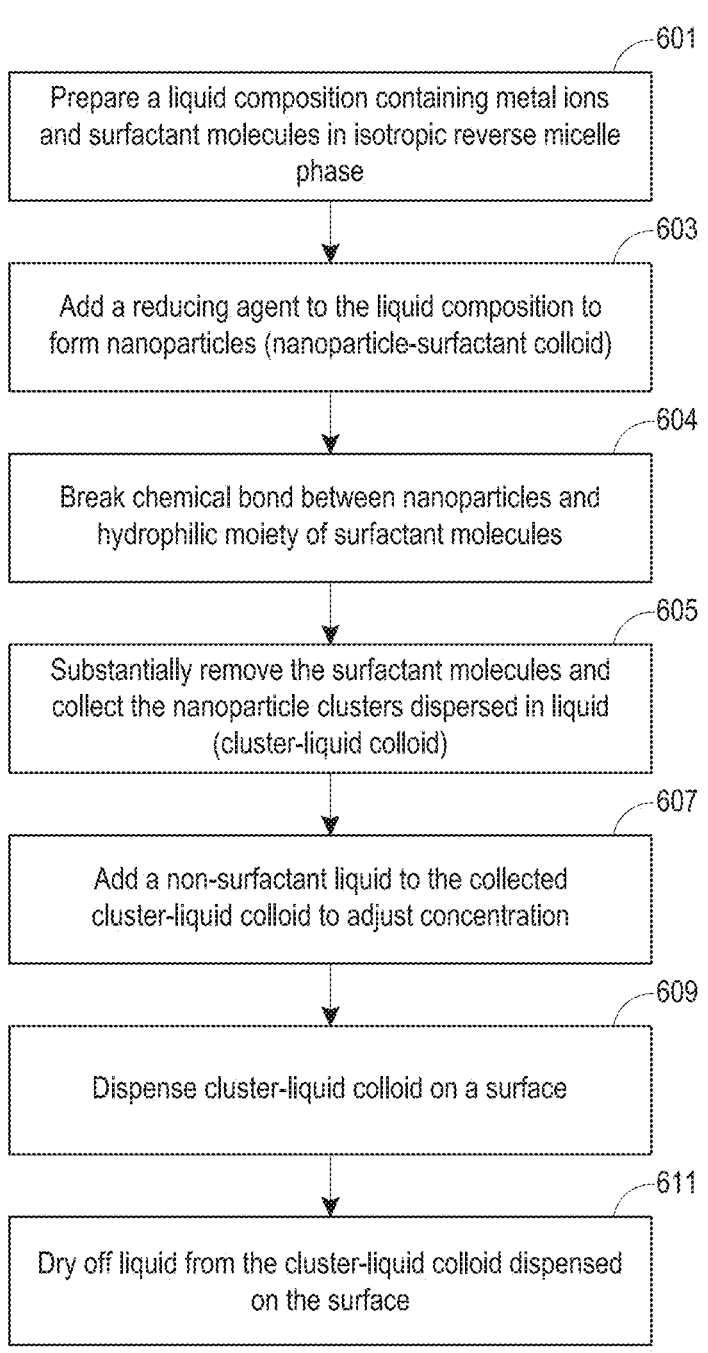

601

Prepare a liquid composition containing metal ions and surfactant molecules in isotropic reverse micelle phase

603

Add a reducing agent to the liquid composition to form nanoparticles (nanoparticle-surfactant colloid)

604

Break chemical bond between nanoparticles and hydrophilic moiety of surfactant molecules

605

Substantially remove the surfactant molecules and collect the nanoparticle clusters dispersed in liquid (cluster-liquid colloid)

607

Add a non-surfactant liquid to the collected cluster-liquid colloid to adjust concentration

609

Dispense cluster-liquid colloid on a surface

611

Dry off liquid from the cluster-liquid colloid dispensed on the surface

FIG. 6B

Reverse Micelle Phase
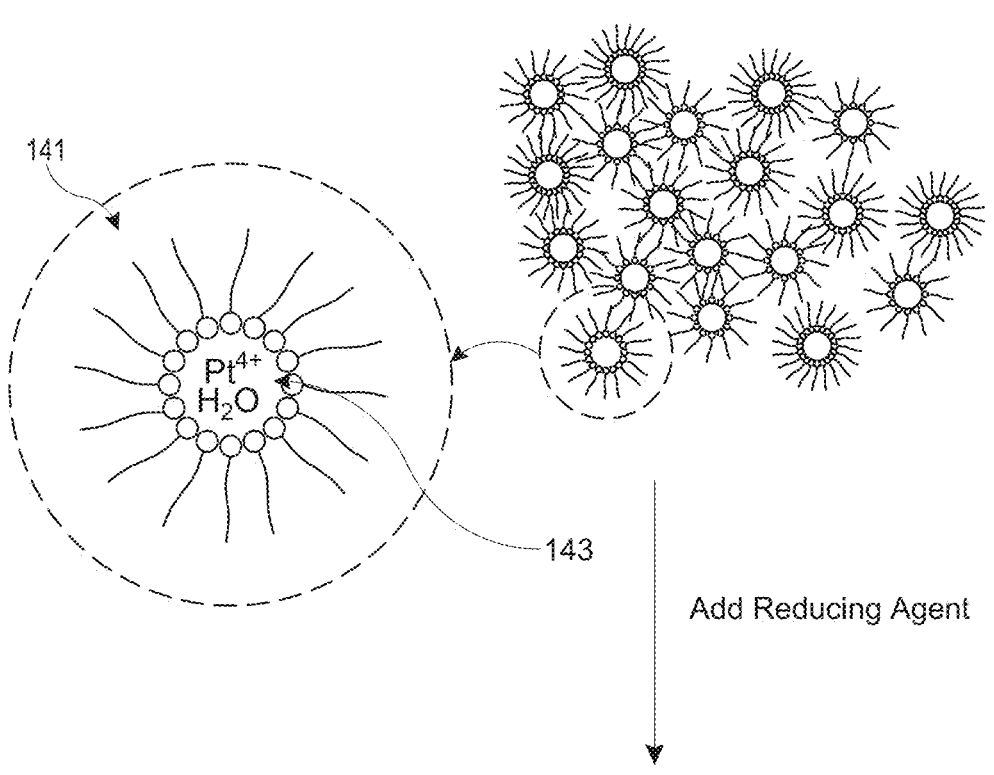
141
143
Add Reducing Agent
Nanoparticle-Surfactant Colloid
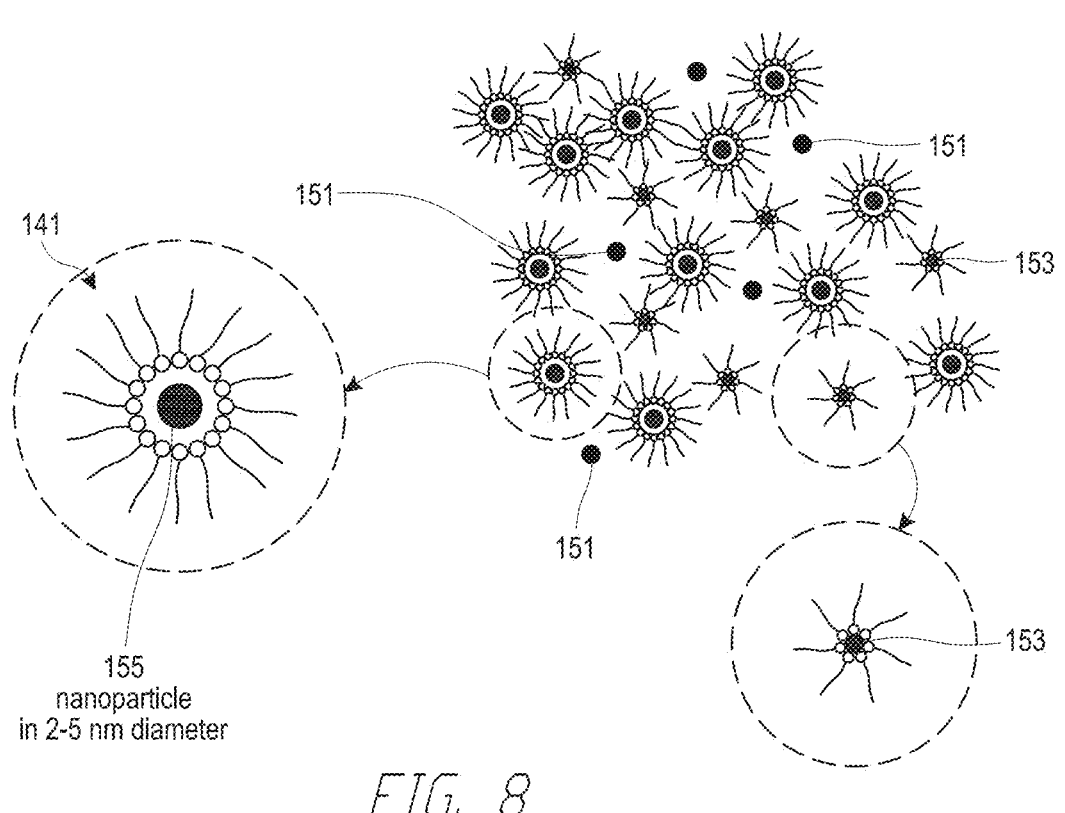
151
153
141
151
151
155
nanoparticle
in 2-5 nm diameter
153
FIG. 8

NANOPARTICLE-SURFACTANT COLLOID

CLUSTER COLLOID

1606

1602
1601
1605
1603

1607
1609

1602
1601
1605
1603

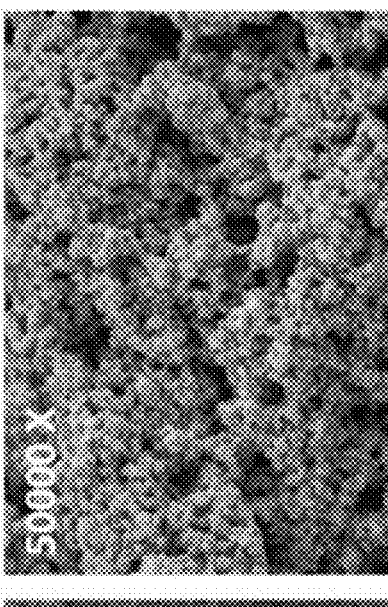
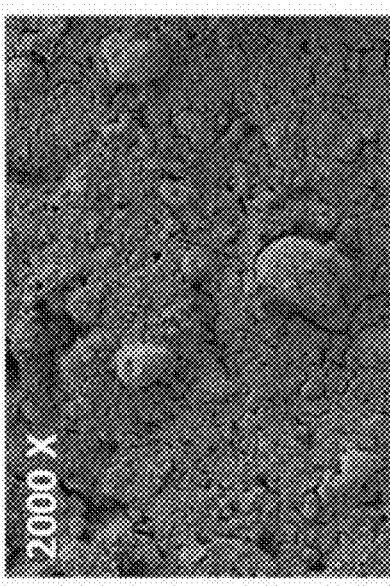
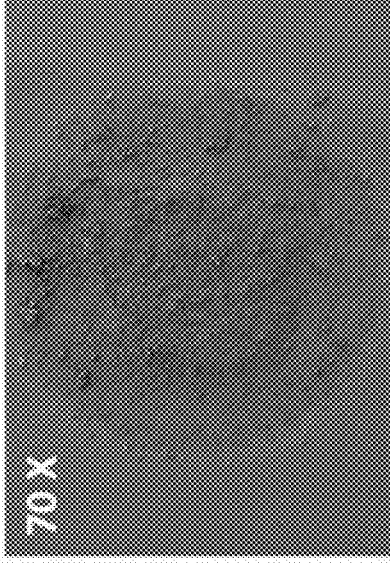
FIG. 17C 1.4-1.6 nm

2401

Determine concentration of monomer for polymerization

2403

Form a porous polymer layer by polymerization with the determined concentration

2405

Adjust porosity of the porous polymer layer (optional)

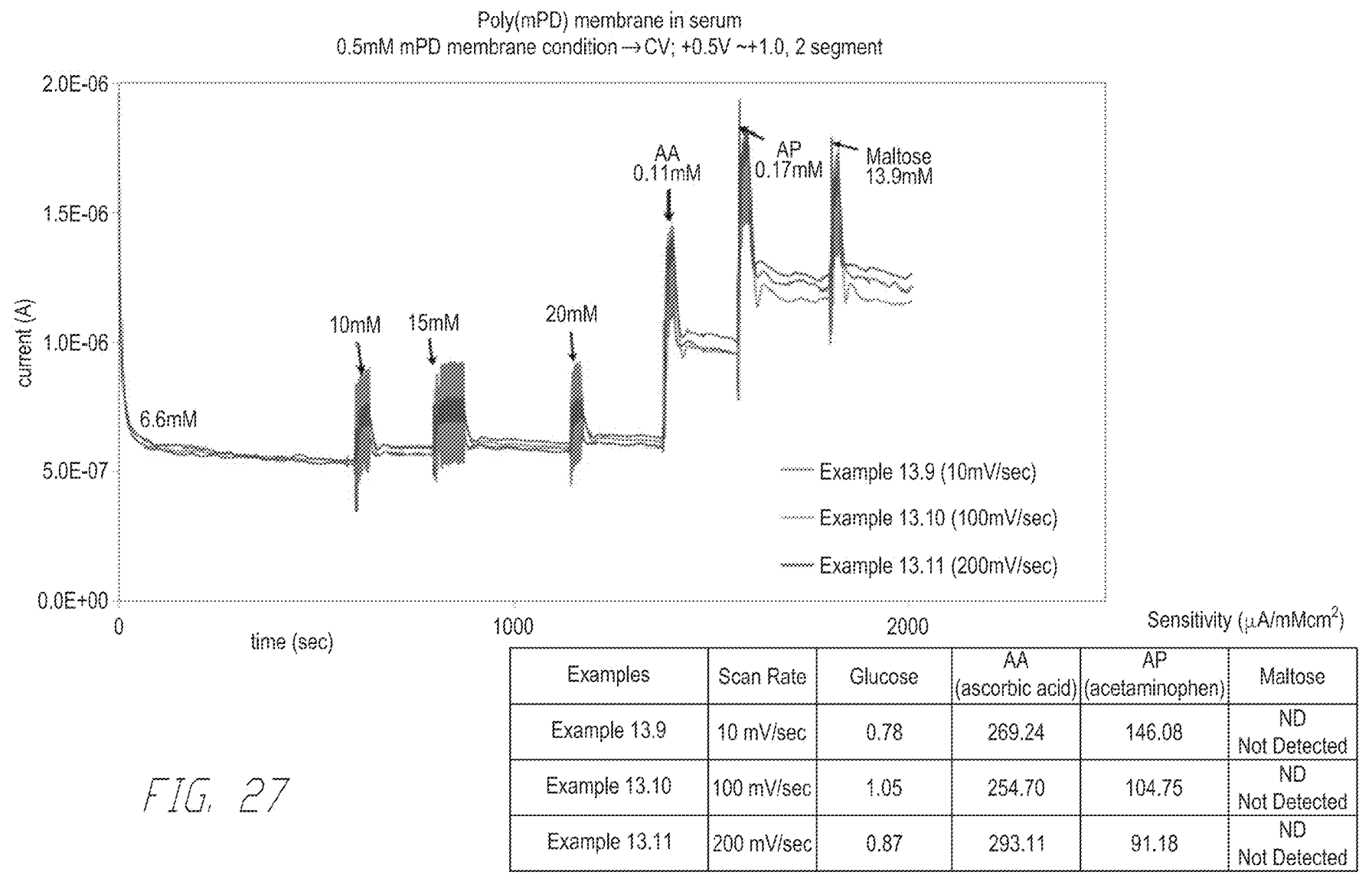

Poly(mPD) membrane in serum
0.5mM mPD membrane condition → CV; +0.5V ~+1.0, 2 segment —— Example 13.9 (10mV/sec)
—— Example 13.10 (100mV/sec)
—— Example 13.11 (200mV/sec)

| Examples | Scan Rate | Glucose | AA (ascorbic acid) | AP (acetaminophen) | Maltose |
|---|---|---|---|---|---|
| Example 13.9 | 10 mV/sec | 0.78 | 269.24 | 146.08 | ND Not Detected |
| Example 13.10 | 100 mV/sec | 1.05 | 254.70 | 104.75 | ND Not Detected |
| Example 13.11 | 200 mV/sec | 0.87 | 293.11 | 91.18 | ND Not Detected |

Sensitivity ($\mu A/mMcm^2$)

*FIG. 27*

Poly(mPD) membrane in serum
1mM mPD membrane condition→CV; +0.5V ~+1.0, 2 segment
chronoamperometry +0.0 ~+1.0V, 2 steps, pulse width 1.0sec —— Example 13.12 (10mV/sec)
······· Example 13.13 (100mV/sec)
—— Example 13.14 (200mV/sec)

| Examples | Scan Rate | Glucose | AA (ascorbic acid) | AP (acetaminophen) | Maltose |
|---|---|---|---|---|---|
| Example 13.12 | 10 mV/sec | 0.22 | 50.15 | 87.55 | ND Not Detected |
| Example 13.13 | 100 mV/sec | 0.40 | 78.26 | 105.25 | ND Not Detected |
| Example 13.14 | 200 mV/sec | 0.65 | 81.52 | 101.47 | ND Not Detected |

Sensitivity ($\mu$A/mMcm$^2$)

*FIG. 28*

| Examples | Scan Rate | Glucose | AA (ascorbic acid) | AP (acetaminophen) | Maltose |
|---|---|---|---|---|---|
| Example 13.15 | 10 mV/sec | 0.28 | 54.09 | 159.85 | ND Not Detected |
| Example 13.16 | 100 mV/sec | 0.49 | 81.06 | 157.40 | ND Not Detected |
| Example 13.17 | 200 mV/sec | 0.37 | 96.74 | 148.68 | ND Not Detected |

Sensitivity ($\mu A/mMcm^2$)

| Regions | A | B | C | D | E | Total |
|---|---|---|---|---|---|---|
| Number of dots | 56 | 37 | 0 | 9 | 0 | 102 |
| Percentage | 54.9% | 36.3% | 0.0% | 8.8% | 0.0% | 100% |

GLUCOSE-SENSING DEVICE WITH MALTOSE BLOCKING LAYER

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure relates to glucose-sensing.

Discussion of the Related Technology

A high level of interest exists in the healthcare community and industry for improving the technologies of sensing and monitoring blood glucose levels. Today, most glucose sensors use an electrochemical method. Most, if not all, electrochemical sensors use enzyme-based electrochemical sensors.

SUMMARY

One aspect of the invention provides a colloid composition comprising: a number of clusters of nanoparticles dispersed in a liquid, wherein each cluster comprises a number of nanoparticles that are clustered together to form a irregularly shaped body having a nano-sized or micro-sized length, wherein individual nanoparticles have a discrete body in a generally oval or spherical shape with a diameter of about 2 nm to about 5 nm, wherein interparticular gaps are formed between adjacent nanoparticles inside each cluster and have an interparticular gap distance of about 0.5 nm to about 2 nm.

In the foregoing colloid composition, the interparticular gaps may be distributed generally throughout in each cluster. The composition may be substantially free of a surfactant. The liquid may comprise water, wherein the colloid composition may comprise a surfactant in an amount smaller than 2 parts by weight with reference to 100 parts by weight of the nanoparticles contained therein. The nanoparticles contained in the colloid composition may be in an amount between about 0.01 wt % and about 2 wt % with reference to the total weight of the colloid composition. The nanoparticles contained in the colloid composition may be in an amount between about 0.01 wt % and about 1 wt % with reference to the total weight of the colloid composition.

Still in the foregoing colloid composition, the nanoparticles may be primarily made of at least one selected from the group consisting of platinum (Pt), gold (Au), palladium (Pd), rhodium (Rh), titanium (Ti), ruthenium (Ru), tin (Sn), nickel (Ni), copper (Cu), indium (In), thallium (Tl), zirconium (Zr), iridium (Ir), and one or more oxides of each of the foregoing elements. The nanoparticles may be primarily made of platinum (Pt), wherein the interparticular gaps may be distributed generally throughout in each cluster, wherein the colloid composition may comprise a surfactant in an amount smaller than 1 parts by weight with reference to 100 parts by weight of the nanoparticles contained therein, wherein the nanoparticles contained in the colloid composition may be in an amount between about 0.1 wt % and about 1 wt % with reference to the total weight of the colloid composition.

Another aspect of the invention provides a method of making a nanoporous layer. The method comprises dispensing the foregoing colloid composition over a substrate; subjecting the dispensed colloid composition to drying such that the clusters contained in the dispensed composition are deposited over the substrate and also stacked over one another to provide a nanoporous layer over the substrate, wherein the nanoporous layer comprises irregularly shaped bodies formed of the clusters that are stacked over one another, wherein the irregularly shaped bodies comprises a number of nanoparticles locally clustered together and interparticular gaps formed between adjacent ones of the nanoparticles in the irregularly shaped bodies, wherein the irregularly shaped bodies are interconnected to provide a three-dimensional interconnected network of irregularly shaped bodies, wherein irregularly shaped spaces are formed between adjacent portions of the irregularly shaped bodies and are nano-sized or micro-sized.

In the foregoing method, the nanoparticles may be generally in an oval or spherical shape having a diameter of about 2 nm to about 5 nm. The interparticular gaps may have an interparticular gap distance of about 0.5 nm to about 2 nm. The irregularly shaped spaces may be interconnected to provide a three-dimensional interconnected network of irregularly shaped spaces. The colloid composition may be dispensed in a predetermined amount to form the nanoporous layer having roughness factor between about 100 and about 2500. The nanoporous layer may comprise a surfactant in an amount smaller than 0.5 parts by weight with reference to 100 parts by weight of the nanoparticles contained therein.

Another aspect of the invention provides a method of making a colloid composition. The method comprises: providing a liquid composition comprising a metal ion, a surfactant and a solvent, wherein the surfactant is in a reverse micelle phase defining hydrophilic spaces; adding a reducing agent to the liquid composition to cause reduction of the metal ion, which forms a first colloid comprising metal nanoparticles and the surfactant, wherein in the first colloid the metal nanoparticles are dispersed along with the reverse micelle phase of the surfactant; and removing the surfactant from the first colloid to provide a second colloid comprising a number of clusters dispersed in a liquid, wherein each cluster comprises a number of nanoparticles that are clustered together to form a irregularly shaped body having a nano-sized or micro-sized length.

In the foregoing method of making, no electric potential may be applied to the liquid composition for reduction of the metal ion therein. The surfactant may be a non-ionic surfactant capable of forming an isotropic reverse micelle phase. Individual nanoparticles may have a discrete body in a generally oval or spherical shape with a diameter of about 2 nm to about 5 nm, wherein interparticular gaps may be formed between adjacent nanoparticles inside each cluster and have an interparticular gap distance of about 0.5 nm to about 2 nm. Removing the surfactant removes a significant amount of the surfactant from the first colloid such that the second colloid is substantially free of the surfactant. Removing the surfactant removes a significant amount of the surfactant from the first colloid such that the second colloid contains the surfactant in an amount smaller than 1 part by weight with reference to 100 parts by weight of the nanoparticles contained therein.

Still in the foregoing method of making, removing the surfactant may comprise: centrifuging the first colloid; and collecting a bottom portion from a centrifuged composition. Removing the surfactant may further comprise repeating a sequence of centrifuging and collecting multiple times. Removing the surfactant may further comprise adding an acid or base to the first colloid prior to centrifuging. Removing the surfactant may further comprise repeating a sequence of adding, centrifuging and collecting multiple times. The nanoparticles contained in the second colloid may be in an amount between about 10 wt % and about 40 wt % with reference to the total weight of the composition. The nanoparticles may be primarily made of at least one selected from the group consisting of platinum (Pt), gold (Au), palladium (Pd), rhodium (Rh), titanium (Ti), ruthenium (Ru), tin (Sn), nickel (Ni), copper (Cu), indium (In), thallium (Tl), zirconium (Zr), iridium (Ir), and one or more oxides of each of the foregoing metals. The nanoparticles may be primarily made of platinum (Pt), wherein the interparticular gaps may be distributed generally throughout in each cluster, wherein the composition may comprise a surfactant in an amount smaller than 2 parts by weight with reference to 100 parts by weight of the nanoparticles contained therein, wherein the nanoparticles contained in the composition may be in an amount of about 0.1 wt % and about 2 wt % with reference to the total weight of the composition.

Another aspect of the invention provides a method of making a nanoporous layer. This method comprises the foregoing method of making a colloid composition to provide the second colloid; dispensing the second colloid over a substrate; subjecting the dispensed second colloid to drying such that the clusters contained in the dispensed composition are deposited over the substrate and also stacked over one another to provide a nanoporous layer over the substrate, wherein the nanoporous layer comprises irregularly shaped bodies formed of the clusters that are stacked over one another, wherein the irregularly shaped bodies comprises a number of nanoparticles locally clustered together and interparticular gaps formed between adjacent ones of the nanoparticles in the irregularly shaped bodies. The irregularly shaped bodies are interconnected to provide a three-dimensional interconnected network of irregularly shaped bodies, wherein irregularly shaped spaces are formed between adjacent portions of the irregularly shaped bodies and are nano-sized or micro-sized, wherein the irregularly shaped spaces are interconnected to provide a three-dimensional interconnected network of irregularly shaped spaces.

In the foregoing method of making a nanoporous layer, the nanoparticles may be generally in an oval or spherical shape having a diameter of about 2 nm to about 5 nm, wherein the interparticular gaps have an interparticular gap distance of about 0.5 nm to about 2 nm. The colloid composition may be dispensed in a predetermined amount to form the nanoporous layer having roughness factor between about 100 and about 2500. The nanoporous layer may comprise a surfactant smaller than 0.1 parts by weight with reference to 100 parts by weight of the nanoparticles contained therein.

Another aspect of the invention provides a nanoporous structure comprising: irregularly shaped bodies comprising a number of nanoparticles locally clustered together and interparticular gaps formed between adjacent ones of the nanoparticles in the irregularly shaped bodies, wherein the nanoparticles may be generally in an oval or spherical shape having a diameter of about 2 nm to about 5 nm, wherein the interparticular gaps have an interparticular gap distance of about 0.5 nm to about 2 nm, wherein the irregularly shaped bodies may be interconnected to provide a three-dimensional interconnected network of irregularly shaped bodies, wherein irregularly shaped spaces are formed between adjacent portions of the irregularly shaped bodies and are nano-sized or micro-sized, wherein the irregularly shaped spaces are interconnected to provide a three-dimensional interconnected network of irregularly shaped spaces.

The foregoing nanoporous structure may be substantially free of surfactant molecules. In the foregoing nanoporous structure, the interparticular gaps may be substantially free of nano-sized organic molecules. The three-dimensional network of irregularly shaped bodies and the three-dimensional network of irregularly shaped intercluster gaps may be complementary to form the nanoporous structure. The interparticular gaps may be substantially interconnected themselves and may be further connected to the three-dimensional interconnected network of irregularly shaped intercluster gaps. The nanoporous structure may be formed by dispensing a solid-liquid colloid comprising irregularly shaped discrete clusters dispersed in liquid and drying the dispensed solid-liquid colloid, in which the irregularly shaped discrete clusters may be stacked to provide the three-dimensional interconnected network of irregularly shaped bodies and the three-dimensional interconnected network of irregularly shaped intercluster gaps. The irregularly shaped intercluster gaps have a mean intercluster gap distance. The nanoparticles may be made of at least one selected from the group consisting of platinum (Pt), gold (Au), palladium (Pd), rhodium (Rh), titanium (Ti), ruthenium (Ru), tin (Sn), nickel (Ni), copper (Cu), indium (In), thallium (Tl), zirconium (Zr), iridium (Ir), and one or more oxides of each of the foregoing metals. The nanoporous structure has roughness factor between about 100 and about 2500.

Another aspect of the invention provides a device comprising: a substrate comprising a surface; and a nanoporous layer formed on the surface and comprising the foregoing nanoporous structure. Still another aspect of the invention provides a non-enzymatic glucose-sensing electrode comprising: at least one conductive layer comprising a surface; and a nanoporous layer formed on the surface and comprising the foregoing nanoporous structure, wherein the non-enzymatic glucose-sensing electrode does not comprise a glucose-specific enzyme.

In the foregoing device or electrode, the at least one conductive layer may comprise an electrically conductive metal layer and an electrically conductive carbon layer formed on the electrically conductive metal layer. The device or electrode does not comprise a biocompatible polymeric material formed over the nanoporous layer. The device or electrode may comprise a biocompatible polymeric material formed over the nanoporous layer.

Still another aspect of the invention provides a one-time use glucose sensing device comprising: a reservoir configured to receive and hold a test liquid; and the foregoing electrode arranged with the reservoir such that the nanoporous layer may be to contact the test liquid when the test liquid may be held in the reservoir. In the one-time use glucose sensing device, the electrode does not comprise a biocompatible polymeric material formed over the nanoporous layer.

Still another aspect of the invention provides a continuous glucose monitoring (CGM) device comprising: a hypodermic needle configured for contacting interstitial fluid of a subject's body; and an electrical circuit connected to the hypodermic needle, wherein the hypodermic needle comprises the foregoing electrode and another electrode that are connected to the electrical circuit.

A still another aspect of the invention provides a non-enzymatic glucose-sensing device comprising: a working electrode comprising a substrate and a nanoporous layer formed over the substrate, the working electrode does not comprise a glucose-specific enzyme, wherein the nanoporous layer may comprise irregularly shaped bodies comprising a number of nanoparticles locally clustered together, wherein interparticular gaps may be formed between adjacent ones of the nanoparticles in the irregularly shaped bodies, wherein the nanoparticles may be generally in an oval or spherical shape having a diameter of about 2 nm to about 5 nm, wherein the interparticular gaps have an interparticular gap distance of about 0.5 nm to about 2 nm, wherein the irregularly shaped bodies may be interconnected to provide a three-dimensional interconnected network of irregularly shaped bodies extending generally throughout the nanoporous layer, wherein irregularly shaped spaces may be formed between adjacent portions of the irregularly shaped bodies and may be nano-sized or micro-sized, wherein the irregularly shaped spaces may be interconnected to provide a three-dimensional interconnected network of irregularly shaped spaces extending generally throughout the nanoporous layer, wherein the nanoporous layer may be configured to cause oxidation of glucose molecule therein in the absence of a glucose-specific enzyme at a bias voltage applied thereto between about 0.2 V and about 0.45 V.

In the foregoing non-enzymatic glucose-sensing device, the nanoporous layer may be substantially free of surfactant molecules, wherein the substrate may comprise at least one conductive layer comprising an electrically conductive or semiconductive material. The interparticular gaps may be substantially free of nano-sized organic molecules. The three-dimensional network of irregularly shaped bodies and the three-dimensional network of irregularly shaped intercluster gaps may be complementary to form the nanoporous layer. The interparticular gaps may be substantially interconnected themselves and may be further connected to the three-dimensional interconnected network of irregularly shaped intercluster gaps.

Still in the foregoing non-enzymatic glucose-sensing device, the nanoporous layer may be formed by dispensing a solid-liquid colloid comprising irregularly shaped discrete clusters dispersed in liquid and drying the dispensed solid-liquid colloid, in which the irregularly shaped discrete clusters may be stacked to provide the three-dimensional interconnected network of irregularly shaped bodies and the three-dimensional interconnected network of irregularly shaped intercluster gaps. The nanoparticles may be made of at least one selected from the group consisting of platinum (Pt), gold (Au), palladium (Pd), rhodium (Rh), titanium (Ti), ruthenium (Ru), tin (Sn), nickel (Ni), copper (Cu), indium (In), thallium (Tl), zirconium (Zr), iridium (Ir), and one or more oxides of each of the foregoing metals. The nanoporous layer has roughness factor between about 100 and about 2500. The nanoporous electrode may further comprise a maltose-blocking layer formed over the nanoporous layer and configured to substantially block maltose contained in the test fluid from passing therethrough while allowing glucose to pass therethrough. The maltose-blocking layer may comprise poly-phenylenediamine (poly-PD) in a morphology allowing glucose molecules to pass therethrough while effectively blocking maltose molecules from passing therethrough. The bias voltage may be set to be in a range between 0.2 V and 0.45 V.

Still another aspect of the invention provides a non-enzymatic glucose-sensing system comprising: the foregoing non-enzymatic glucose-sensing device; a counter electrode; and a bias voltage supply electrically connected between the working electrode and the counter electrode for supplying a bias voltage between the working electrode and counter electrode.

Still another aspect of the invention provides a method of non-enzymatic glucose sensing. The method comprises: providing the foregoing non-enzymatic glucose-sensing device; applying the bias voltage between the working electrode and the counter electrode while a test fluid contacts both the working electrode and the counter electrode, which causes oxidation of glucose contained in the test fluid at the nanoporous layer; measuring electric current from the working electrode; and processing the electric current with or without additional data to provide a glucose level that corresponds to glucose contained in the test fluid. The bias voltage may be set to be in a range between 0.2 V and 0.45 V.

Another aspect of the invention provides a glucose-sensing electrode, which comprises: a substrate; a nanoporous metal layer formed over the substrate and capable of oxidizing both glucose and maltose without an enzyme specific to glucose or maltose in the glucose-sensing electrode; a maltose-blocking layer formed over the nanoporous metal layer. In the glucose-sensing electrode, the maltose-blocking layer has porosity that permits glucose to pass therethrough and inhibits maltose from passing therethrough toward the nanoporous metal layer such that electric current caused by oxidation of glucose alone in the nanoporous metal layer is higher than 10 $nA/mMcm^2$ and further such that electric current caused by oxidation of maltose alone in the nanoporous metal layer is lower than 5 $nA/mMcm^2$ when a bias voltage of 0.2-0.45 V is applied to the nanoporous metal layer relative to a reference electrode and when the maltose-blocking layer contacts liquid containing glucose in a concentration of 4-20 mM and maltose in a concentration of 4-20 mM.

In the foregoing glucose-sensing electrode, the nanoporous metal layer is capable of oxidizing glucose such that electric current caused by oxidation of glucose alone is higher than 10 $nA/mMcm^2$ when applying a bias voltage of 0.2-0.45 V and contacting liquid containing glucose in a concentration of 4-20 mM without the maltose-blocking layer thereover. The nanoporous metal layer is further capable of oxidizing maltose such that electric current caused by oxidation of maltose alone in higher than 10 $nA/mMcm^2$ when applying a bias voltage of 0.2-0.45 V and when contacting liquid containing maltose in a concentration of 4-20 mM without the maltose-blocking layer thereover. The maltose-blocking layer may comprise poly-phenylenediamine (poly-PD) and have a thickness between 10 nm and 40 nm. The maltose-blocking layer may consist essentially of poly-phenylenediamine (poly-PD) and have a thickness between 10 nm and 35 nm. The maltose-blocking layer may consist of poly-phenylenediamine (poly-PD) and have a thickness between 10 nm and 40 nm.

In the foregoing glucose-sensing electrode, the nanoporous metal layer may comprise irregularly shaped bodies comprising a number of nanoparticles locally clustered together and interparticular gaps formed between adjacent ones of the nanoparticles in the irregularly shaped bodies. Here, the nanoparticles are generally in an oval or spherical shape having a diameter of about 2 nm to about 5 nm. The interparticular gaps may have an interparticular gap distance of about 0.5 nm to about 2 nm. The irregularly shaped bodies may be interconnected to provide a three-dimensional interconnected network of irregularly shaped bodies. Irregularly shaped spaces may be formed between adjacent portions of the irregularly shaped bodies and are nano-sized or micro-sized. The irregularly shaped spaces may be interconnected to provide a three-dimensional interconnected network of irregularly shaped spaces.

The foregoing glucose-sensing electrode may further comprise an electrolyte ion-blocking layer formed over the maltose-blocking layer and a biocompatibility layer formed over the electrolyte ion blocking layer. The electrolyte ion-blocking layer is configured to inhibit $Na^+$, $K^+$, $Ca^{2+}$, $Cl^-$, $PO_4^{3-}$ and $CO_3^{2-}$ contained in the liquid from diffusing toward the nanoporous metal layer such that there is a substantial discontinuity of a combined concentration of $Na^+$, $K^+$, $Ca^{2+}$, $Cl^-$, $PO_4^{3-}$ and $CO_3^{2-}$ between over the electrolyte ion-blocking layer and below the electrolyte ion-blocking layer. The electrolyte ion-blocking layer may facilitate conditioning of the glucose-sensing electrode such that conditioning of the glucose-sensing electrode is complete within 30 minutes from contacting the subject's bodily fluid with the application of the bias voltage of 0.2-0.45 V.

Another aspect of the invention provides an apparatus comprising: a single integrated body comprising a subcutaneous portion and a terminal portion; the subcutaneous portion comprising the foregoing glucose-sensing electrode and the reference electrode, each of which is exposed for contacting interstitial fluid of a first subject when the subcutaneous portion is subcutaneously inserted into the first subject's body; and the terminal portion configured for coupling with a counterpart device and comprising a first terminal electrically connected to the glucose-sensing electrode and a second terminal electrically connected to the reference electrode.

Still another aspect of the invention provides an apparatus comprising: a single integrated body comprising the foregoing glucose-sensing electrode and the reference electrode, the single integrated body further comprising a reservoir configured to at least temporarily hold a test fluid therein, wherein the glucose-sensing electrode and the reference electrode are arranged in the single integrated body such that when the test fluid is held in the reservoir each of the glucose-sensing electrode and the reference electrode is configured to contact the test fluid.

A further aspect of the invention provides a method of making a glucose-sensing electrode. The method comprises: providing a nanoporous metal layer capable of oxidizing both glucose and maltose without an enzyme specific to glucose or maltose in the glucose-sensing electrode; forming a poly-phenylenediamine (poly-PD) film over the nanoporous platinum layer such that the poly-PD film allows glucose to pass therethrough and blocks maltose from passing therethrough. Here, the poly-PD film has porosity to permit glucose to pass therethrough and to inhibit maltose from passing therethrough toward the nanoporous metal layer such that electric current caused by oxidation of glucose alone in the nanoporous metal layer is higher than 10 $nA/mMcm^2$ and further such that electric current caused by oxidation of maltose alone in the nanoporous metal layer is lower than 5 $nA/mMcm^2$, when a bias voltage of 0.2-0.45 V is applied to the nanoporous metal layer relative to a reference electrode and when the poly-PD film contacts liquid containing glucose in a concentration of 4-20 mM and maltose in a concentration of 4-20 mM.

In the foregoing method of making glucose-sensing electrode, forming the poly-PD film may comprise performing electrochemical polymerization using the nanoporous metal layer as an electrode for the electrochemical polymerization. Forming the poly-PD film may comprise providing a polymer layer comprising poly-PD and adjusting the porosity of the polymer layer when the polymer layer may not have enough porosity to permit glucose to pass therethrough such that electric current caused by oxidation of glucose alone in the nanoporous metal layer is lower than 10 $nA/mMcm^2$. Adjusting the porosity may comprise subjecting the polymer layer to at least one electric shock while the polymer layer contacts an acidic solution. Forming the poly-PD film may comprise polymerizing poly-PD from a liquid composition containing phenylenediamine at a concentration, wherein when the concentration is higher than a predetermined value, forming the poly-PD film further comprises adjusting the porosity of the polymer layer. Adjusting the porosity may comprise subjecting the polymer layer to at least one electric shock while the polymer layer contacts an acidic solution.

In the foregoing method of making glucose-sensing electrode, forming the poly-PD film may comprise providing a polymer layer comprising poly-PD without further adjusting the porosity of the polymer layer when the polymer layer may have sufficient porosity to permit glucose to pass therethrough such that electric current caused by oxidation of glucose alone in the nanoporous metal layer is expected to be higher than 10 $nA/mMcm^2$. Forming the poly-PD film may comprise polymerizing poly-PD from a liquid composition containing phenylenediamine at a concentration, wherein when the concentration is lower than a predetermined value, the method does not comprise adjusting the porosity of the polymer layer to form the poly-PD film.

One aspect of the invention provides a glucose-sensing electrode, which comprises: an electrically conductive layer; a nanoporous metal layer formed over the electrically conductive layer; an electrolyte ion-blocking layer formed over the nanoporous metal layer; and a biocompatibility layer formed over the electrolyte ion-blocking layer. The glucose-sensing electrode does not include a glucose-specific enzyme. When contacting liquid containing glucose, $Na^+$, $K^+$, $Ca^{2+}$, $Cl^-$, $PO_4^{3-}$ and $CO_3^{2-}$, the electrolyte ion-blocking layer is configured to inhibit $Na^+$, $K^+$, $Ca^{2+}$, $PO_4^{3-}$ and $CO_3^{2-}$ contained in the liquid from diffusing toward the nanoporous metal layer such that there is a substantial discontinuity of a combined concentration of $Na^+$, $K^+$, $Ca^{2+}$, $Cl^-$, $PO_4^{3-}$ and $CO_3^{2-}$ between over the electrolyte ion-blocking layer and below the electrolyte ion-blocking layer.

In the foregoing glucose-sensing electrode, when applying a bias voltage of 0.2-0.45 V thereto relative to a reference electrode, the glucose-sensing electrode is configured to cause oxidation of glucose in the nanoporous metal layer and configured to generate an electric current that is a sum of a glucose-oxidation current caused by the glucose oxidation alone and a background current caused by other electrochemical interactions of the liquid and the glucose-sensing electrode. When the liquid contains glucose at a concentration of 4-20 mM (approximately 72-360 mg/dL), at steady state the glucose-oxidation current is at a level higher than 10 $nA/mMcm^2$.

In the foregoing glucose-sensing electrode, the combined concentration below the electrolyte ion-blocking layer is greater than 0% and lower than about 10% of the combined concentration above the electrolyte ion-blocking layer. The combined concentration below the electrolyte ion-blocking layer is greater than 0% and lower than about 5% of the combined concentration above the electrolyte ion-blocking layer. The electrolyte ion-blocking layer may comprise a porous and hydrophobic polymer layer that is configured to limit mobility of $Na^+$, $K^+$, $Ca^{2+}$, $Cl^-$, $PO_4^{3-}$ and $CO_3^{2-}$ therethrough while not limiting mobility of glucose molecules therethrough.

In the foregoing glucose-sensing electrode, the electrolyte ion-blocking layer may comprise at least one selected from the group consisting of poly(methyl methacrylate) (PMMA), poly(hydroxyethyl methacrylate) (PHEMA), and poly(methyl methacrylate-co-ethylene glycol dimethacrylate) (PMMA-EG-PMMA). The electrolyte ion-blocking layer may comprise at least one selected from the group consisting of a copolymer of methylmethacrylate and butylmethacrylate, and polymers obtained from polymerization of one or more monomers including branched or unbranched C1-C8 alkylmethacrylate, branched or unbranched C1-C8 cycloalkylmethacrylate, branched or unbranched C1-C8 alkylacrylate, branched or unbranched C1-C8 cycloalkylacrylate, and branched or unbranched C1-C8 cycloalkylmethacrylate, wherein the one or more monomers are selected from the group consisting of methylmethacrylate, ethylmethacrylate, propylmethacrylate, butylmethacrylate, pentylmethacrylate, hexylmethacrylate, cyclohexylmethacrylate, 2-ethylhexylmethacrylate, methylacrylate, ethylacrylate, propylacrylate, butylacrylate, pentylacrylate, hexylacrylate, cyclohexylacrylate, and 2-ethylhexylacrylate.

In the foregoing glucose-sensing electrode, the glucose-sensing electrode may be a continuous glucose monitoring (CGM) electrode, wherein the liquid is bodily fluid of a subject. The electrolyte ion-blocking layer is configured to facilitate conditioning of the glucose-sensing electrode such that conditioning of the glucose-sensing electrode is complete within 30 minutes from contacting the subject's bodily fluid with the application of the bias voltage of 0.2-0.45 V. Conditioning of the glucose-sensing electrode may be considered as complete when a rate of decrease of the electric current is smaller than a first predetermined value and/or when the electric current stays smaller than a second predetermined value.

The glucose-sensing electrode may further comprise a maltose-blocking layer interposed between the nanoporous metal layer and the electrolyte ion-blocking layer, wherein the maltose-blocking layer may comprise poly-phenylene-diamine (poly-PD). The maltose-blocking layer may be configured to let glucose pass therethrough and substantially block maltose from passing therethrough such that at steady state the glucose-oxidation current is at a level higher than 10 nA/mMcm² while a maltose oxidation current caused by oxidation of maltose alone is lower than 5 nA/mMcm².

The reference electrode may be configured to provide a reference level of electric potential for the bias voltage applied to the glucose-sensing electrode, whether reduction of a chemical entity occurs in the reference electrode or not. In a three-electrode electrochemical cell, in addition to the reference electrode, a counter electrode is provided for reduction of the chemical entity therein, whereas in a two-electrode electrochemical cell, reduction of the chemical entity occurs in the reference electrode.

In the foregoing glucose-sensing electrode, the nanoporous metal layer may comprise: irregularly shaped bodies comprising a number of nanoparticles locally clustered together and interparticular gaps formed between adjacent ones of the nanoparticles in the irregularly shaped bodies, wherein the nanoparticles are generally in an oval or spherical shape having a diameter of about 2 nm to about 5 nm, wherein the interparticular gaps have an interparticular gap distance of about 0.5 nm to about 2 nm. Here, the irregularly shaped bodies may be interconnected to provide a three-dimensional interconnected network of irregularly shaped bodies. Irregularly shaped spaces may be formed between adjacent portions of the irregularly shaped bodies and are nano-sized or micro-sized, and the irregularly shaped spaces are interconnected to provide a three-dimensional interconnected network of irregularly shaped spaces.

Another aspect of the invention provides a sensor apparatus comprising: a single integrated body comprising a subcutaneous portion and a terminal portion; the subcutaneous portion comprising a glucose-sensing electrode and the reference electrode, each of which is exposed for contacting interstitial fluid of a first subject when the subcutaneous portion is subcutaneously inserted into the first subject's body; and the terminal portion configured for coupling with a counterpart device and comprising a first terminal electrically connected to the glucose-sensing electrode and a second terminal electrically connected to the reference electrode. The glucose-sensing electrode may include one or more features of the foregoing glucose-sensing electrode.

Another aspect of the invention provides a method of continuous glucose monitoring. The method comprises: providing a sensor apparatus; subcutaneously inserting the subcutaneous portion of the glucose-sensing electrode into a first subject's body such that the glucose-sensing electrode and the reference electrode contact interstitial fluid of the first subject's body; causing to apply a bias voltage of 0.2-0.45 V to the glucose-sensing electrode relative to the reference electrode; measuring electric current generated from the glucose-sensing electrode; computing a glucose level using an electric current value that is obtained by a measurement of the electric current within less than 1 hour from later of subcutaneous insertion of the subcutaneous portion and application of the bias voltage; and presenting, on a display, the computed glucose level as that of the first subject within a range between about 4 mM and about 20 mM (approximately between about 72 mg/dL and about 360 mg/dL). The glucose-sensing electrode may include one or more features of the foregoing glucose-sensing electrode.

A further aspect of the invention provides a sensor apparatus, comprising: a substrate; a first electrode (or glucose-sensing electrode) comprising a first electrically conductive layer formed over the substrate and a glucose-oxidation layer formed over the first electrically conductive layer; a first terminal formed over the substrate and electrically connected to the first electrode; a second electrode comprising a second electrically conductive layer formed over the substrate; a second terminal formed over the substrate and electrically connected to the second electrode; a reference electrode comprising a third electrically conductive layer formed over the substrate; and a third terminal formed over the substrate and electrically connected to the reference electrode.

In the sensor apparatus, when the first electrode contacts liquid containing glucose and ascorbic acid and acetaminophen and when applying a first bias voltage between the first and reference electrodes that is sufficient to oxidize glucose in the glucose-oxidation layer, the glucose-oxidation layer of the first electrode is configured to cause oxidation of glucose and at least one of ascorbic acid and acetaminophen therein and further configured to generate a first electric current comprising a glucose component caused by the glucose oxidation and a first interference component caused by oxidation of at least one of ascorbic acid and acetaminophen in the glucose-oxidation layer. The second electrode is arranged in the apparatus such that, when the first electrode contacts the liquid, the second electrode also contacts the same liquid. The second electrode does not comprise a layer configured to cause oxidation of glucose therein such that, when applying a second bias voltage between the second and reference electrodes, the second electrode is configured to cause oxidation of at least one of ascorbic acid and acetaminophen therein but not to cause oxidation of glucose therein and further configured to generate a second electric current comprising a second interference component caused by oxidation of at least one of ascorbic acid and acetaminophen in the second electrode and not caused by oxidation of glucose. The apparatus is configured to provide the first electric current at the first terminal and the second electric current at the second terminal.

The foregoing sensor apparatus may be configured to provide the second electric current in connection with the first electric current when it provides the first electric current. The sensor apparatus may be configured to generate the first electric current and the second electric current at the same time. The sensor apparatus may be configured to provide the first electric current and the second electric current along with information indicative of time of generating first electric current and the second electric current. The sensor apparatus may be configured to provide the second electric current together with the first electric current whenever it provides the first electric current. In the foregoing sensor apparatus, the first electric current may further comprise a first background current caused by other electrochemical interactions of the liquid and the glucose-sensing layer, wherein the second electric current may further comprise a second background current caused by other electrochemical interactions of the liquid and the second electrode.

In the foregoing sensor apparatus, when the first bias voltage is between 0.2 V and 0.32 V, the glucose-oxidation layer is configured to oxidize glucose and ascorbic acid but not acetaminophen, and the first interference component is caused by oxidation of ascorbic acid and not by oxidation of acetaminophen. When the second bias voltage is between 0.2 V and 0.32 V, the second electrode is configured to oxidize ascorbic acid but not acetaminophen and the second interference component is caused by oxidation of ascorbic acid and not by oxidation of acetaminophen. In the foregoing sensor apparatus, when the first bias voltage is between 0.34 V and 0.45 V, the glucose-oxidation layer is configured to oxidize glucose, ascorbic acid and acetaminophen, and the first interference component is caused by oxidation of ascorbic acid and acetaminophen. When the second bias voltage is between 0.34 V and 0.45 V, the second electrode is configured to oxidize ascorbic acid and acetaminophen and the second interference component is caused by oxidation of both ascorbic acid and acetaminophen.

In the foregoing sensor apparatus, the first electrode may further comprise a maltose-blocking layer comprising polyphenylenediamine (poly-PD) formed on the glucose-oxidation layer. When contacting liquid containing glucose with a concentration of 4-20 mM (approximately 72-360 mg/dL) and when applying the bias voltage, the maltose-blocking layer is configured to let glucose pass therethrough and substantially block maltose from passing therethrough such that at steady state the glucose-oxidation current is at a level higher than 10 $nA/mMcm^2$ while a maltose oxidation current caused by oxidation of maltose alone is lower than 5 $nA/mMcm^2$.

The foregoing sensor apparatus may be a continuous glucose monitoring (CGM) electrode module comprising a subcutaneous portion configured to subcutaneously contact bodily fluid of a subject, wherein the first, second and reference electrodes are formed in the subcutaneous portion. In the foregoing sensor apparatus, the glucose-oxidation layer may comprise a nanoporous metal layer, wherein the first electrode further may comprise: an electrolyte ion-blocking layer formed over the nanoporous metal layer and a biocompatibility layer formed over the electrolyte ion-blocking layer. The electrolyte ion-blocking layer may be configured to inhibit $Na^+$, $K^+$, $Cl$, $PO_4^{3-}$ and $CO_3^{2-}$ contained in the liquid from diffusing toward the nanoporous metal layer such that there is a substantial discontinuity of a combined concentration of $Na^+$, $K^+$, $Ca^{2+}$, $Cl^-$, $PO_4^{3-}$ and $CO_3^{2-}$ between over the electrolyte ion-blocking layer and below the electrolyte ion-blocking layer.

In the foregoing sensor apparatus, the electrolyte ion-blocking layer may comprise a porous and hydrophobic polymer layer that is configured to limit mobility of Nat, $K^+$, $Ca^{2+}$, $Cl^-$, $PO_4^{3-}$ and $CO_3^{2-}$ therethrough while not limiting mobility of glucose molecules therethrough, wherein the electrolyte ion-blocking layer may comprise at least one selected from the group consisting of poly(methyl methacrylate) (PMMA), poly(hydroxyethyl methacrylate) (PHEMA), and poly(methyl methacrylate-co-ethylene glycol dimethacrylate) (PMMA-EG-PMMA).

In the foregoing sensor apparatus, the electrolyte ion-blocking layer may be configured to facilitate conditioning of the glucose-sensing electrode such that conditioning of the glucose-sensing electrode is complete within 30 minutes from contacting the subject's bodily fluid with the application of the bias voltage of 0.2-0.45 V, in which conditioning of the glucose-sensing electrode is considered as complete either or both of when a rate of decrease of the electric current is smaller than a first predetermined value and when the electric current stays smaller than a second predetermined value.

The foregoing sensor apparatus is a blood glucose monitoring (BGM) electrode module comprising a reservoir configured to receive blood, wherein when blood is received in the reservoir, the first, second and reference electrodes are configured to contact the blood. The first bias voltage is between 0.2 V and 0.45 V, wherein the second bias voltage is the same as or different from the first bias voltage. The glucose-oxidation layer may comprise a nanoporous metal material or a glucose-specific enzyme configured to oxidize glucose. The glucose-oxidation layer may comprise irregularly shaped bodies comprising a number of nanoparticles locally clustered together and interparticular gaps formed between adjacent ones of the nanoparticles in the irregularly shaped bodies, wherein the nanoparticles are generally in an oval or spherical shape having a diameter of about 2 nm to about 5 nm, wherein the interparticular gaps have an interparticular gap distance of about 0.5 nm to about 2 nm. Here, the irregularly shaped bodies may be interconnected to provide a three-dimensional interconnected network of irregularly shaped bodies. Irregularly shaped spaces may be formed between adjacent portions of the irregularly shaped bodies and are nano-sized or micro-sized, and the irregularly shaped spaces are interconnected to provide a three-dimensional interconnected network of irregularly shaped spaces.

Still another aspect of the invention provides a system comprising: the foregoing sensor apparatus that further comprises a terminal portion in which the first, second and third terminals are arranged; a counterpart apparatus comprising a first counterpart terminal, a second counterpart terminal, a third counterpart terminal, circuitry, and an electric power connected to the circuitry; and the counterpart apparatus further comprising a counterpart terminal portion configured to connect or engage with the terminal portion. Here, the first, second and third counterpart terminals are arranged in the counterpart terminal portion such that, when the terminal portion of the sensor apparatus and the counterpart terminal portion of the counterpart apparatus are connected or engaged, the first terminal electrically connects to the first counterpart terminal, the second terminal electrically connects to the second counterpart terminal, and the third terminal electrically connects to the third counterpart terminal. The circuitry of the counterpart apparatus is configured to provide the first bias voltage between the first counterpart terminal and the third counterpart terminal, and the circuitry of the counterpart apparatus is further configured to provide the second bias voltage between the second counterpart terminal and the third counterpart terminal.

In the foregoing system, the counterpart apparatus may comprise a wireless communication module configured to wirelessly communicate with a wirelessly paired computing device that comprises at least one processor and at least one memory. The counterpart apparatus may be configured to receive the first electric current at the first counterpart terminal and the second electric current at the second counterpart terminal. The counterpart apparatus may be configured to transmit the second electric current together or in connection with the first electric current when it transmits the first electric current. The first electric current may be transmitted with a first time stamp, and the second electric current may be transmitted with a second time stamp, wherein the first and second time stamps indicate an identical time.

The foregoing system may further comprise software installed and executable by the at least one processor of the wirelessly paired computing device. Upon execution, the software is configured to perform a method comprising: causing to store, in the at least one memory of the computing device, the first electric current and the second electric current received together or in connection with each other from the counterpart apparatus; processing the first electric current and the second electric current to provide a value indicative of the oxidation of glucose in the glucose-oxidation layer of the first electrode of the sensor apparatus; and causing to present the value or its corresponding information on a display of the computing device.

In the foregoing system, either or both of the first electric current and the second electric current may be in the form of continuous signals, wherein processing the first electric current and the second electric current may comprise processing values of the first electric current and the second electric current obtained at the same time. Here, processing values may comprise subtracting the second electric current from the first electric current. The first electric current and the second electric current may be stored in connection with each other in the at least one memory. The foregoing system may further comprise software installed and executable in the wirelessly paired computing device. Upon execution the software is configured to perform data processing to obtain a level of glucose contained in the liquid that the first electrode of the sensor apparatus contacts using the first electric current and the second electric current received from the counterpart apparatus. Here, the software requires the second electric current when processing to obtain the level of glucose.

In the foregoing system, the counterpart apparatus may further comprise at least one processor, at least one memory, and software stored in the at least one memory and executable by the at least one processor. Upon execution the software is configured to perform a method comprising: causing to store, in the at least one memory, the first electric current and the second electric current received together or in connection with each other from the sensor apparatus; and processing the first electric current and the second electric current to provide a value indicative of the oxidation of glucose in the glucose-oxidation layer of the first electrode of the sensor apparatus. Here, processing may comprise subtracting the second electric current from the first electric current. Either or both of the first electric current and the second electric current may be in the form of continuous signals, wherein processing the first electric current and the second electric current may comprise processing values of the first electric current and the second electric current obtained at the same time. The counterpart device may further comprise a display, wherein the method further may comprise causing to present the value or its corresponding information on the display. The counterpart device may further comprise a wireless communication module configured to wirelessly pair with a device that comprises a display, wherein the method may further comprise causing to transmit data to the wirelessly paired device for presenting the value or its corresponding information on the display of the wirelessly paired device.

Still another aspect of the invention provides a method of electrochemical sensing. The method comprises: providing a sensor apparatus comprising a first electrode that comprises a glucose-oxidation layer capable of oxidizing glucose, a second electrode that does not comprise a layer capable of oxidizing glucose, and a reference electrode; causing the first, second and reference electrodes to contact liquid containing glucose and ascorbic acid and acetaminophen; causing to apply a first bias voltage between the first and reference electrode that is sufficient to oxidize glucose in the glucose-oxidation layer such that glucose and at least one of ascorbic acid and acetaminophen are oxidized in the glucose-oxidation layer and further such that a first electric current is generated from the first electrode, wherein the first electric current comprises a glucose component caused by the glucose oxidation and a first interference component caused by oxidation of at least one of ascorbic acid and acetaminophen; causing to apply a second bias voltage between the second and reference electrodes such that at least one of ascorbic acid and acetaminophen is oxidized in the second electrode but glucose is not oxidized therein and further such that a second electric current is generated from the second electrode, wherein the second electric current comprises a second interference component caused by oxidation of at least one of ascorbic acid and acetaminophen in the second electrode; and providing the first electric current and the second electric current for processing, wherein when the first electric current is provided for processing, the second electric current also is provided in connection with the first electric current.

In the foregoing method, the first electric current and the second electric current may be generated at the same time or one after another within a reasonable period of time in which the glucose level does not change substantially or more than a predetermined tolerance level. The first electric current may be provided along with information indicative of time of generating the first electric current, wherein the second electric current may be provided along with information indicative of time of generating the second electric current. The second electric current may be provided together with the first electric current whenever the first electric current is provided. In the foregoing method, the first bias voltage is applied between 0.2 V and 0.32 V to cause the glucose-oxidation layer to oxidize glucoses and ascorbic acid but to not oxidize acetaminophen, in which the first interference component is caused by oxidation of ascorbic acid and not by oxidation of acetaminophen; the second bias voltage is applied between 0.2 V and 0.32 V to cause the second electrode to oxidize ascorbic acid but to not oxidize acetaminophen, in which the second interference component is caused by oxidation of ascorbic acid and not by oxidation of acetaminophen. In the alternative, the first bias voltage is applied between 0.34 V and 0.45 V to cause the glucose-oxidation layer to oxidize glucose, ascorbic acid and acetaminophen, in which the first interference component is caused by oxidation of ascorbic acid and acetaminophen; the second bias voltage is applied between 0.34 V and 0.45 V to cause the second electrode to oxidize ascorbic acid and acetaminophen, in which the second interference component is caused by oxidation of both ascorbic acid and acetaminophen.

In the foregoing method, the sensor apparatus may further comprise a maltose-blocking layer formed over the glucose-oxidation layer and comprising poly-phenylenediamine (poly-PD). The sensor apparatus may be a continuous glucose monitoring (CGM) electrode module comprising a subcutaneous portion configured to subcutaneously contact bodily fluid of a subject, wherein the first, second and reference electrodes are formed in the subcutaneous portion, wherein causing the first, second and reference electrodes to contact liquid may comprise subcutaneously inserting the subcutaneous portion into a subject's body. The glucose-oxidation layer may comprise a nanoporous metal layer, wherein the first electrode further may comprise: an electrolyte ion-blocking layer formed over the nanoporous metal layer and a biocompatibility layer formed over the electrolyte ion-blocking layer. The electrolyte ion-blocking layer inhibits $Na^+$, $K^+$, $Ca^{2+}$, $Cl^-$, $PO_4^{3-}$ and $CO_3^{2-}$ contained in the liquid from diffusing toward the nanoporous metal layer such that there is a substantial discontinuity of a combined concentration of $Na^+$, $K^+$, $Ca^{2+}$, $Cl^-$, $PO_4^{3-}$ and $CO_3^{2-}$ between over the electrolyte ion-blocking layer and below the electrolyte ion-blocking layer.

In the foregoing method, the sensor apparatus is a blood glucose monitoring (BGM) electrode module comprising a reservoir, wherein causing the first, second and reference electrodes to contact liquid may comprise providing a blood sample in the reservoir. The glucose-oxidation layer may comprise irregularly shaped bodies comprising a number of nanoparticles locally clustered together and interparticular gaps formed between adjacent ones of the nanoparticles in the irregularly shaped bodies, wherein the nanoparticles are generally in an oval or spherical shape having a diameter of about 2 nm to about 5 nm, wherein the interparticular gaps have an interparticular gap distance of about 0.5 nm to about 2 nm. The irregularly shaped bodies may be interconnected to provide a three-dimensional interconnected network of irregularly shaped bodies. Irregularly shaped spaces may be formed between adjacent portions of the irregularly shaped bodies and are nano-sized or micro-sized, and the irregularly shaped spaces may be interconnected to provide a three-dimensional interconnected network of irregularly shaped spaces.

In the foregoing method, the sensor apparatus may further comprise a first terminal electrically connected to the first electrode, a second terminal electrically connected to the second electrode, and a third terminal electrically connected to the reference electrode. The sensor apparatus may further comprise a terminal portion in which the first, second and third terminals are arranged, wherein causing to apply the first bias voltage and the second bias voltage may comprise connecting a counterpart device that comprises a first counterpart terminal, a second counterpart terminal, a third counterpart terminal, circuitry, and an electric power connected to the circuitry. The counterpart apparatus may further comprise a counterpart terminal portion for connecting or engaging with the terminal portion of the sensor apparatus. The first, second and third counterpart terminals may be arranged in the counterpart terminal portion such that, when the terminal portion of the sensor apparatus and the counterpart terminal portion of the counterpart apparatus are connected or engaged, the first terminal electrically connects to the first counterpart terminal, the second terminal electrically connects to the second counterpart terminal, and the third terminal electrically connects to the third counterpart terminal. The circuitry of the counterpart apparatus may provide the first bias voltage between the first counterpart terminal and the third counterpart terminal; the circuitry of the counterpart apparatus may provide the second bias voltage between the second counterpart terminal and the third counterpart terminal.

Still another aspect of the invention provides a method of providing or determining a glucose level. The method comprises: providing software stored in at least one memory and executable by at least one processor provided in the sensor apparatus or another device; executing, with the at least one processor, the software to process the first electric current and the second electric current to provide a value indicative of the oxidation of glucose in the glucose-oxidation layer of the first electrode of the sensor apparatus; and causing to present the value or its corresponding information on a display provided in the sensor apparatus, the other device or still another device.

In the foregoing method, the at least one memory and the at least one processor are provided in the other device. The method further may comprise: transmitting the first electric current and the second electric current to the other device; and prior to executing, causing to store, in the at least one memory, the first electric current and the second electric current received together or in connection with each other. In the foregoing method, the first electric current is transmitted with a first time stamp, and the second electric current is transmitted with a second time stamp, wherein the first and second time stamps indicate an identical time. In the foregoing method, either or both of the first electric current and the second electric current may be in the form of continuous signals, wherein processing the first electric current and the second electric current may comprise processing values of the first electric current and the second electric current obtained at the same time. In the foregoing method, processing may comprise subtracting the second electric current from the first electric current.

Still another aspect of the invention provides a sensor apparatus comprising: a working electrode comprising a nanoporous metal layer; and a reference electrode; and a bias voltage applied between the working electrode and the reference electrode, wherein no glucose-specific enzyme is present in the working electrode.

In the sensor apparatus, the nanoporous metal layer comprises irregularly shaped bodies comprising a number of nanoparticles locally clustered together and interparticular gaps formed between adjacent ones of the nanoparticles in the irregularly shaped bodies, and the nanoparticles are generally in an oval or spherical shape having a diameter of about 2 nm to about 5 nm, wherein the interparticular gaps have an interparticular gap distance of about 0.5 nm to about 2 nm. The irregularly shaped bodies may be interconnected to provide a three-dimensional interconnected network of irregularly shaped bodies. Irregularly shaped spaces are formed between adjacent portions of the irregularly shaped bodies and are nano-sized or micro-sized, and the irregularly shaped spaces are interconnected to provide a three-dimensional interconnected network of irregularly shaped spaces. In the sensor apparatus, the bias voltage is set to be sufficient to cause oxidation of glucose at the nanoporous metal layer but not sufficient to cause oxidation of acetaminophen at the nanoporous metal layer, wherein the bias voltage is set within a range between about 0.20 V and about 0.32 V.

The sensor apparatus may comprise a continuous glucose monitoring (CGM) electrode module comprising a subcutaneous portion configured to subcutaneously contact bodily fluid of a subject, wherein the working electrode and the reference electrode are formed in the subcutaneous portion. The working electrode may further comprise: an electrolyte ion-blocking layer formed over the nanoporous metal layer; and a biocompatibility layer formed over the electrolyte ion-blocking layer. The electrolyte ion-blocking layer may be configured to inhibit $Na^+$, $K^+$, $Ca^{2+}$, $Cl^-$, $PO_4^{3-}$ and $CO_3^{2-}$ contained in the liquid from diffusing toward the nanoporous metal layer such that there is a substantial discontinuity of a combined concentration of $Na^+$, $K^+$, $Ca^{2+}$, $Cl^-$, $PO_4^{3-}$ and $CO_3^{2-}$ between over the electrolyte ion-blocking layer and below the electrolyte ion-blocking layer. The electrolyte ion-blocking layer may be configured to facilitate conditioning of the working electrode such that conditioning of the working electrode is complete within 30 minutes from contacting the subject's bodily fluid with the application of the bias voltage.

The foregoing sensor apparatus may further comprise: a maltose-blocking layer comprising poly-phenylenediamine (poly-PD) and interposed between the nanoporous metal layer and the electrolyte ion-blocking layer. When contacting liquid containing maltose and glucose with a concentration of 4-20 mM (approximately 72-360 mg/dL) and when applying the bias voltage, the maltose-blocking layer is configured to let glucose pass therethrough and substantially block maltose from passing therethrough such that at steady state the glucose-oxidation current is at a level higher than 10 $nA/mMcm^2$ while a maltose oxidation current caused by oxidation of maltose alone is lower than 5 $nA/mMcm^2$.

Still another aspect of the invention provides a method of glucose sensing. The method comprises: providing one of the foregoing sensor apparatus; and applying a bias voltage between the working electrode (or glucose-sensing electrode) and the reference electrode within a range between about 0.20 V and about 0.32 V. Here, application of the bias voltage causes oxidation of glucose in the nanoporous metal layer such that a glucose-oxidation current caused by glucose oxidation alone is at a level higher than 10 $nA/mMcm^2$, whereas application of the bias voltage does not cause sufficient oxidation of acetaminophen in the nanoporous metal layer such that an acetaminophen oxidation current caused by acetaminophen oxidation in the nanoporous metal layer is lower than 5 $nA/mMcm^2$.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6B is a flowchart for making a clustered nanoporous layer according to another embodiment.

FIG. 8 illustrates a reverse micelle phase and a nanoparticle-surfactant colloid according to an embodiment.

FIGS. 17A-17C are SEM photographs of glucose-sensing working electrodes according to embodiments.

FIGS. 25-30 show electric currents monitored using glucose-sensing electrode with a maltose-blocking layer according to embodiments, in which the electric current signals are presented in color as they would not be easily seen in black and white.

DETAILED DESCRIPTION OF EMBODIMENTS

The presently disclosed subject matter now will be described and discussed in more detail in terms of some specific embodiments and examples with reference to the accompanying drawings, in which some, but not all embodiments of the invention are shown. Like numbers refer to like elements or parts throughout. The presently disclosed subject matter may be embodied in many different forms and should not be construed as limited to the specific embodiments set forth herein. Rather, these embodiments are provided so that this disclosure will satisfy applicable legal requirements. Indeed, many modifications and other embodiments of the presently disclosed subject matter will come to the mind of one skilled in the art to which the presently disclosed subject matter pertains. Therefore, it is to be understood that the presently disclosed subject matter is not to be limited to the specific embodiments disclosed and that modifications and other embodiments are intended to be included within the scope of the appended claims.

Electrochemical Glucose-Sensing System

Electrochemical Glucose Detection

Figure 1:
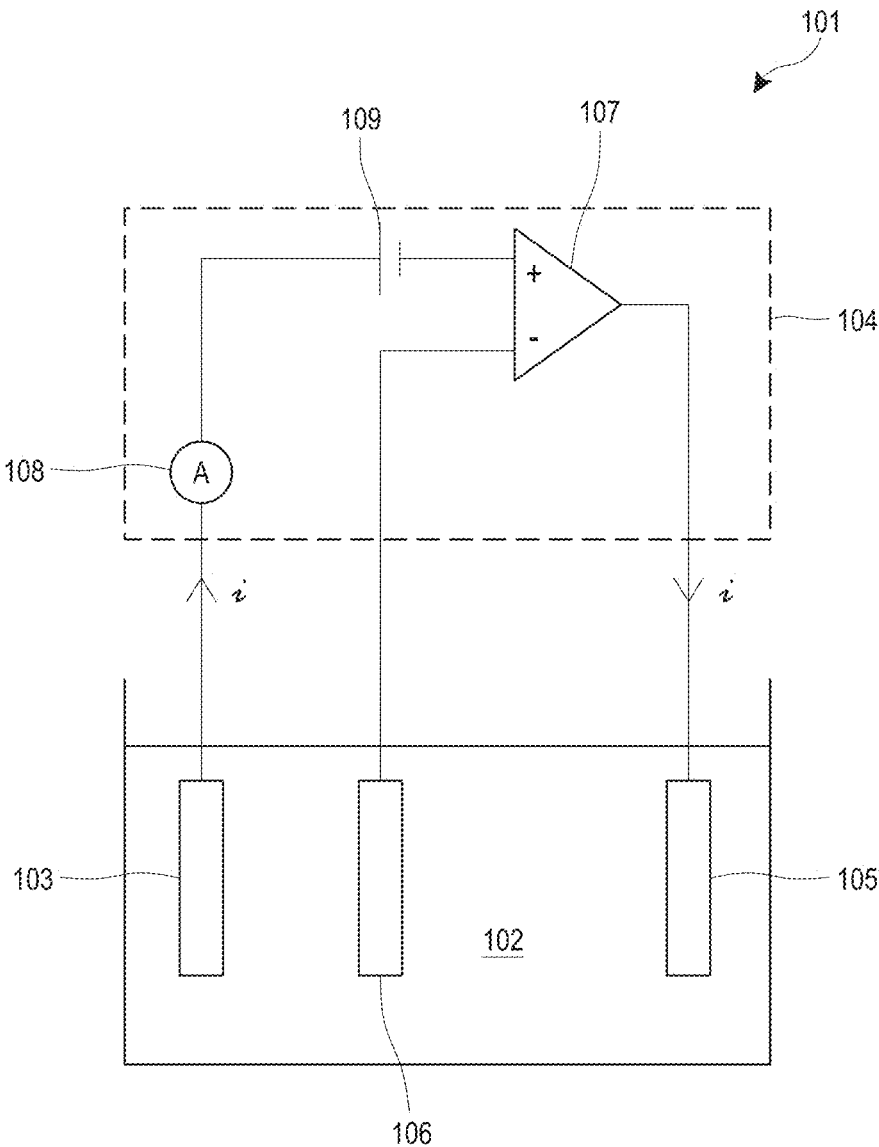
FIG. 1 illustrates a conceptual electrochemical glucose-sensing system according to embodiments of the invention.

Electrochemical glucose sensing measures glucose concentration in an electrolyte solution. FIG. 1 conceptually illustrates an electrochemical glucose-sensing system 101 for detecting a glucose concentration in a test fluid or electrolyte solution 102. The system 101 includes a working or sensing electrode 103, a counter electrode 105 and a reference electrode 106 that are connected to a potentiostat 104 and in contact with the test fluid 102. In embodiments, the potentiostat includes electric circuitry for functioning as a voltage source 109 and a current sensor 108. The voltage source 109 provides a bias voltage that drives redox reactions at the working electrode 103 and counter electrode 105. The potentiostat further includes an electric circuitry such as an op-amp 107 for maintaining the bias voltage at the working electrode 103 relative to the reference electrode 106. The current sensor 108 detects electric current generated by redox reactions involving glucose contained in the test fluid 102.

Enzymatic Glucose-Sensing Electrode

Figure 2:
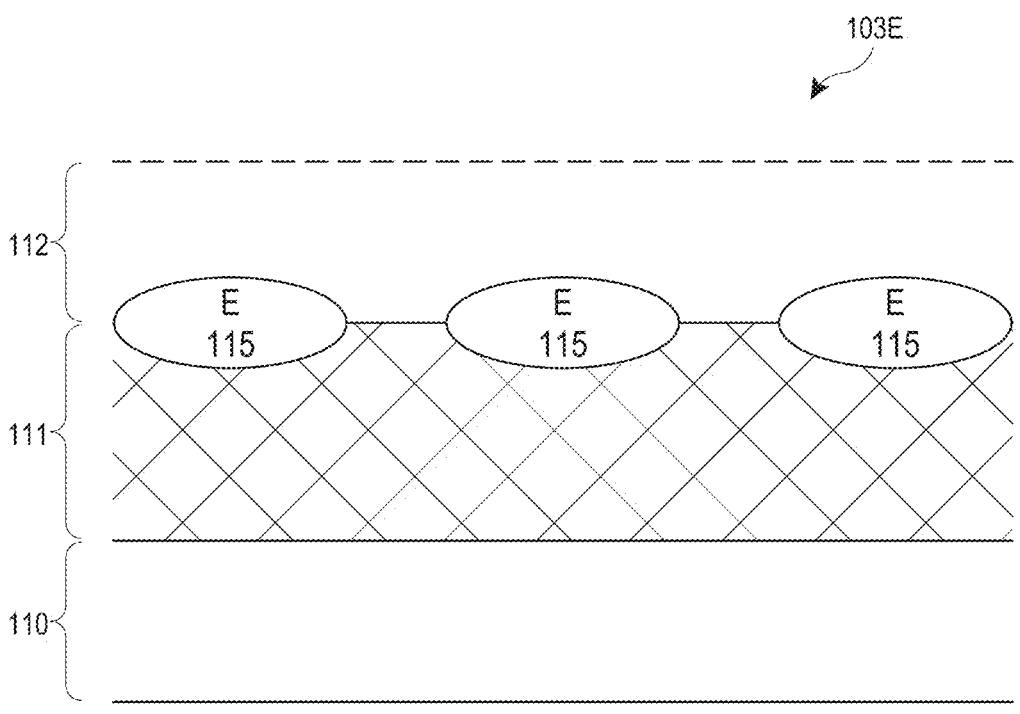
FIG. 2 illustrates a working electrode for an enzymatic glucose-sensing system according to an embodiment.

Most, if not all, electrochemical glucose-sensing systems utilize a glucose-specific enzyme for the detection of glucose molecules. FIG. 2 illustrates a working electrode 103E for an enzymatic glucose-sensing system, i.e., an enzymatic glucose-sensing electrode. The terms "glucose-sensing electrode" and "working electrode" are interchangeably used in the present disclosure. The enzymatic working electrode 103E includes a conductive layer 110 and an enzyme layer 111. Optionally, the enzymatic working electrode 103E may include at least one functional layer 112 over the enzyme layer 111 as in FIG. 2. Alternatively, although not illustrated, at least one functional layer may be located between the enzyme layer 111 and conductive layer 110. The enzyme layer 111 contains glucose-specific enzyme molecules 115, which are kept therein by an immobilizer 113. When glucose molecules contact the glucose-specific enzyme, the enzyme catalyzes oxidation of glucose to gluconolactone. Electrons from glucose oxidation are ultimately transferred to the conductive layer 110 for generating electric current in the electrical circuit of the electrochemical sensing system 101.

Glucose Oxidase

In some enzymatic glucose-sensing systems, the enzymatic working electrode 103E includes glucose oxidase (GOx). Glucose oxidase 115 transfers electrons to molecular oxygen staying near the enzyme, and the molecular oxygen is reduced to hydrogen peroxide. With a proper bias voltage applied in the system, the conductive layer 110 oxidizes hydrogen peroxide and takes electrons therefrom, which generates electric current indicative of the glucose concentration in the test fluid 102.

Glucose Dehydrogenase

In other enzymatic glucose-sensing systems, the enzymatic working electrode 103E includes glucose dehydrogenase (GDH). Unlike glucose oxidase, glucose dehydrogenase does not use oxygen and instead transfers electrons to other adjacent chemical entities referred to as electron mediator, which then transfers electrons from the glucose oxidation to the conductive layer 110. The electron mediator may be contained in the enzyme layer 111. Alternatively, the electron mediator may be provided in a separate layer (not shown) between the enzyme layer 111 and the conductive layer 110. While glucose dehydrogenase has some advantage of sensitivity over glucose oxidase, this enzyme oxidizes maltose as well as glucose, which interferes with accurate sensing of the glucose concentration.

Non-enzymatic Glucose-Sensing Electrode

Non-enzymatic electrochemical glucose-sensing systems do not use a glucose-specific enzyme or any enzyme for the detection glucose. Instead, non-enzymatic glucose-sensing systems have a non-enzymatic working electrode that detects glucose without a glucose-specific enzyme. In embodiments, the non-enzymatic working electrode includes at least one glucose oxidation layer that enables oxidation of glucose molecules at a moderate level of bias voltage. Generally, the higher the bias voltage, the more likely glucose oxidation occurs at the at least one glucose oxidation layer. However, because other chemical entities will also be oxidized at a high bias voltage, there is a limit for the bias voltage. Thus, non-enzymatic electrochemical glucose sensing relies on a material that oxidizes glucose at a bias voltage that does not cause oxidation of other chemical entities contained in the test fluid.

Nanoporous Layer for Non-Enzymatic Glucose-Sensing Electrode

Figure 3:
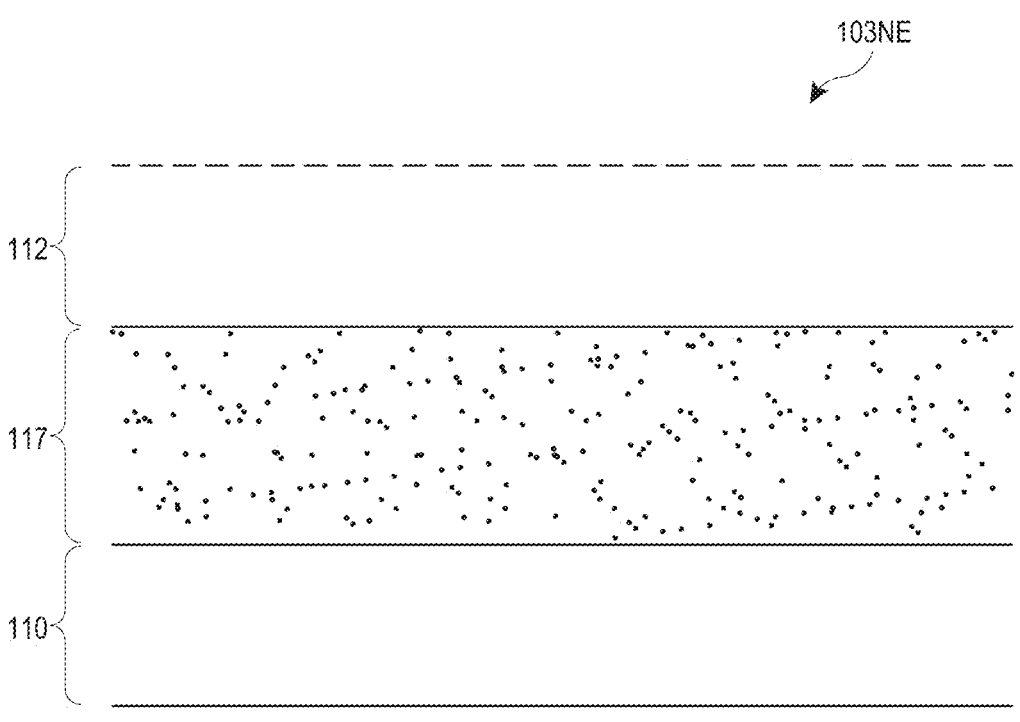
FIG. 3 illustrates a working electrode including a nanoporous layer for a non-enzymatic sensing system according to an embodiment.

FIG. 3 illustrates a non-enzymatic working electrode (simply "working electrode") 103NE that includes an electrically conductive layer 110 and a nanoporous glucose oxidation layer (or nanoporous layer) 117. In embodiments, the nanoporous layer 117 includes nanoporous internal structures for causing, enabling or facilitating oxidation of glucose at a moderate bias voltage. When glucose oxidation occurs, the conductive layer 110 takes electrons from glucose oxidation and electrical current is generated in the electrical circuit. The electrical current can be detected by the current sensor 108 and interpreted by hardware and software of the system. Optionally, the working electrode 103NE may include at least one functional layer 112 over the nanoporous layer 117 or between the nanoporous layer 117 and conductive layer 110 (not shown).

Conductive Layer—Materials

With the bias voltage, the conductive layer 110 of FIGS. 2 and 3 takes electrons from glucose oxidation and transfers them to the current sensor 108. In embodiments, the conductive layer 110 includes or is made of at least one electrically conductive material and is connected to electrical circuit of the system 101. In some embodiments, given the small scale of the conductive layer 110, semiconductive materials may be used instead of electrically conductive material. Non-limiting examples for a material of the conductive layer includes platinum (Pt), gold (Au), silver (Ag), ruthenium (Ru), stainless steel, silicon (amorphous, poly and single crystalline), conductive carbon materials, including graphite, graphene, fluorene, carbon nanotubes. In the embodiments, the conductive layer 110 does not include nanoporous internal structures of the glucose oxidation layer 117.

Conductive Layer—Configurations

In embodiments, the conductive layer 110 may be formed of a single layer of a homogeneous material. In the alternative, the conductive layer 110 may include multiple sublayers made of different materials. In some embodiments, the conductive layer 110 includes top sublayer and one or more sublayers under the top sublayer. In embodiments, the top sublayer does not contain silver, copper, aluminum or other conductive materials that are prone to oxidation more than silver, copper or aluminum. The top sublayer may be less electrically conductive than the other sublayer(s). In some embodiments, the conductive layer 110 includes a conductive carbon layer as the top sublayer and a silver layer as another sublayer under the carbon layer. The conductive layer 110 has a thickness that can vary significantly depending upon particular examples. In some embodiments, the conductive layer 110 may be omitted, and the nanoporous layer is directly connected to the current sensor via an electrically conductive wire or connection.

Counter Electrode

With the bias voltage, reduction of a chemical entity occurs at the counter electrode 105. In embodiments, the counter electrode 105 includes at least one electrically conductive or semiconductive material and is connected to electrical circuit of the system 101. In embodiments, the counter electrode 105 may be formed of a single layer of a homogenous material or multiple layers made of different materials. The conductive or semiconductive materials for the conductive layer 110 may also be used in the counter electrode 105 although not the same materials are used in the conductive layer 110 and in the counter electrode 105 in a particular system.

Reference Electrode

The reference electrode 106 provides stability in the electrochemical sensing system by maintaining the bias voltage between the sensing electrode 103 and the reference electrode. As a result, glucose oxidation can continue at the sensing electrode 103 even if reduction at the counter electrode 105 is not at the same rate as the oxidation at the sensing electrode 103. In some embodiments, the counter electrode 105 may be omitted, and the reference electrode 106 may serve dual functions of the counter and reference electrodes. In embodiments, the reference electrode 106 may be formed of a single layer of a homogenous material or multiple layers made of different materials. The conductive or semiconductive materials for the conductive layer 110 may also be used in the reference electrode 105 although not the same materials are used in the conductive layer 110 and in the reference electrode 106 in a particular system. In some embodiments, the reference electrode 106 may include a salt layer over the conductive or semiconductive material layer. For example, the salt layer is made of or includes silver chloride (AgCl).

Current Sensor

The current sensor 108 measures electric current flowing from the working electrode 103. The current sensor 108 may amperometrically detect electric current flowing at a specific point in time. In the alternative, the current sensor 108 may be a coulometric charge-measuring device.

Test Fluid

In embodiments, the test fluid is a biological fluid of human or animal, although not limited thereto. In some embodiments, the test fluid is a liquid mixture including a biological fluid and at least one additional substance added to the biological fluid. The biological fluid includes, for example, blood, interstitial fluid, cerebral spinal fluid, lymph fluid or urine, although not limited thereto. In some embodiments, the test fluid includes a non-biological liquid prepared for experiments.

Bias Voltage

The bias voltage applied between the working electrode 103NE and reference electrode 106 is at or about 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45 or 0.46 V. In embodiments, the bias voltage applied may be within a range formed by selecting any two numbers (two voltage values) listed in the immediately previous sentence, e.g., between about 0.20 V and about 0.30 V, between about 0.30 V and about 0.40 V, between about 0.28

V and about 0.40 V, between about 0.30 V and about 0.38 V, between about 0.28 V and about 0.36 V, etc.

Nanoporous Layer

Nanoporous Layer

The nanoporous layer 117 for the working electrode 103NE includes nano-size internal structures such as cavities, spaces and openings (collectively "nano-pores" or "nanopores"). In embodiments, nanopores of the nanoporous layer 117 enable or facilitate oxidation of glucose, and glucose concentration can be measured based on electric current caused by glucose oxidation. Although any aspects of the invention are not bound by any theory or belief, it is conceivable that glucose oxidation occurs when glucose molecules enter nanopores and contact internal surfaces more often and for a longer time in the nanoporous layer 117 than on a non-porous surface of an electrode.

No Enzyme and No Electron Mediator

With the incorporation of the nanoporous layer 117, the working electrode 103NE can be provided without a glucose-specific enzyme that requires more complex fabrication processes and is less stable than the solid-state material of the nanoporous layer 117. Further, the enzymatic sensing electrodes 103NE can operate without an electron mediator that facilitates electron transfers between different materials. In embodiments, the working electrode 103NE includes neither an enzyme nor an electron mediator.

Materials for Nanoporous Layer

In some embodiments, the nanoporous layer 117 is made of or includes platinum (Pt), gold (Au), palladium (Pd), rhodium (Rh), titanium (Ti), ruthenium (Ru), tin (Sn), nickel (Ni), copper (Cu), indium (In), thallium (Tl), zirconium (Zr), iridium (Ir), or an oxide of the foregoing elements, although not limited thereto. In other embodiments, the nanoporous layer 117 is made of or includes an alloy material of two or more of the metal elements listed in the previous sentence including Pt—Ir, Pt—Ru, Pt—Pd, although not limited thereto.

Roughness Factor Defined

Figure 4:
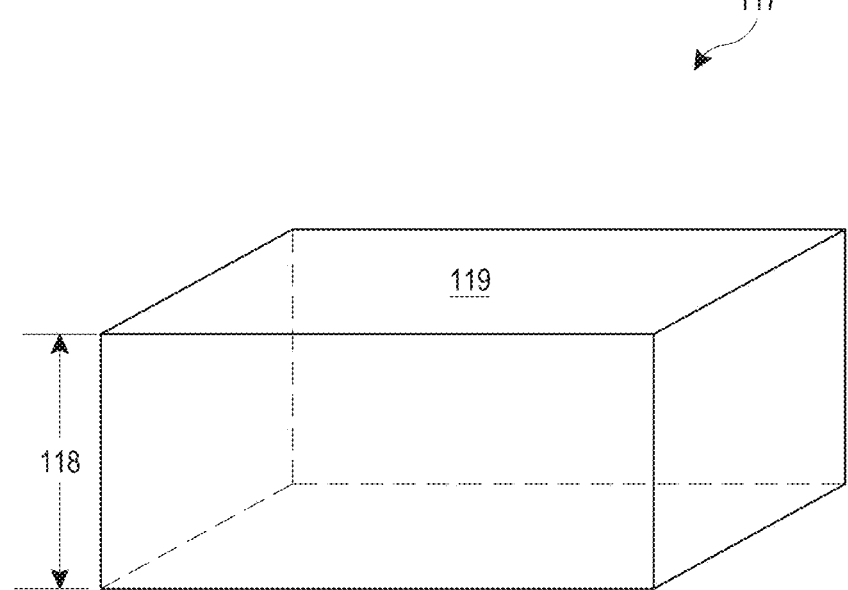
FIG. 4 illustrates a nanoporous layer's top surface and depth.

Roughness factor or rugosity is a ratio of a real surface area to a geometric surface area of an object. Here, the geometric surface area refers to a projected area of the object that is projected onto a flat surface without considering internal surfaces within the object. The real surface area refers to the total area of surfaces considering internal surfaces. Referring to FIG. 4, for example, if the nanoporous layer 117 is in a rectangular block having a height or depth 118 and a top rectangle 119, the projected area or geometric surface area of the nanoporous layer is the area of the top rectangle that is exposed to outside. The real surface area of a nanoporous layer may be electrochemically measured, for example, using a well-known cyclic voltammetric technique that detects electric current from proton adsorption on the real surface.

Roughness Factor of Nanoporous Layer

The roughness factor value indicates the total amount of internal pores within the nanoporous layer 117. The roughness factor of the nanoporous layer 117 may relate to the sensitivity of the nanoporous layer 117 for the glucose oxidation. Generally the higher the roughness factor, the more glucose oxidation may occur. The roughness factor of the nanoporous layer 117 is at or about 100, 200, 300, 400, 500, 600, 700, 800, 900, 100, 1100, 1200, 1300, 1400, 1500, 1600, 1700, 1800, 1900, 2000, 2100, 2200, 2300, 2400 or 2500. In embodiments, the roughness factor may be within a range formed by selecting any two numbers (two roughness factor values) listed in the immediately previous sentence, e.g., between about 100 and about 2500, between about 750 and about 1250, or between about 850 and about 1150.

Thickness of Nanoporous Layer

The roughness factor value does not indicate the level of porosity or density of the nanoporous material in its unit volume while the value may indicate the total amount of internal pores. Thus, depending upon the level of porosity of the nanoporous material, in embodiments, thickness of the nanoporous layer may be adjusted to achieve a target value for the roughness factor. In embodiments, the thickness of nanoporous layer 117 may be about 0.03, 0.05, 0.1, 0.5, 1, 2, 3, 4, 5, 6, 7, 8, 9 and 10 μm. In some embodiments, the thickness may be within a range formed by selecting any two numbers (two thickness values) listed in the immediately previous sentence, e.g., between about 0.05 μm (50 nm) and about 10 between about 0.5 μm and about 8 μm, or between about 2 μm and about 7 μm.

Morphologies

The nanoporous layer 117 may have different internal morphologies in each specific manufacture. In some embodiments, the nanoporous layer 117 may include or be made of nanoparticles deposited together forming nanopores among themselves (interparticular nanopores). In other embodiments, the nanoporous layer 117 may include or be made of clusters of nanoparticles deposited together that form interparticular nanopores within a cluster and also spaces among clusters (intercluster gaps or spaces). In other embodiments, the nanoporous layer 117 may include or be made of repetition of a specific shape of nanostructure such as hexagonal structure that includes nanopores therein. Also, in each specific manufacture, the nanoporous layer 117 may have different levels of porosity and different roughness factor values per unit volume.

Making Nanoporous Layer

The nanoporous layer 117 may be prepared using a liquid composition that contains metal ions and a surfactant. In embodiments, different morphologies of the nanoporous layer may be formed using different phases of the surfactant. A micelle phase, a reverse micelle phase, a liquid crystalline phase or another phase of the surfactant may be used to produce the nanoporous layer in a particular morphology. In these different phases, the metal ions are aligned or locally concentrated next to hydrophilic moieties of the surfactant. The localized metal ions in the liquid composition are subject to additional processes for reduction and deposition on a surface to provide a nanoporous layer 117 having different morphologies.

Clustered Nanoporous Layer

Clustered Morphology

Figure 5A:
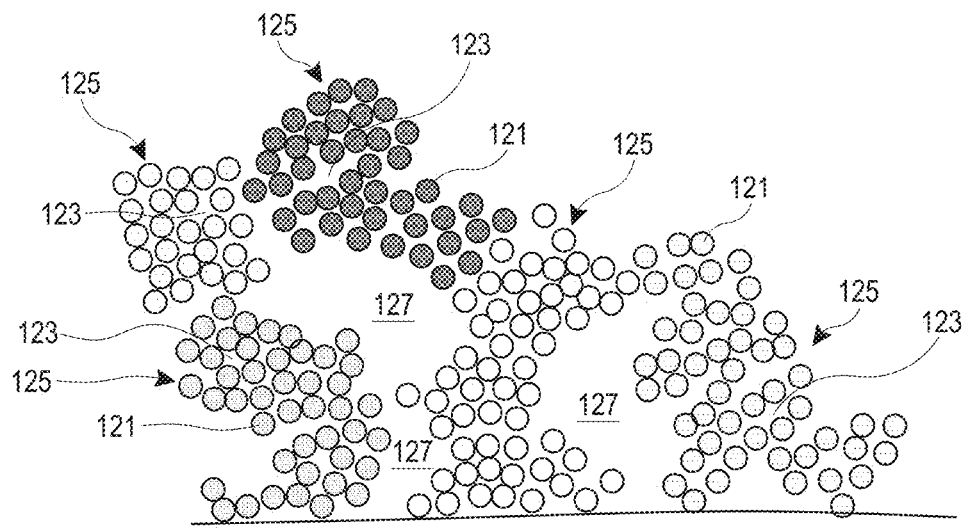
FIG. 5A illustrates a clustered morphology of a nanoporous layer according to an embodiment.
Figure 5B:
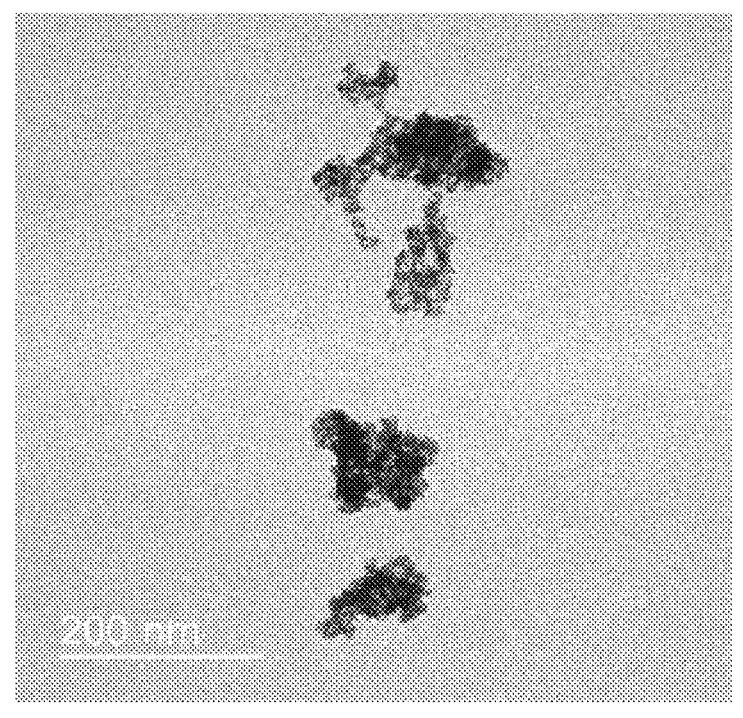
FIG. 5B is a TEM photographic image of clusters according to an embodiment.
Figure 5C:
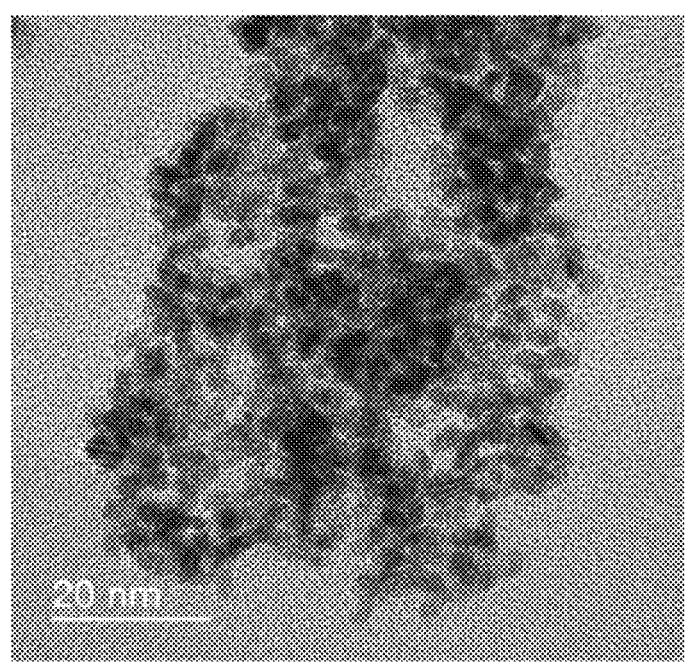
FIG. 5C is a zoomed-in image of the TEM photographic image of FIG. 5B.
Figure 5D:
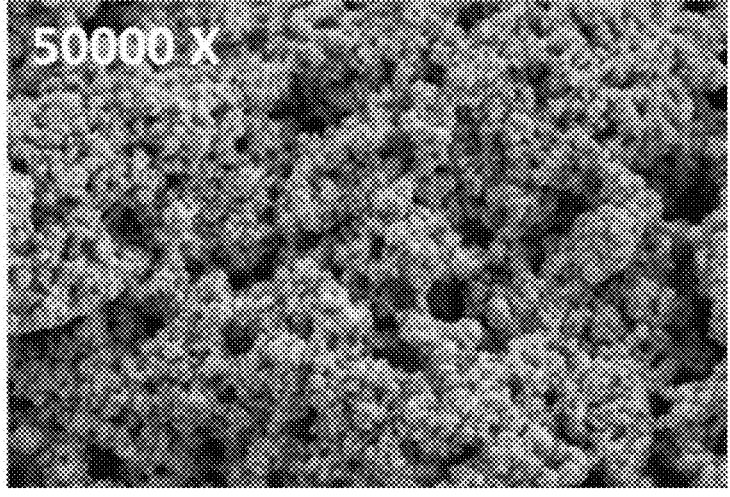
FIG. 5D is an SEM photographic image of a nanoporous layer taken from its top according to an embodiment.

FIG. 5A is an illustration of a vertical cross-section of nanoporous layer having a clustered morphology 120 over a substrate 129. In nano-sized reality, the top surface of the substrate 129 may not be as straight as illustrated and may be bumpy. In the clustered morphology 120, a number of nanoparticles 121 get together and form irregularly shaped clusters 125. For the sake of illustration, different shadings or hatchings are used in different clusters 125. These irregularly shaped clusters 125 are stacked irregularly to form the nanoporous layer. FIG. 5B is a transmission electron microscope (TEM) photographic image of some clusters 125 before they deposit to form a nanoporous layer. FIG. 5C is a zoomed-in image of the circled portion of FIG. 5B. FIG. 5D is a scanning electron microscope (SEM) photographic image of a nanoporous layer having a clustered morphology taken from the top of the nanoporous layer.

Pores and Spaces of Clustered Morphology

With irregular stacking of irregularly shaped clusters 125, neighboring clusters form intercluster gaps or spaces 127 between them. These intercluster gaps 127 may be nano-sized and micro-sized. In this disclosure, nano-size means greater than 1 nm and smaller than 100 nm, and micro-size means greater than 100 nm and smaller than 100 μm. Each cluster 125 includes or is made of generally spherical or oval nanoparticles 121. In each cluster, individual nanoparticles are generally separate from one another and form small gaps 123 therebetween. The small gaps are nano-sized and referred to as interparticular nanopores 123. In embodiments, interparticular nanopores are found throughout the clusters. In embodiments, interparticular nanopores form interconnected or networked channels within each cluster. FIGS. 5A and 5D show these interparticular nanopores 123 in each cluster 125.

Forming Intercluster Gaps/Spaces

In embodiments, to produce a clustered morphology, irregularly shaped clusters 125 are first prepared as suspension in liquid. Then, the suspension is dispensed on the substrate 129, which is subject to drying. As the liquid dries off, clusters are spontaneously deposited over the substrate and over other clusters. No external force may be applied to the clusters while drying. Accordingly, the clusters do not get packed as they deposit. As clusters deposit and stack over other clusters, each cluster may contact the substrate surface or neighboring clusters. After completion of drying, the clusters abut or contact adjacent or neighboring clusters. The deposited clusters are interconnected or integrated via the abutments and contacts. Due to the irregular shapes of individual clusters, irregularly shaped gaps and spaces are formed between adjacent clusters, in which the gaps and spaces define the irregular shapes of the deposited clusters as if the surfaces and contours of deposited clusters are surrounded by the irregularly shaped gaps and spaces. The irregularly shaped gaps and spaces are referred to as intercluster gaps or spaces 127.

Distribution of Clusters and Intercluster Gaps

In embodiments, the irregularly shaped cluster bodies 125 are distributed throughout the clustered morphology 120 of the nanoporous layer 117. The irregularly shaped cluster bodies 125 are interconnected via abutments, which means these cluster bodies contact themselves and form a three-dimensional network of cluster bodies generally throughout the nanoporous layer 117. The intercluster gaps 127 define and surround surfaces of the irregularly shaped cluster bodies and are interconnected themselves to form a three-dimensional interconnected or networked channels throughout the nanoporous layer 117. The intercluster gaps and spaces 127 are well distributed throughout the nanoporous layer 117 from the top (not shown) to the bottom (on or immediately above the substrate 129). The three-dimensional network of irregularly shaped clustered bodies and the three-dimensional network of irregularly shaped gaps three-dimensionally are complementary to form a highly networked three-dimensional mesh structure. The three-dimensional network of cluster bodies and channels may be similar to the three-dimensional internal shapes of a sponge except that the interparticular gaps and spaces are networked together throughout the nanoporous layer 117.

Distribution of Nanoparticles and Interparticular Nanopores

Given that each cluster is formed with many nanoparticles 121 and interparticular nanopores 123, the nanoparticles 121 and interparticular nanopores 123 are distributed generally throughout the nanoporous layer 117. Accordingly, interparticular nanopores 123 are interconnected within each cluster and interconnected with interparticular nanopores of other clusters generally throughout the nanoporous layer 117 via interparticular nanopores in abutments between clusters and via intercluster gaps 127 that are interconnected throughout the nanoporous layer 117.

Intercluster Gaps/Spaces for Diffusion of Glucose

In embodiments, the interconnection of intercluster gaps 127 provides networked channels for diffusion of glucose molecules (0.7-0.8 nm long) within the nanoporous layer 117. It is understood that glucose oxidation occurs primarily in nano-sized interparticular nanopores rather than in micro-sized spaces. As the intercluster gaps 127 are networked or interconnected throughout the nanoporous layer 117, glucose molecules may reach almost anywhere in the nanoporous layer 117 via the intercluster spaces that are large scale considering the size of glucose molecules. Also, as the intercluster gaps 127 are well interconnected to the interparticular nanopores 123, interparticular nanopores 123 anywhere in the nanoporous layer 117 may be exposed and open for glucose oxidation. Accordingly, the three-dimensional interconnected or networked channels of the intercluster gaps may provide more glucose oxidation, i.e., stronger signals (higher electric current) of the glucose oxidation than a nanoporous layer without such interconnected channels formed of intercluster gaps.

Two Types of Particles and Two Types of Pores

As discussed, the clustered morphology 120 includes two different types of particles defining two different types of pores. In terms of particles, one is the nanoparticles 121, and the other is the clusters 125 made of nanoparticles 121. In terms of pores, one is the interparticular nanopores 123 between nanoparticles 121 within a cluster 125, and the other is the intercluster gaps 127 between clusters 125.

Clusters of Nanoparticles

The TEM photographic image of FIG. 5B shows clusters in irregular shapes. The number of nanoparticles 121 in each cluster may vary wildly, and the size of clusters 125 may vary accordingly. In clustered morphologies, some clusters 125 are nano-sized (smaller than 100 nm), and others are micro-sized (100 nm to 100 μm). The clusters 125 have a length or diameter of about 20, 40, 60, 80, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680 or 700 nm. In embodiments, the length or diameter of the clusters 125 may be within a range formed by selecting any two numbers (two length or diameter values) listed in the immediately previous sentence, e.g., between about 20 nm and about 300 nm, or between about 60 nm and about 240 nm. The clusters 125 may have a mean diameter or length of about 50, 60, 70, 80, 90, 100, 110, 120, 130, 140, 150, 160, 170, 180, 190, 200, 210, 220, 230, 240, 250, 260, 280 or 300 nm. In embodiments, the mean diameter of the clusters 125 may be within a range formed by selecting any two numbers listed in the immediately previous sentence, e.g., between about 100 nm and about 220 nm.

Nanoparticles

The TEM photographic image of FIG. 5C shows nanoparticles in a single cluster. The nanoparticles 121 in the cluster are discrete and generally in a spherical (ball-like) or oval (egg-like) shape, although not limited thereto. The nanoparticles 121 have a diameter of about 1.0, 1.5, 2.0, 2.5, 3.0, 3.5, 4.0, 4.5, 5.0, 5.5, 6.0, or 6.5. In embodiments, the diameter may be within a range formed by selecting any two numbers (two diameter values) listed in the immediately previous sentence, e.g., between about 2 nm and about 5 nm. The nanoparticles 121 may have a mean diameter of about 2.0, 2.25, 2.5, 2.75, 3.0, 3.25, 3.5, 3.75 or 4.0. In embodiments, the mean diameter of the nanoparticles 121 may be within a range formed by selecting any two numbers listed in the immediately previous sentence, e.g., between about 2.5 nm and about 4.0 nm, between about 2.75 nm and about 3.75 nm, or between about 2.25 nm and about 3.5 nm. In embodiments, nanoparticles having a mean diameter of 2-5 nm are found throughout the nanoporous layer 117.

Interparticular Nanopores

The TEM photographic image of FIG. 5C also shows interparticular nanopores between nanoparticles in the cluster. The interparticular nanopores are networked and interconnected within the cluster. The interparticular gaps or nanopores 123 have an interparticular gap distance between two immediately neighboring nanoparticles within the same cluster. The interparticular gap distance is about 0.25, 0.5, 0.75, 1.0, 1.25, 1.5, 1.75, 2.0, 2.5, 3.0, 3.5, 4.0 or 4.5 nm. In embodiments, the interparticular gap distance may be within a range formed by selecting any two numbers (two distance values) listed in the immediately previous sentence, e.g., between about 0.5 nm and about 4.5 nm, or between about 1.5 nm and about 4.0 nm. The interparticular nanopores 123 may have a mean interparticular gap distance of about 0.5, 0.75, 1.0, 1.25, 1.5, 1.75, 2.0, 2.25, 2.5, 2.75, 3.0 or 3.5 nm. In embodiments, the mean interparticular gap distance of the nanopores 123 may be within a range formed by selecting any two numbers listed in the immediately previous sentence, e.g., between about 0.75 nm and about 1.5 nm, or between about 1.0 nm and about 2.5 nm. In embodiments, interparticular nanopores 123 having a mean interparticular gap distance of 1-2.5 nm are found throughout the nanoporous layer 117.

Intercluster Gaps/Spaces

The SEM photographic image of FIG. 5D shows openings of the networked intercluster gaps that can be seen from the top of the nanoporous layer. Although the three-dimensional shapes are not well presented in the two-dimensional image of FIG. 5D, the top surface of nanoporous layer includes valleys and hills formed by stacked clusters. Inside the nanoporous layer, the valleys and hills form the intercluster gaps. The intercluster gaps or spaces are in irregular shapes. The intercluster gaps 127 are nano-sized to micro-sized. The intercluster gaps 127 have an intercluster gap distance of about 25, 50, 75, 100, 125, 150, 175, 200, 225, 250, 275, 300, 325, 350, 375, 400, 425, 450, 475, 500, 525, 550, 575, 600, 625, 650, 675 or 700 nm. In embodiments, the intercluster gap distance may be within a range formed by selecting any two numbers listed in the immediately previous sentence, e.g., between about 100 nm and about 1000 nm. The intercluster gaps 127 have a mean intercluster gap distance of about 100, 150, 200, 250, 300, 350, 400, 450 or 500 nm. In embodiments, the mean intercluster gap distance may be within a range formed by selecting any two numbers listed in the immediately previous sentence, e.g., between about 150 nm and about 400 nm.

Making Clustered Nanoporous Layer

Overall Process

Figure 6A:
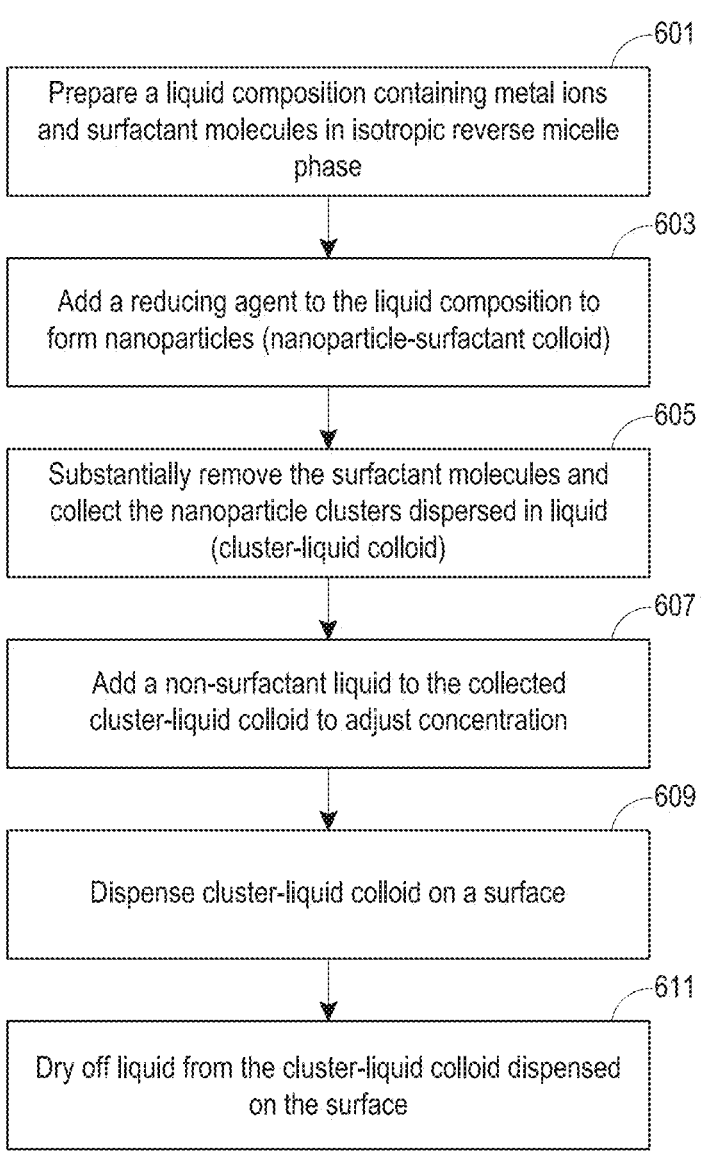
FIG. 6A is a flowchart for making a clustered nanoporous layer according to an embodiment.

In embodiments, a nanoporous layer having a clustered morphology may be prepared using an isotropic reverse micelle phase (or "reverse micelle phase")" of a surfactant. Referring to FIG. 6A, at step 601, an aqueous liquid composition is prepared with a metal ion source and a surfactant in a reverse micelle phase. The metal ions are locally concentrated within hydrophilic spaces of individual reverse micelles. Subsequently at step 603, a reducing agent is added to the reverse micelle phase to form metal nanoparticles dispersed in the liquid composition containing the surfactant ("nanoparticle colloid" or "nanoparticle-surfactant colloid"). Subsequently at step 605, the surfactant is removed from the nanoparticle-surfactant colloid, and the nanoparticle clusters dispersed in liquid ("cluster colloid" or "cluster-liquid colloid") are collected. Optionally at step 607, the collected cluster colloid is mixed with a non-surfactant liquid. At step 609, the cluster colloid is dispensed onto a surface, for example, by printing technique without use of electroplating. Subsequently at step 611, the liquid is dried off to form a nanoporous layer 117 on the surface 129.

Surfactant

Figure 7:
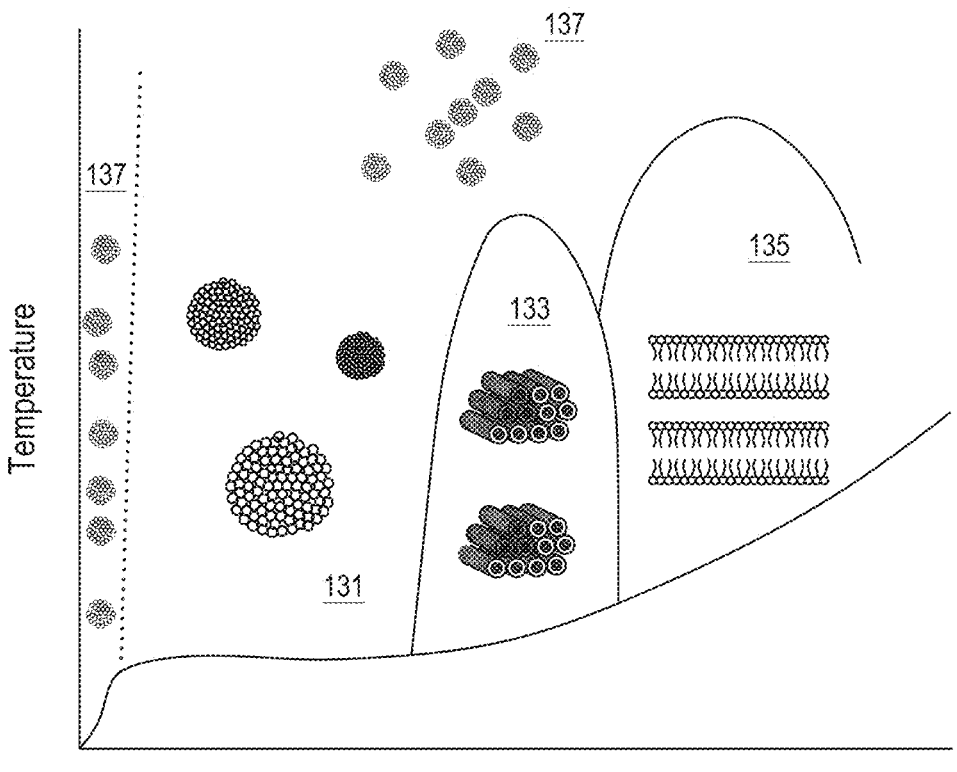
FIG. 7 is an example phase diagram of a surfactant showing different phases.

Surfactants are amphiphilic organic compounds having a hydrophilic head (or hydrophilic moiety) and a hydrophobic tail (hydrophobic moiety) in a single molecule. Surfactants may form different structures or phases in water depending on the concentration and temperature. FIG. 7 is an example phase diagram of a surfactant showing different phases including micelle phase 131, hexagonal phase 133, Lamellae phase 135, and two micelles phases 137.

Preparing Isotropic Reverse Micelle Phase

At step 601, an isotropic reverse micelle phase is prepared with an aqueous liquid composition containing a surfactant, metal ions and water. As in the conceptual illustration of FIG. 8, the reverse micelle phase includes reverse micelles 141 formed by the surfactant molecules. Each reverse micelle 141 includes a hydrophilic core 143 surrounded by hydrophobic tails radiating from the hydrophilic core. The hydrophilic core 143 encloses hydrophilic components of the liquid composition, i.e., water and metal ions. Thus, the metal ions are locally concentrated within the hydrophilic core 143 of reverse micelles.

Surfactant Examples

The surfactant is chosen from those that can form an isotropic reverse micelle phase under reasonable conditions for processing. In some embodiments, a non-ionic surfactant is used, although not limited thereto. Non-limiting examples of the surfactant include alkylbenzenesulphonates, alkylpolyglycoside, alkyl sulphates, carboxylates, carboxylic esters, Cetomacrogol 1000™, cetostearyl alcohol, cetyl alcohol, cocamide DEA, cocamide MEA, decyl glucoside, decyl polyglucose, disodium cocoamphodiacetate, ethoxylated aliphatic alcohol, glycerol monostearate, glycol esters of fatty acids, IGEPAL CA-630™, isoceteth-20, lauryl glucoside, maltosides, monolaurin, mycosubtilin, naphthalenesulphonates, narrow-range ethoxylate, Nonidet P-40™, nonoxynol-9, nonoxynols, NP-40™, octaethylene glycol monododecyl ether, N-Octyl beta-D-thioglucopyranoside, octyl glucoside, oleyl alcohol, PEG-10 sunflower glycerides, pentaethylene glycol monododecyl ether, polidocanol, poloxamer, poloxamer 407, polyethoxylated tallow amine, polyethylene glycol esters, polyglycerol polyricinoleate, polyoxyethylene fatty acid amides, polyoxyethylene surfactants, polysorbate, polysorbate 20, polysorbate 80, sorbitan, sorbitan monolaurate, sorbitan monostearate, sorbitan tristearate, stearyl alcohol, surfactin, sulphated alkanolamides, sulphonates, Triton X-100™, and Tween 80™ A skilled artisan in the relevant field would appreciate what would constitute the reasonable conditions.

Conditions for Reverse Micelle Phase

Subsequent to choosing the surfactant, its concentration and the temperature are adjusted to form an isotropic reverse micelle phase. The surfactant's concentration and temperature may be determined with reference to the surfactant's phase diagram. When the phase diagram is not available, some experiments for finding appropriate concentration and temperature may be necessary using known laboratory techniques and procedures. For example, when Triton X-100™ is used for the surfactant, the concentration of 10-60 wt % and temperature of 40-80° C. may provide the reverse micelle phase.

Source of Metal Ions

One or more metal ions corresponding to the metal or alloy for the nanoporous layer are chosen for the liquid composition. The metal ions are added in the form of a compound containing the ionic metal such as an acid, base or salt. Non-limiting examples of the metal source compound include $H_2PtCl_6$, $H_2Pt(OH)_6$, $H_2PtCl_2(OH)_4$, $H_2Pt(SO_4)(OH)_4$, $PtCl_4$, $K_2PtCl_6$, $PdCl_2$, and $TiCl_4$.

Concentration of Metal Ions

The concentration of metal ions is also adjusted for best performance. When the concentration is too low, nanoparticles may not be formed. When the concentration is too high, it may affect the formation or stability of the reverse micelle phase of the surfactant. The concentration of metal ions is about 0.001, 0.002, 0.003, 0.004, 0.005, 0.006, 0.007, 0.008, 0.009, 0.01, 0.012, 0.014, 0.016, 0.018, 0.02, 0.022, 0.024, 0.026, 0.028, 0.03, 0.032, 0.034, 0.036, 0.038, 0.04, 0.042, 0.044, 0.046, 0.048, 0.05, 0.055, 0.06, 0.065, 0.07, 0.075, 0.08, 0.085, 0.09, 0.095 or 0.1 M. In embodiments, the concentration may be within a range formed by selecting any two numbers (two molarity values) listed in the immediately previous sentence, e.g., between about 0.01 and about 0.03 M, between about 0.02 and 0.03 M, etc. Within an appropriate concentration range, it has been observed that the level of concentration affects the speed of formation of nanoparticles.

Different from Plating Bath

The reverse micelle phase prepared at step 601 is not a plating bath composition for electroplating. Unlike in the plating bath, no metal chelating agent may be needed.

Forming Nanoparticles

At step 603, a reducing agent is mixed to the aqueous liquid composition in the reverse micelle phase. When the reducing agent enters the hydrophilic core 143 of reverse micelles 141, it reduces metal ions to metal atoms inside the hydrophilic core 143. Because the metal ions are locally concentrated inside the hydrophilic cores 143, initially metal atoms remain inside the hydrophilic cores 143. The metal atoms inside each hydrophilic core 143 coagulate together and grow to form metal nanoparticles. One metal nanoparticle may grow from one reverse micelle, although not limited thereto. The resulting metal nanoparticles are generally not charged, i.e., neutral. However, some nanoparticles may be slightly positively charged on their surfaces. Thus far, no electricity is applied to form the metal nanoparticles.

Nanoparticle Colloid

The nanoparticles are dispersed in the liquid to provide a nanoparticle colloid. FIG. 8 conceptually illustrates the resulting nanoparticle colloid. In the course of the reduction of metal ions and growth of nanoparticles, some reverse micelles break or burst, and accordingly nanoparticles from those burst reverse micelles may be dispersed into the hydrophobic space. Some of those nanoparticles 151 may freely float in the resulting colloid composition outside hydrophilic cores of reverse micelles. Some other nanoparticles 153 may be surrounded or bound by hydrophilic heads of surfactant molecules outside hydrophilic cores of reverse micelles. Some nanoparticles 155 remain inside reverse micelles 141. Overall, in the resulting nanoparticle colloid, the solid nanoparticles 151, 153, 155 are dispersed in the liquid composition including reverse micelles 141, water and surfactant molecules. Because the nanoparticles 151, 153, 155 are significantly separated from each other in the nanoparticle colloid composition, it is unlikely that the nanoparticles congregate and grow to larger particles.

Reducing Agent

The reducing agent is a chemical entity that can donate one or more electrons to the metal ions contained in the nanoparticle colloid. The reducing agent is a hydrophilic compound for entering the hydrophilic core of the reverse micelle. Non-limiting examples of the hydrophilic reducing agent include ascorbic acid, acetic acid, form aldehyde, citric acid, hydroxylamine, hypophosphite, etc.

Amount of Reducing Agent

The hydrophilic reducing agent is added to the nanoparticle colloid in an amount sufficient to reduce the metal ions contained therein. In some embodiments, the reducing agent is added in an excessive amount that is substantially more than the stoichiometric amount for reducing the total metal ions contained in the nanoparticle colloid. Here "substantially more than" means more than by 20, 40, 60, 80, 100, 120, 140, 160, 180, 200, 250, 300 or 400%.

Stirring

While and/or after adding the reducing agent, the mixture may be stirred to facilitate distribution of the reducing agent. Stirring may facilitate the reducing agent to enter the hydrophilic spaces of the reverse micelles. Accordingly, the time for fully reducing the metal ions in the hydrophilic spaces can be reduced. Stirring may be performed continuously or intermittently. In embodiments, stirring is performed for a period between 1 hour and 10 hours.

Removing the Surfactant and Forming Clusters

At step 605, the surfactant is substantially removed from the nanoparticle colloid composition to form clusters of nanoparticles. In the nanoparticle colloid, the surfactant may stabilize individual nanoparticles, and accordingly nanoparticles may not cluster together when a significant amount the surfactant is present. To remove the surfactant from the nanoparticles, the nanoparticle colloid is subject to centrifugation. After the centrifugation, most nanoparticles settle in the bottom portion, and the surfactant molecules may be in the supernatant and in the bottom portion. The supernatant is separated from the bottom portion containing most of the nanoparticles. In embodiments, liquid may be added to the separated nanoparticles to dilute the surfactant in the collected bottom portion. The liquid added to the nanoparticles may be water or aqueous solution, which may be an acidic or basic solution although not limited thereto. The centrifugation, collecting the bottom portion, and adding liquid may be repeated multiple times to collect nanoparticles in which the surfactant is substantially removed.

Chemical Bond between Surfactant and Nanoparticle

Depending upon the surfactant, some nanoparticles have a strong chemical bond with hydrophilic heads of some surfactant molecules. Surfactant molecules having negatively charged hydrophilic heads may form a coordinate bond with nanoparticle surfaces. Also, if the surfactant molecules have electron-abundant hydrophilic heads (even if they are not charged), they may form a coordinate bonding with nanoparticle surfaces. When such surfactants are used, the chemical bond must be broken to remove the surfactant from the nanoparticle colloid.

Breaking Chemical Bond

In some embodiments, an acidic or basic solution is added to the nanoparticles-surfactant colloid after forming nanoparticles at step 603 and before centrifugation at step 604 of FIG. 6B. The acid or base of the added solution causes a chemical reaction to break the coordinate bond between the surfactant and nanoparticles to free nanoparticles. For example, protons from acid may bond with the negatively charged or electron-abundant surfactant heads to free the nanoparticles. The subsequent centrifugation and collection of bottom portion separate the nanoparticles freed from the surfactant molecules. In embodiments, adding acidic or basic solution may be performed at least once before centrifugation. In some embodiments, adding acidic or basic solution may be performed before each centrifugation. In embodiments, the acid and base may be washed with water or other solvent after centrifugation.

Acidic or Basic Solution

In embodiments, the acid or base is chosen in view of the surfactant such that the surfactant molecules are effectively detached from the nanoparticles. In embodiments, the acidic solution has a pH value lower than about 3, although not limited thereto. For example, non-limiting examples of acid for the acidic solution include HCl, $HNO_3$, $H_2SO_4$, $HClO_4$, etc. In embodiments, the basic solution has a pH value higher than about 10, although not limited thereto. For example, non-limiting examples of base for the basic solution include NaOH, KOH, $Ca(OH)_2$, etc.

Cluster Colloid

After or in the processes for removing the surfactant and collecting nanoparticles, nanoparticles tend to cluster together or agglomerate to form clusters of nanoparticles. In liquid, the clusters are dispersed to form a cluster colloid. Each cluster includes and is made of the metal nanoparticles interacting with each other to form a larger body. Individual nanoparticles in the clusters are most likely electrically neutral. Although the invention is not bound by any theory or belief, it is believed that protons, hydroxide and other charged electrolytes may be bound to nanoparticles surfaces and that ionic interactions of these electrolytes with adjacent nanoparticles may keep neighboring nanoparticles together to form the clusters. In fact, the liquid of the cluster colloid contains a good amount of electrolytes originated from the metal ion source and the acidic or basic solution used in the previous preparation steps although the surfactant molecules were substantially removed.

Clusters and Nanoparticles

Figure 9:
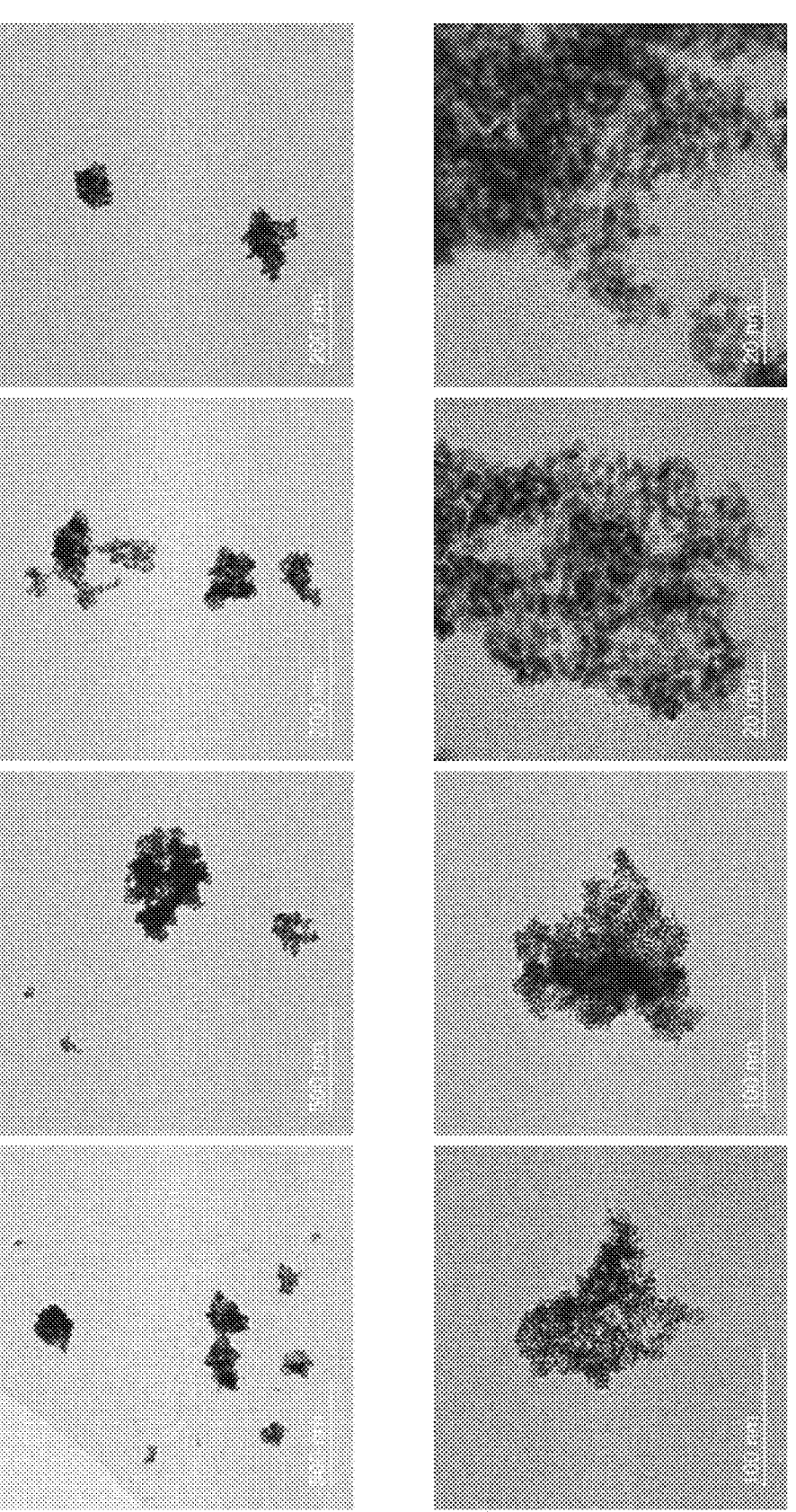
FIG. 9 includes TEM photographic images of nanoparticle clusters according to an embodiment.

FIG. 9 provides TEM photographic images of nanoparticle clusters from a diluted sample of cluster colloid. Two of the images of FIG. 9 are also found in FIGS. 5B and 5C. In these images, the clusters do not have a regular shape and are about 30 to about 500 nm long. The nanoparticles 121 in the clusters are discrete and generally spherical or oval, and have a diameter of about 2-3 nm. There are interparticular gaps 125 between neighboring or adjacent nanoparticles 121 with a gap distance of about 1-2 nm. These interparticular nanopores 125 are primarily responsible for glucose oxidation in a glucose-sensing electrode having a clustered nanoporous layer.

Centrifugation

The centrifugation may be performed at a rotational speed between 3000 and 5000 rpm. The centrifugation may continue for a period between 3 and 15 minutes. After centrifugation, the supernatant is removed, and the bottom portion containing the nanoparticles are collected. Liquid is added to the collected bottom portion to dilute surfactant contained therein. The centrifugation, collecting bottom portion and adding liquid may be repeated multiple times, e.g., three times or more.

Surfactant Substantially Removed

With the multiple processing of centrifugation, the surfactant is substantially removed. In the resulting cluster colloid, the concentration of surfactant becomes significantly low although it may not be completely removed. In the beginning, the reverse micelle phase contains the surfactant from about 10 to about 60 wt. The resulting cluster colloid may contain no surfactant at all. Practically, the resulting cluster colloid is substantially free of the surfactant. The remaining surfactant in the resulting cluster colloid or in the final collection of bottom portion may be greater than 0.0001 parts by weight with reference to 100 parts by weight for the nanoparticles and smaller than about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4 or 2.6 parts by weight with reference to 100 parts by weight for the nanoparticles. In embodiments, the remaining surfactant may be in an amount smaller than about 0.01, 0.02, 0.03, 0.04, 0.05, 0.06, 0.07, 0.08, 0.09, 0.1, 0.2, 0.3, 0.4 or 0.5 parts by weight with reference to 100 parts by weight for the nanoparticles.

Concentration of Nanoparticles in Cluster Colloid

After the multiple processing of centrifugation, the total amount of nanoparticles (as part of clusters and free nanoparticles) in the final collection of bottom portion may be about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 wt %. In embodiments, the concentration may be within a range formed by selecting any two numbers listed in the immediately previous sentence, e.g., between about 20 and about 30 wt %, between about 15 and 25%, etc.

Storing Cluster Colloid

The clusters are dispersed in the cluster colloid for an extended period, e.g., longer than a week or a month without any treatment. The cluster colloid may be stored in a container for a while after preparation and before subsequent processing. Once prepared, the cluster colloid may be subject to sales and transportation for processing by others or in other locations. To maintain the colloidal property for a longer period, the concentration of nanoparticles may be adjusted after the final collection of bottom portion. In embodiments, the cluster colloid of the final collection of bottom portion may be stored or transported in a container with or without adjusting the concentration.

Adjusting Concentration for Dispensing

At step 607, the collected cluster colloid may be stored for a while with or without dilution with a solvent. The dilution may be to adjust the concentration of clusters in the cluster colloid for the subsequent processing, e.g., dispensing. The solvent may be water or organic compound. One or more additive compounds may be added. By the dilution, the concentration of the nanoparticles or clusters is adjusted to about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.5, 5, 5.5, 6, 6.5, 7, 7.5, 8, 8.5, 9, 9.5, 10, 11, 12, 13, 14 or 15 wt %. In embodiments, the concentration of the nanoparticles or clusters may be within a range formed by selecting any two numbers listed in the immediately previous sentence, e.g., between about 0.5 and about 2 wt %, between about 1 and 3 wt %, etc. After the dilution, the remaining surfactant may be less than about 0.1, 0.2, 0.4, 0.6, 0.8 1, 1.2, 1.4, 1.6, 1.8 or 2 wt %.

Dispensing Cluster Colloid

At step 609, the cluster colloid is dispensed on a substrate 129 for producing the nanoporous layer, while it maintains its colloidal property. Various dispensing technologies may be utilized to dispense the cluster colloid. Dispensing may be controlled to form a certain thickness of the dispensed cluster colloid or to provide an appropriate thickness of the resulting nanoporous layer after subsequent drying. In the alternative, dispensing may be controlled to provide an appropriate roughness factor value of the resulting nanoporous layer.

Underlying Substrate

The cluster colloid may be applied onto a substrate made of any material. In embodiments for glucose-sensing electrodes, the cluster colloid may be applied onto a conductive or semiconductive surface for the conductive layer 110 as discussed above. In some embodiments, the substrate includes two or more conductive layers.

Drying Liquid to Form Clustered Nanoporous Layer

At step 611, the dispensed cluster colloid is subject to a condition for drying the liquid. Upon dispensing, the nanoparticle clusters are float in the liquid and freely travel horizontally and vertically. As the liquid dries off, the height of the cluster colloid decreases. As the liquid continues to dry off, clusters become contacting neighboring clusters vertically between the underlying substrate 129 and the top of the cluster colloid and horizontally. Mobility of the clusters becomes significantly limited. Sometime later, the liquid level becomes lower than clusters located at or near the top. Once the drying is complete, the nanoparticle clusters deposited on the substrate 129 forming a nanoporous layer having a clustered morphology 120 as illustrated in FIG. 5A.

Thickness of Nanoporous Layer

The resulting nanoporous layer has a thickness of about 0.4, 0.6, 0.8, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 µm. In embodiments, the thickness may be within a range formed by selecting any two numbers listed in the immediately previous sentence, e.g., between about 1 µm and about 10 nm.

No Washing Nanoporous Layer

The resulting nanoporous layer does not require washing with water or other liquid. In embodiments, the resulting nanoporous layer in a clustered morphology is not washed with water or other liquid at all subsequent to drying. In embodiments, the nanoporous layer is not subject to contacting liquid except in a subsequent processing for adding a layer over the nanoporous layer.

Yield—Recovery of Metal

If an excessive amount of reducing agent is added to the nanoparticle colloid, most metal ions therein are reduced to form metal atoms, which coagulate to form nanoparticles. The subsequent processing of removing the surfactant also collects most nanoparticles in clusters. Thus, most metal ions added to the foregoing processes are ultimately collected in the form of clusters of nanoparticles and deposited in the resulting nanoporous layer 117. In embodiments, over 89, 90, 91, 92, 93, 94, 95, 96, 97 or 98% of inputted metal ions are collected in the form of nanoparticle clusters before dispensing.

Mass Production

The nanoporous layer 117 can be mass-produced by printing the cluster colloid over the substrate 129. Printing the cluster colloid takes only one second or two. While drying the liquid may take longer time, it only takes a large space for drying. In embodiments, a number of separate substrates are provided, and printing may be performed on each of the separate substrates. Then, each printed substrate is dried to form a nanoporous layer. Alternatively, multiple areas are printed with the cluster colloid on a single substrate, and the single substrate may be subsequently cut into multiple pieces, each including a printed area. The single substrate may be dried before cutting.

No Electroplating or No Application of Electricity

Throughout the process, no electroplating is utilized to form the clustered morphology for the nanoporous layer. Further, no electricity is applied to the substrate 129 on which the nanoporous layer is formed.

Non-Clustered Nanoporous Layer

Non-Clustered Morphology

Figure 10A:
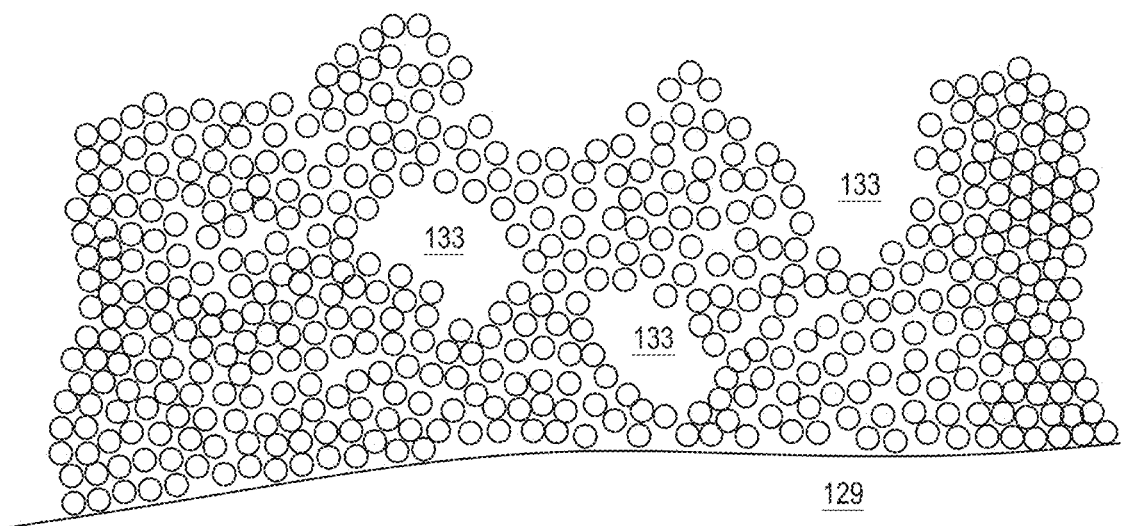
FIG. 10A illustrates a non-clustered morphology of a nanoporous layer according to an embodiment.
Figure 10B:
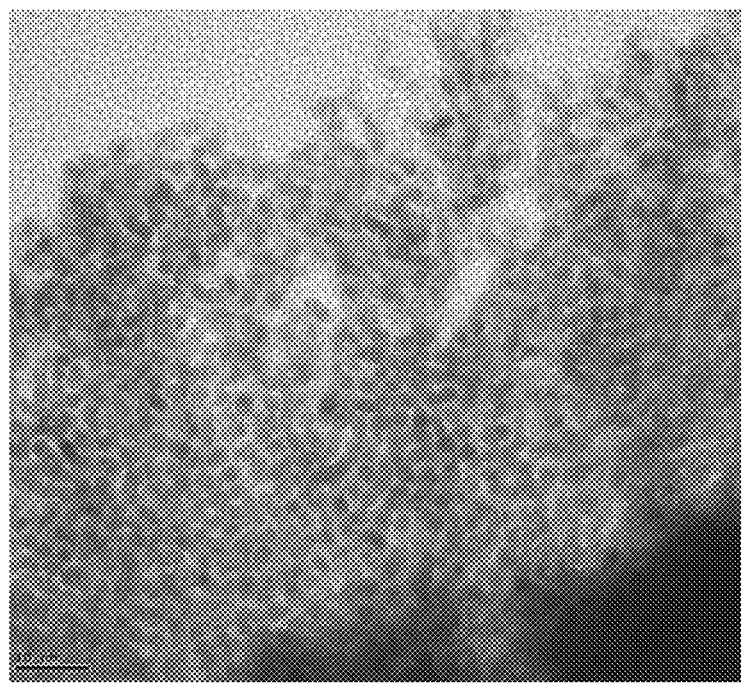
FIG. 10B is a TEM photographic image of a non-clustered morphology of a nanoporous layer formed on a metal surface according to an embodiment.

FIG. 10A illustrates a non-clustered morphology 161 for the nanoporous layer 117. As in the clustered morphology 120, the non-clustered morphology 161 includes both nanoparticles 121 and interparticular nanopores 123 formed between neighboring or adjacent nanoparticles 121. The discussions of the nanoparticles 121 and interparticular nanopores 123 generally apply to the non-clustered morphology 161. FIG. 10B is a TEM photographic image of a non-clustered morphology of a nanoporous layer formed on a metal surface, in which the dark portion is part of the metal surface. The nanoparticles of and interparticular pores in the TEM photographic image are similar to those in the illustration of FIG. 10A.

No Clusters and No Intercluster Gaps

Unlike the clustered morphology 120, the non-clustered morphology 161 does not include clusters 123 or intercluster gaps 127. To produce a non-clustered morphology, nanoparticles are deposited on the substrate 129 by electroplating without preparing clusters before electroplating. As a result, neither clusters nor intercluster gaps are formed in the resulting configuration, i.e., non-clustered morphology 161. Accordingly, the non-clustered morphology 161 does not have the characteristics of the clustered morphology coming from the clusters 123 or intercluster gaps 127.

Cavities of Non-Clustered Morphology

While no intercluster gaps exist, the non-clustered morphology 161 may include internal cavities 133 that are significantly larger than the interparticular nanopores 123. The internal cavities 133 may be formed during the course of electroplating because nanoparticles are not always sequentially stacked on the immediately underlying surface. The internal cavities 133 are in irregular shapes and in irregular sizes. The internal cavities 133 may be found throughout the nanoporous layer 117.

Cavities Distinguished from Intercluster Gaps or Spaces

The cavities 133 of the non-clustered morphology are distinguished from the intercluster gaps 127 of the clustered morphology 120. The cavities 133 are formed because electroplating and deposition of nanoparticles are not at the same rate over surfaces of the substrate 129. The cavities 133 do not surround or define a cluster or clusters 125 of nanoparticles 121. Rather, each cavity 133 is surrounded or defined by the agglomerated or conglomerated body of nanoparticles 121. While the cavities 133 may be interconnected via interparticular nanopores 123, the cavities 133 themselves are not interconnected throughout the nanoporous layer 117 or some substantial portion thereof. Further, the cavities 133 do not occupy as much volume of the nanoporous layer 117 (lower roughness factor in the non-clustered morphology) as the intercluster gaps 127 (higher roughness factor in the clustered morphology).

Substrate Substantially Covered with Nanoparticles

Referring to FIGS. 10A and 10B, the top surface of the substrate 129 is substantially covered with nanoparticles 121. In some embodiments, no substantial internal spaces are formed on or immediately above the substrate 129, although not limited thereto.

Clustered and Non-Clustered Morphologies Compared

Overall, the clustered morphology 120 is much less dense than the non-clustered morphology 161. For the same thickness, the clustered morphology 120 has a higher roughness factor than the non-clustered morphology 161, and accordingly, to produce the same roughness factor, the clustered morphology 120 may be thinner than the non-clustered morphology. Also, given that the cluster's irregular shapes, intercluster gaps 127 of the clustered morphology 120 are interconnected generally throughout the nanoporous layer 117, whereas the internal cavities 133 of the non-clustered morphology 161 are not as connected as the intercluster gaps 127. Accordingly, interparticular nanopores 125 within clusters 123 are connected to the network of intercluster gaps 127 in the clustered morphology 120, whereas in the absence of intercluster gaps in the non-clustered morphology 161, interparticular nanopores 125 may not be as connected as those in the clustered morphology 120.

Making Non-Clustered Nanoporous
Layer—Electroplating

Overall Process

Figure 11:
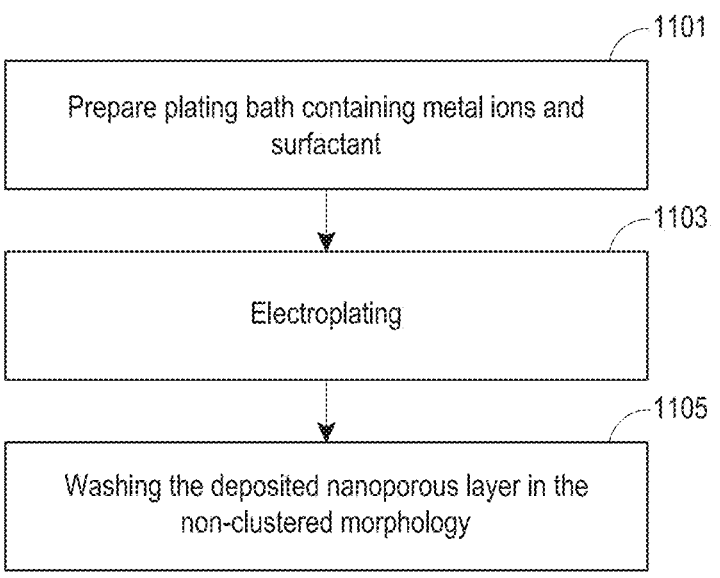
FIG. 11 is a flowchart for making a non-clustered nanoporous layer according to an embodiment.

A nanoporous layer having a non-clustered morphology may be prepared using an electroplating. Referring to FIG. 11, at step 1101, a plating bath is prepared to contain metal ions and a surfactant in a reverse micelle phase. Subsequently at step 1103, electroplating is performed in the plating bath for depositing a nanoporous layer in the non-clustered morphology. At step 1105, the resulting nanoporous layer is washed to remove surfactant therefrom.

Preparing Plating Bath

At step 1101, a plating bath is similar to the reverse micelle phase of step 601 of FIG. 6A for making a clustered nanoporous layer without electroplating. The plating bath includes a surfactant in reverse micelle phase and a metal ion source material as in making a clustered nanoporous layer. All discussions relating to the surfactant and metal ion source material of step 601 of FIG. 6A are applicable to the step 1101 of FIG. 11. However, the plating bath at step 1101 is not identical to the reverse micelle phase of step 601. One important difference may be that the plating bath may require some additional materials in view of the electroplating in the next step. For many metal source compounds that may spontaneously be reduced, the plating bath may require a chelating agent to keep the metal ions from being spontaneously reduced during and before electroplating. In contrast, no such chelating agent may be needed in the reverse micelle phase of step 601.

Electroplating

At step 1103, electroplating is performed in the aqueous liquid composition of reverse micelle phase containing metal ions. In a plating bath containing the liquid composition, cathode and anode electrodes are submerged and are connected to a power supply. When a DC voltage is applied between the cathode and anode electrodes, the cathode electrode supplies electrons to the aqueous liquid composition. Electrons may jump from the cathode electrode to nearby hydrophilic spaces of reverse micelles to reduce the positively charged metal ions to metal atoms inside the hydrophilic spaces. The metal atoms get together and form a metal particle, which may deposit onto the cathode electrode surface. In the course the reverse micelles may burst. Electrons supplied to the cathode electrode travel through the deposited nanoparticles and become available on outer surfaces of deposited nanoparticles. The electrons then are available for reducing nearby metal ions to form metal nanoparticles for depositing over the already deposited nanoparticles.

Time for Electroplating

The electroplating is performed for about 5, 10, 15, 20, 25, 30, 35, 40, 45, 50, 55 or 60 minutes to obtain a nanoporous layer having roughness factor of 100 to 800. In embodiments, the time for electroplating may be within a range formed by selecting any two numbers listed in the immediately previous sentence, e.g., between about 10 and about 30 minutes. In embodiments, time for electroplating is controlled for obtaining a nanoporous layer having roughness factor of 100 or above.

Forming Layer after Layer and Cavities

In the reduction by electroplating, nanoparticles adjacent to the cathode electrode are first deposited on the surface of the cathode. Then, additional nanoparticles deposit over the previously deposited nanoparticles 121. Accordingly, nanoparticles deposit generally layer after layer over the cathode electrode. However, because depositing nanoparticles may not occur at the same rate throughout the cathode surface and the previously deposited layer of nanoparticles, internal cavities 133 may be formed in the resulting nanoporous layer. The deposition of nanoparticles may grow horizontally or laterally over a space where nanoparticles are not deposited, some cavities 133 may be enclosed with nanoparticles formed thereover. Although cavities 133 may be ultimately interconnected via interparticular nanopores 125, micro-sized channels are not formed throughout the nanoporous layer 117 or in a substantial portion thereof to interconnect the cavities 133.

Surfactant Deposited Together

In the course of electroplating, reverse micelles enclosing these nanoparticles may burst, and the nanoparticles are deposited on the cathode electrode. A significant amount of surfactant molecules from the burst reverse micelles are deposited on the cathode electrode along with the nanoparticles. In the course of electroplating, surfactant molecules may bond to nanoparticle surfaces, and nanoparticle-surfactant molecule complexes may be deposited together. The surfactant molecules may be inserted or trapped between nanoparticles in the resulting nanostructure.

Remaining Surfactant and Effects

The surfactant molecules deposited together with nanoparticles may occupy gaps and spaces between nanoparticles, i.e., interparticular pores. These surfactant molecules may effectively block nanopores and nanoparticle surfaces that are responsible for glucose oxidation. Further, the surfactant molecules may be degraded on the metal surfaces, which may contaminate the nanoparticle surfaces. Overall, the sensitivity of glucose oxidation may be affected by the surfactant remaining in the nanoporous layer.

Washing

At step 1105, the resulting nanoporous layer is washed with water or other liquid to remove surfactant molecules therefrom. However, washing is not effective to substantially remove surfactant molecules as many surfactant molecules are trapped between neighboring nanoparticles and also washing liquid may reach only to a certain level.

No Nanoparticle Colloid

In the electroplating method, no reducing agent is added to reduce the metal ions to form nanoparticles. During the course of electroplating, nanoparticles may be formed in hydrophilic spaces of reverse micelles that are next to or near the cathode electrode surfaces. The nanoparticles are then likely deposited onto the cathode electrode. However, nanoparticles are not formed in hydrophilic spaces of reverse micelles throughout the liquid composition. Accordingly, no nanoparticle colloid is formed as illustrated in FIG. 8.

No Clusters and No Cluster Colloid

In the electroplating method, there is no step for removing the surfactant after forming nanoparticles. Rather, the surfactant and nanoparticles are deposited together during the process of electroplating. Accordingly, no clusters are formed in any stage of the process, and no cluster colloid is formed either.

Yield—Recovery of Metal

At the completion of electroplating, the plating bath contains a significant amount of metal ions. Thus, the recovery of metal in the electroplating method may not be as high as in the reduction by adding an excessive amount of reducing agent as in the process for clustered nanoporous layer.

Making Nanoporous Layer Using Liquid Crystalline Phase

Figure 12:
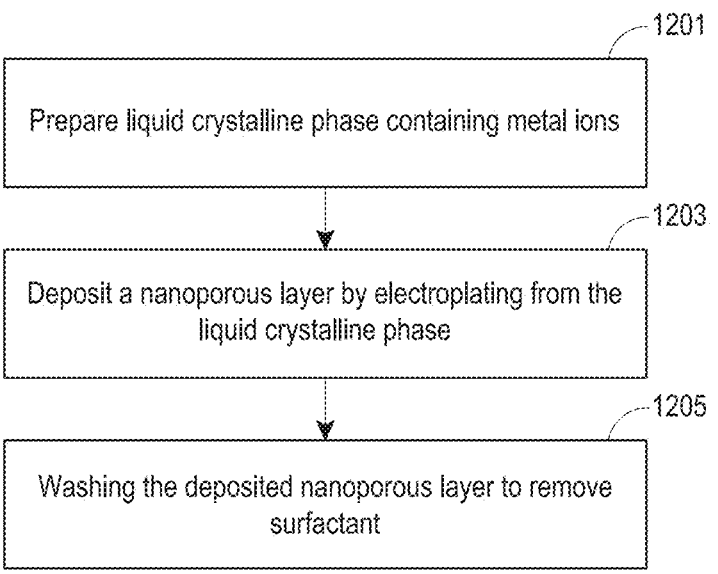
FIG. 12 is a flowchart for making a hexagonal nanostructure according to an embodiment.
Figures 13A, 13B:
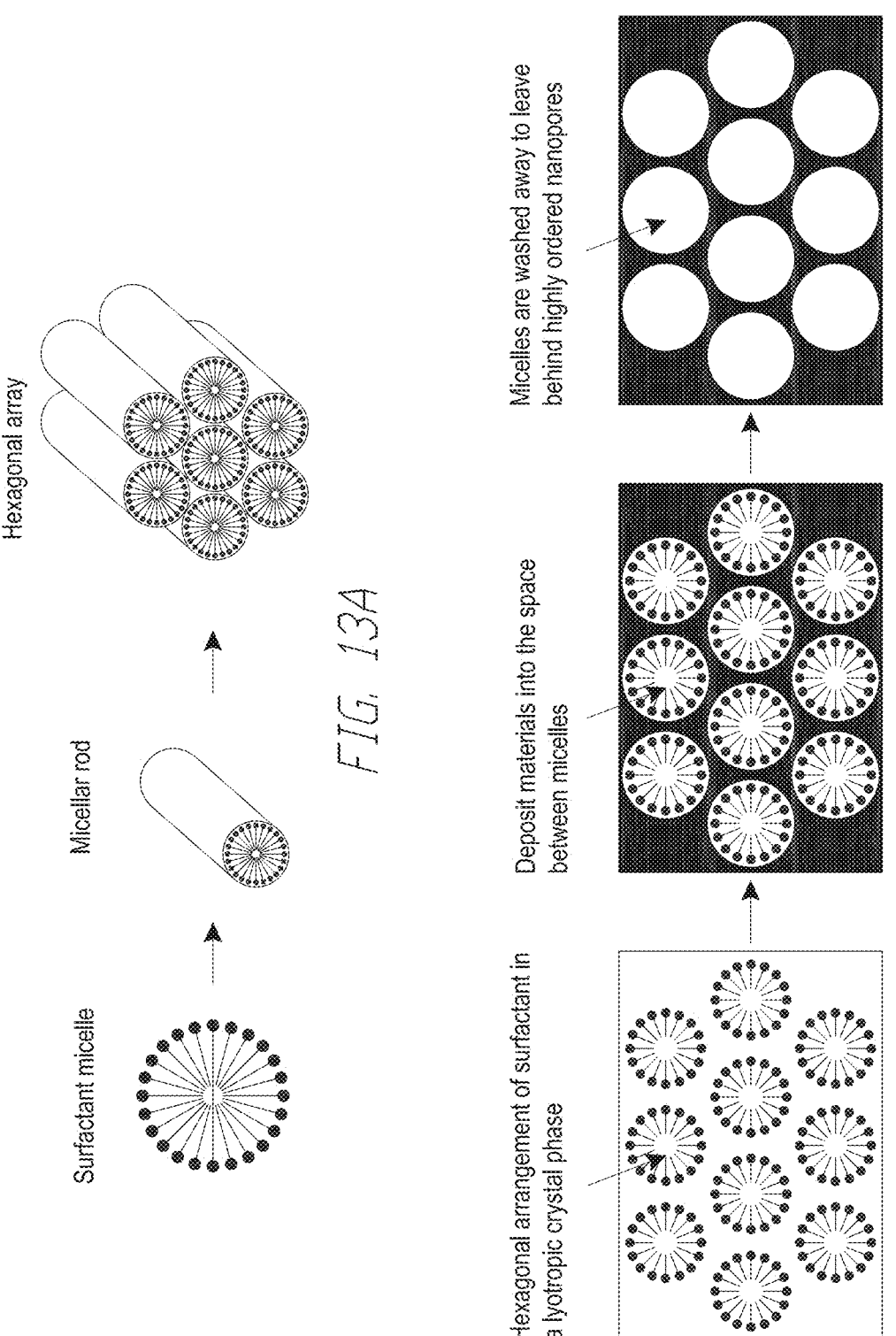
FIG. 13A illustrates formation of a hexagonal arrangement according to an embodiment.
FIG. 13B illustrates deposition of metal using a hexagonal arrangement of liquid crystalline phase.

The nanoporous metal layer may be fabricated from a liquid crystalline phase of a surfactant. Referring to FIG. 12, at step 1201, an aqueous liquid composition is prepared to contain metal ions and a surfactant in a liquid crystalline phase, for example, in a hexagonal arrangement. Subsequently at step 1203, the aqueous liquid composition is subject to electroplating for depositing nanoporous layer in which metal atoms are deposited using the liquid crystalline phase as a template. At step 1205, the surfactant is removed from the deposited hexagonal nanostructure. FIG. 13A illustrates formation of a hexagonal arrangement. FIG. 13B illustrates deposition of metal using a hexagonal arrangement of liquid crystalline phase.

Maltose-Blocking Layer

Maltose

Figure 20:
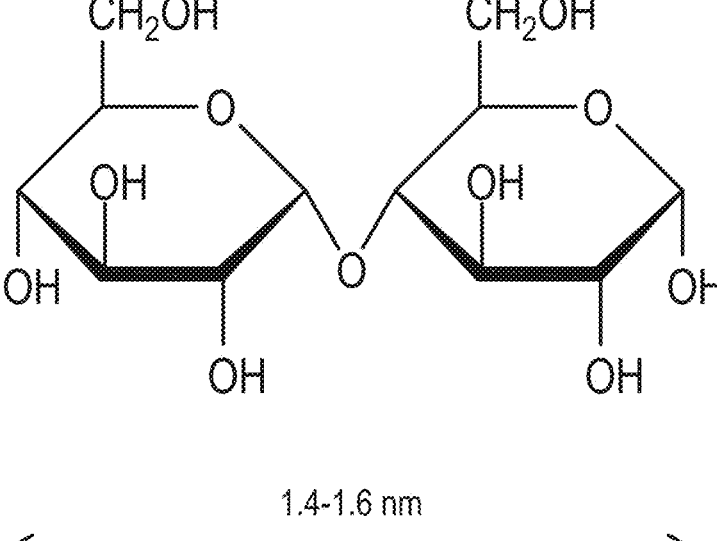
FIG. 20 is a structural formula of a maltose molecule.

Maltose is a disaccharide composed of two units of glucose as illustrated in FIG. 20. Maltose may be present in blood or other bodily fluid of human or animal. The presence of maltose in a test fluid may interfere with the accurate sensing of a glucose level in both enzymatic and non-enzymatic glucose-sensing systems.

Interference of Maltose in Enzymatic Glucose Sensing

Some enzymes used in enzymatic glucose-sensing system oxidize maltose as well as glucose. Accordingly, when maltose exists in the test fluid, the enzymatic glucose-sensing system may have an inaccurate reading of glucose level due to maltose. If an inaccurate reading is used to control or adjust insulin infusion, the consequence may be serious.

Interference of Maltose in Non-enzymatic Glucose Sensing

The nanoporous layer 117 of the working electrode 103NE can oxidize maltose at the same bias voltage for sensing glucose. With the length of about 1.4-1.6 nm as illustrated in FIG. 20, maltose molecules may enter inter-particular nanopores 123 of the nanoporous layer 117 and be oxidized there along with glucose. Example 9.11 and FIG. 18 confirm that maltose can be detected along with glucose and other interfering chemical entities in PBS. Also, Example 10.9 and FIG. 19 confirm that maltose can be detected along with glucose and other interfering chemical entities in serum.

Non-enzymatic Working Electrode with Maltose-Blocking Layer

Figure 21:
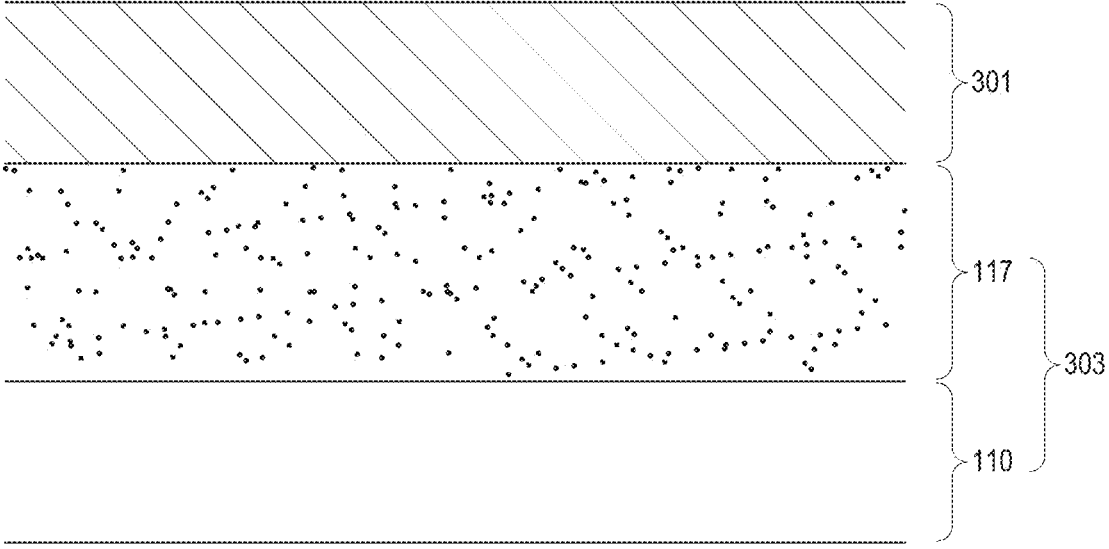
FIG. 21 illustrates a non-enzymatic working electrode including a maltose-blocking layer according to an embodiment.

Referring to FIG. 21, the working electrode 103NE includes a nanoporous layer 117 and a maltose-blocking or maltose-screening layer 301 over the nanoporous layer 117. In embodiments, the nanoporous layer 117 is capable of oxidizing both maltose and glucose whether it includes clustered or non-clustered morphology. The maltose-blocking layer 301 may contact the underlying nanoporous layer 117 or may be separated by an intervening layer. The working electrode 103NE may also include an additional functional layer 112 over the maltose-blocking layer 301. In the alternative, the additional functional layer 112 may be interposed between the maltose-blocking layer 301 and the nanoporous layer 117.

Selective Blocking of Maltose

The maltose-blocking layer 301 effectively or substantially blocks or inhibits maltose molecules from passing or penetrating therethrough while allowing glucose molecules to pass therethrough. With the maltose-blocking layer 301, maltose molecules contained in the test fluid may not reach its underlying nanoporous layer 117 at all or at a significant concentration to interfere glucose sensing. Given the selective maltose blocking effect of the maltose-blocking layer 301, it is unlikely that the existence of maltose in the test fluid affects the glucose sensing even if the nanoporous layer 117 is capable of oxidizing maltose at the same bias voltage for glucose oxidation. In addition, the maltose-blocking layer 301 effectively block or inhibit other molecules and components of the test fluid that are larger than maltose.

Bias Voltage

In the non-enzymatic glucose-sensing system, the addition of maltose-blocking layer 301 does not require an increase or decrease of the bias voltage for glucose sensing.

Porous Polymeric Layer

In embodiments, the maltose-blocking layer 301 is made of or includes a porous polymeric material through which glucose may pass but maltose may not pass. The porous polymeric material contains at least one poly-phenylenedi-amine (poly-PD) which include poly(m-phenylenediamine) (poly-mPD), poly(o-phenylenediamine) (poly-oPD), and poly(p-phenylenediamine) (poly-pPD).

Nano-Sized Thickness

The maltose-blocking layer 301 has a thickness at or about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nm. Throughout the discussions, the thickness of maltose-blocking layer refers to an average thickness of the polymer layer excluding the top 10% and bottom 10% of thickness variations. In embodiments, the thickness may be within a range formed by selecting any two numbers (two thickness values) listed in the immediately previous sentence, e.g., between about 15 nm and about 35 nm, between about 17 nm and about 33 nm, between about 18 nm and about 32 nm, between about 20 nm and about 30 nm, between about 21 nm and about 29 nm, between about 22 nm and about 28 nm, etc.

Level of Porosity

In embodiments, the maltose-blocking layer 301 has porosity that allows glucose molecules to pass through its thickness while effectively blocking maltose molecules from passing therethrough. To accomplish the goal of allowing glucose to pass and blocking maltose from passing, the overall porosity of the maltose-blocking layer needs to be adjusted to a desirable level. The overall porosity of the maltose-blocking layer 301 relate to the density (or internal morphology including pores and channels) and the thickness of the layer. The concentration of a material for the maltose-blocking layer and method of forming the maltose-blocking layer may be relevant to the density. While there has been some successes of adjusting the overall porosity using these parameters, it has been found that the level of porosity may not be generally defined or described using the concentration of the material and method of forming the layer. While thickness of the maltose-blocking layer also relates to the overall porosity, it is dependent upon the specific porosity or porosity per volume. Thus, the level of porosity needs to be defined in a different manner.

Sensitivity (Current Density) for Glucose and Maltose without Maltose-Blocking Layer For glucose monitoring, at steady state with the application of a bias voltage of 0.2-0.45 V in a test fluid with the glucose concentration of 4-20 mM (typical glucose level in human bodily fluid), the nanoporous layer 117 contacting the test fluid (i.e., no maltose-blocking layer) needs to generate glucose-oxidation current (electric current caused by oxidation of glucose alone) at a level higher than 10 $nA/mMcm^2$, the minimum current density (sensitivity) for glucose. According to embodiments, without the maltose-blocking layer the same nanoporous layer 117 would generate a similar level of electric current (i.e., higher than 10 $nA/mMcm^2$) at steady state with the application of a bias voltage of 0.2-0.45 V in a test fluid containing maltose at a concentration of 4-20 mM (the same as glucose concentration as above).

Porosity of Maltose-Blocking Layer by Current Density of Glucose and Maltose

According to embodiments, the maltose blocking layer 301 has porosity for allowing glucose to travel therethrough such that the glucose oxidation current is still higher than the minimum current density for glucose. Accordingly, when applying a bias voltage of 0.2-0.45 V in a test fluid with the glucose concentration of 4-20 mM, at steady state the working electrode 103NE with the maltose blocking layer 301 generates glucose-oxidation current at a level higher than 10 $nA/mMcm^2$, the minimum current density (sensitivity) for glucose. On the other hand, the maltose blocking layer 301 has porosity that effectively block maltose from passing therethrough such that, when applying a bias voltage of 0.2-0.45 V in a test fluid with the maltose concentration of 4-20 mM, at steady state electric current caused by maltose alone (maltose-oxidation current) is at a level lower than 5 $nA/mMcm^2$, the maximum current density for maltose with the maltose-blocking layer.

Electrochemical Polymerization

The porous polymer material for the maltose-blocking layer 301 may be formed on the nanoporous layer 117 by electrochemical polymerization (electropolymerization) using a cyclic voltammetric technique. In embodiments, a working electrode including the nanoporous layer is submerged in a reaction mixture solution containing monomer for the cyclic voltammetric electrochemical polymerization. By applying a bias voltage between the working and reference electrodes within the range of the monomer's oxidation voltage, polymerization occurs and a polymer layer is formed on the nanoporous layer. More details for the polymerization of phenylenediamine are disclosed in "Electropolymerization of 0-Phenylenediamine on Pt-Electrode from Aqueous Acidic Solution: Kinetic, Mechanism, Electrochemical Studies and Characterization of the Polymer Obtained", Sayyah et al, Journal of Applied Polymer Science, Vol. 112, Issue 6, 3695-3706 (2009), and "Electropolymerization of P-Phenylenediamine on Pt-Electrode from Aqueous Acidic Solution: Kinetics, Mechanism, Electrochemical Studies, and Characterization of the Polymer Obtained", Sayyah et al, Journal of Applied Polymer Science, Vol. 117, Issue 2, 943-952 (2010), each of which is hereby incorporated herein by reference.

Application of Oxidation Voltage

Figure 22:
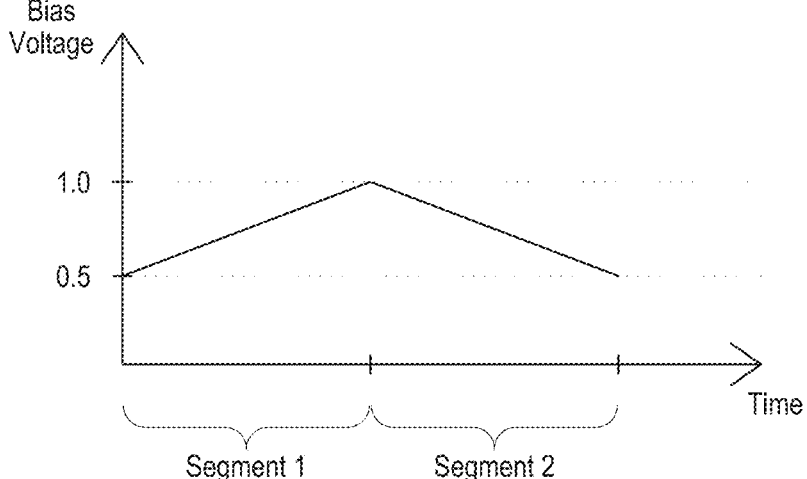
FIG. 22 illustrates scanning of oxidation voltage during cyclic voltammetric electrochemical polymerization of phenylenediamine according to embodiment.

The bias voltage may be varied during the cyclic voltammetry. For example, the bias voltage may be gradually increased within the oxidation voltage range for the initial time segment and then gradually decreased within the oxidation voltage range for the following time segment, although not limited thereto. For phenylenediamine, the bias voltage is applied between 0.5 V and 1.0 V. FIG. 22 illustrates an example of scanning the bias voltage during the cyclic voltammetric electrochemical polymerization of phenylenediamine.

Bias Voltage Scanning Speed

Together with the concentration of monomer discussed below, the scanning speed of the bias voltage between the lower end and the upper end of the oxidation voltage range may be relevant to the porosity and thickness of the resulting polymer layer. In embodiments, the scanning speed is at about 0.5, 1, 2, 4, 6, 8, 10, 15, 20, 25, 30, 40, 50, 60, 70, 80, 90, 100, 120, 140, 160, 180, 200, 220, 240, 260, 280, 300, 350 or 400 mV/sec. In embodiments, the scanning speed may be within a range formed by selecting any two numbers listed in the immediately previous sentence, e.g., between about 5 mV/sec and about 200 mV/sec.

Concentration of Monomer

The concentration of the monomer is at about 0.01, 0.05, 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 9.0, 9.2, 9.4, 9.6, 9.8 or 10 mM. In embodiments, the concentration of the monomer may be within a range formed by selecting any two numbers listed in the immediately previous sentence, e.g., between about 0.05 mM and about 0.8 mM, between about 1.0 mM and about 5.0 mM, etc. The foregoing concentrations are applicable to the three species of phenylenediamine.

Porosity in View of Monomer Concentration

Figure 24:
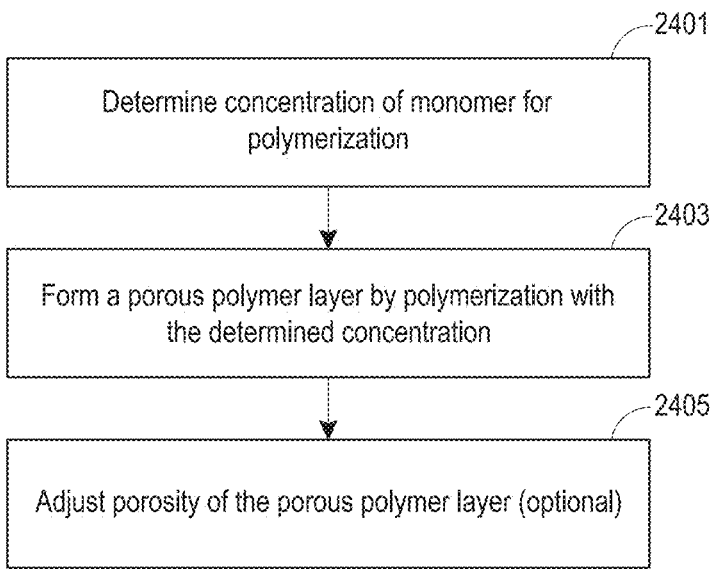
FIG. 24 is a flowchart for making a maltose-blocking layer according to an embodiment.

The concentration of monomer in the reaction mixture solution is relevant to the porosity of the resulting maltose-blocking layer. In the flowchart for making the maltose-blocking layer of FIG. 24, the monomer concentration is determined first at step 2401 and polymerization is carried out at step 2403. In embodiments, the monomer concentration under about 0.7 mM, about 0.6 mM, or about 0.5 mM may provide a desirable level of overall porosity for the maltose-blocking layer. In embodiments, when the monomer concentration is over about 0.7 mM, about 0.8 mM, about 0.9 mM, about 1.0 mM, about 1.1 mM, or about 1.2 mM, the resulting polymer layer does not have enough porosity to allow glucose to pass therethrough, i.e., generating glucose-oxidation current at a level lower than 10 $nA/mMcm^2$, the minimum current density (sensitivity) for glucose. At step 2405, the resulting polymer layer is subject to treatment for adjusting its porosity at step 2405.

Electric Shock for Adjusting Porosity

When the overall porosity of the polymer layer 302 is not at a desirable level, the polymer layer may be further treated for adjusting the porosity. For example, the polymer layer may be subject to an electric shock. In embodiments, the electric shock may be applied to the polymer layer 302 using the chronoamperometry setting illustrated in FIG. 23, in which an electric shock electrode 309 and polymer layer 302 formed on the nanoporous layer 117 are submerged in an electrolyte solution 311. A voltage supply 305 and a switch

307 are connected between the substrate 303 and the electric shock electrode 309. With the operation of the switch 307, electric current flows through the porous polymer layer 302 and causes morphology changes, which increases porosity of the polymer layer 302. As a result, the polymer layer 302 turns to the maltose-blocking layer 301 having a desirable level of porosity that allows glucose to pass through its thickness and effectively block maltose from passing therethrough.

Acidic Solution

The electrolyte solution for the electric shock may be an acidic solution having pH under about 2, 3 or 4 although not limited thereto. In some embodiments, the acidic solution may contain at least one acid. Non-limiting examples of acid for the acidic solution include phosphoric acid ($H_3PO_4$), nitric acid ($HNO_3$), chloric acid (HCl), formic acid, lactic acid, malic acid, citric acid, carbonic acid, sulfonic acid, etc.

Waveform for Electric Shock

The electric potential may be applied in various waveforms. In embodiments, the electric potential is applied in AC or DC. In embodiments, the electric potential is applied in multiple pulses or in a single pulse. In embodiments, the electric potential may be applied in other shapes of voltage signals.

Electric Potential for Electric Shock

The electric potential applied to the polymer layer 302 is about at or about 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 V. In embodiments, the maximum voltage may be within a range formed by selecting any two numbers listed in the immediately previous sentence, e.g., between about 0.5 and about 2.5 V, between about 1.0 and about 2.0 V, etc.

Period for Electric Shock

The period of applying electric potential is for or about 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4 or 4.5 seconds. In embodiments, the period may be within a range formed by selecting any two numbers listed in the immediately previous sentence, e.g., between about 0.5 and about 2.5 sec., between about 1.0 and about 2.0 sec., etc.

Maltose-Blocking Layer Also Applicable to Enzymatic Sensing

In embodiments, the maltose-blocking layer 301 may be applied to enzymatic glucose-sensing systems. Referring back to FIG. 2, the maltose-blocking layer 301 may be added as an additional functional layer 112 over the enzyme layer 111 to block maltose while letting glucose pass therethrough.

CGM Working Electrode

CGM System

A continuous glucose monitoring (CGM) system includes a glucose-sensing electrode that contacts biological fluid of a subject in vivo for measurement of glucose level contained in the biological fluid. In practice, a CGM electrode is inserted or implanted in the subject's body for measurement over an extended period, such as a few days, a week, weeks or months.

Non-Enzymatic CGM Working Electrode

Figure 31:
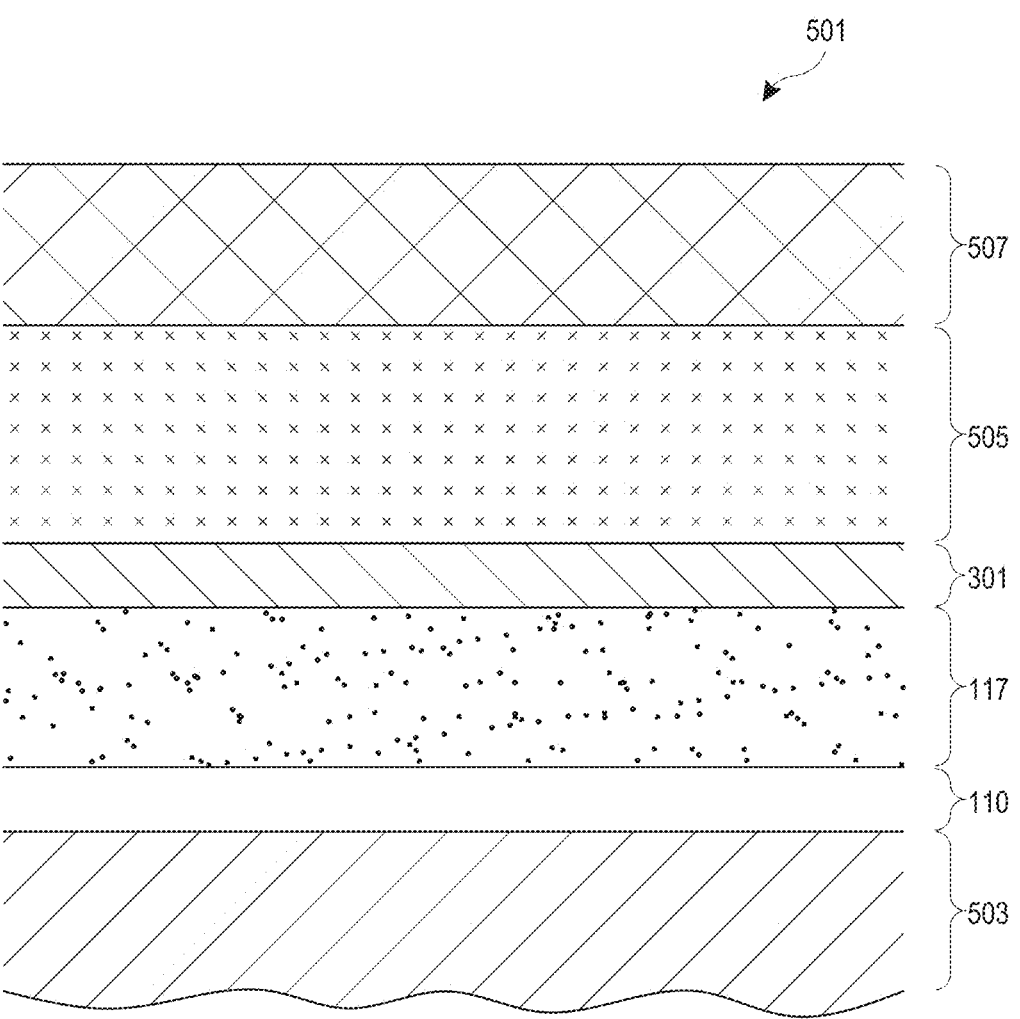
FIG. 31 illustrates a CGM working electrode according to an embodiment.

FIG. 31 illustrates a cross-section of a non-enzymatic CGM working electrode 501 according to an embodiment. The illustrated CGM working electrode 501 has a laminated structure that includes a base 503, a conductive layer 110, a nanoporous layer 117, a maltose-blocking layer 301, an electrolyte ion-blocking layer 505, and a biocompatibility layer 507.

Electrode Base

The base, base substrate or electrode base 503 provides a support for the laminated structure of the CGM working electrode 501. In embodiments, the base 503 is an electrically insulative layer and may be made of or contain a material such as, but not limited to, polyimide, polypropylene, polyethylene glycol, polyhydroxyethyl methacrylate (pHEMA) and other biocompatible polymers. In embodiments, the base 503 may be in the form of a flexible film of an electrically insulating and biocompatible material. The base 503 has a thickness ranging between about 30 μm and about 200 μm, although not limited thereto. The base 503 is an optional layer for the CMG sensing electrode 501 and may be omitted in some embodiments.

Conductive Layer

The conductive layer 110 may be placed over the base 503 with or without an intervening layer therebetween. In embodiments, the conductive layer 110 is formed by printing or dispensing a conductive or semiconductive material on the base 503, although not limited thereto. In the CGM working electrode 501, the conductive layer 110 may have a thickness ranging between about 100 nm and 100 μm, although not limited thereto. In some embodiments, the conductive layer 119 may include two or more sublayers of conductive or semiconductive materials. In embodiments where the base 503 is omitted, the conductive layer 119 may function as a support for the laminated structure over it.

Nanoporous Layer

The nanoporous layer 117 may be formed on the conductive layer 110. In the CGM working electrode 501, the nanoporous layer 117 has a thickness ranging between about 500 nm and about 10 μm, although not limited thereto. The nanoporous layer 117 may have at least one of clustered morphology, non-clustered morphology, hexagonal nanostructure or other nanoporous morphology.

Maltose-Blocking Layer

The maltose-blocking layer 301 may be formed on the nanoporous layer 117 to block maltose molecules from reaching the underlying nanoporous layer 117 while allowing glucose molecules to pass therethrough. In embodiments, the maltose-blocking layer 301 includes a polymeric material such as poly-PD having nano-sized pores for passing glucose molecules and not passing maltose molecules. The maltose-blocking layer may have a thickness ranging between about 5 nm and about 40 nm, although not limited thereto. The maltose-blocking layer 301 is an optional layer for the CMG sensing electrode 501 and may be omitted in some embodiments.

Electrolyte Ion-Blocking Layer (Electrode Conditioning Enhancement/Facilitation Layer)

The electrolyte ion-blocking layer 505 effectively limits or inhibits small electrolyte ions such as $Na^+$, $K^+$, $Ca^{2\pm}$, $Cl^-$, $PO_4^{3-}$ and $CO_3^{2-}$ from passing therethrough or diffusing toward the underlying nanoporous layer 117. As will be discussed later, the electrolyte ion-blocking layer 505 enhances conditioning of the CGM working electrode and also referred to as a working electrode conditioning enhancement or facilitation layer. The electrolyte ion-blocking layer 505 is porous so that glucose molecules can freely pass therethrough. When implemented, the electrolyte ion-blocking layer 505 is hydrophobic such that it would not quickly swell by absorbing water contained in the test fluid.

The electrolyte ion-blocking layer 505 may have a thickness ranging between about 0.1 μm and about 10 μm, although not limited thereto.

Materials for Electrolyte Ion-Blocking Layer

The electrolyte ion-blocking layer 505 may include or be made of at least one of, for example, poly(methyl methacrylate) (PMMA), poly(hydroxyethyl methacrylate) (PHEMA), and poly(methyl methacrylate-co-ethylene glycol dimethacrylate) (PMMA-EG-PMMA). Also, the electrolyte ion-blocking layer 505 may be formed of or additionally include a copolymer of methylmethacrylate and butylmethacrylate, and polymers obtained from polymerization of one or more monomers including methylmethacrylate, ethylmethacrylate, propylmethacrylate, butylmethacrylate, pentylmethacrylate, hexylmethacrylate, cyclohexylmethacrylate, 2-ethylhexylmethacrylate, methylacrylate, ethylacrylate, propylacrylate, butylacrylate, pentylacrylate, hexylacrylate, cyclohexylacrylate, 2-ethylhexylacrylate.

Biocompatibility Layer

The biocompatibility or bioprotection layer 507 interfaces with tissues and bodily fluid of the subject when the CGM sensor is implanted or inserted in the subject's body. The biocompatibility layer 507 contains at least one biocompatible material that is not toxic to the tissues of the subject and does not cause immunological rejection by the subject's body. Also, the at least one material of the biocompatibility layer 507 should allow bodily fluid to pass therethrough to reach the underlying nanoporous layer 117 such that sensing of glucose concentration is not significantly compromised by its own existence. The biocompatibility layer 507 may have a thickness ranging between about 5 μM and about 30 μM, although not limited thereto.

Materials for Biocompatibility Layer

The biocompatibility layer 507 may include or be made of at least one of, for example, poly(vinylalcohol), poly(ethyleneoxide-copropyleneoxide) (PEO-PPO), poly(ethyleneoxide) (PEO), poly(sulphone) (PS), poly(ethylene terephthalate) (PET), poly(ether-urethanes) (PU), poly(dimethylsiloxane) (PDMS), ethylene-co-vinylacetate (EVA), poly(methylmethacrylate), poly(tetrafluoroethylene) (PTFE), poly(propylene) (PP), poly(ethylene) (PE), polyethylene glycol, and polyhydroxyethyl methacrylate (pHEMA).

Modifications

The CGM working electrode 501 may include one or more additional functional layers although not shown in FIG. 31. In some embodiments, one or more of the maltose-blocking layer 301, electrolyte ion-blocking layer 505 and biocompatibility layer 507 may be omitted. In other embodiments, two or more of the maltose-blocking layer 301, electrolyte ion blocking layer 505 and biocompatibility layer 507 may be combined in one layer or change their locations.

No Enzyme Layer

The CGM working electrode 501 does not include an enzyme layer containing a glucose-specific enzyme. Nor does the CGM working electrode 501 contain any such enzyme in any of the layers.

No Oxygen Take-Up Layer

The CGM working electrode 501 does not include an oxygen take-up material or layer that would be needed for collecting and supplying molecular oxygen in case glucose oxidase is used for oxidation of glucose.

No Electron Mediator

The CGM working electrode 501 does not include an electron mediation material that would be needed for transferring electrons in case glucose dehydrogenase is used for oxidation of glucose.

Conditioning CGM Working Electrode or System

Transient Signals of Electric Current

Upon creating an electrochemical cell using a CGM working electrode with the application of a bias voltage, the CGM working electrode generates electric current. The electric current from the CGM working electrode represents the sum of background noises and electric current from glucose oxidation in the CGM working electrode. Initially, the electric current shows a transient behavior. As shown in FIGS. 25-30, in the beginning the electric current is very high compared to that caused by glucose oxidation alone and rapidly decreases. Subsequently, the rate of decrease slows down. Ultimately, the electric current settles at a level, i.e., steady state, although in vivo the current may fluctuate a bit within a tolerable range.

Electric Current for Glucose Sensing

For accurate glucose sensing, the electric current should be measured when the electrochemical cell and/or CGM working electrode are in a steady state. In other words, the electric current from a CGM working electrode should not change too much over time (i.e., settling at a level after the initial decrease) when the glucose concentration does not change. Further, for accurate glucose sensing, the background current (noises) should not be too high relative to the electric current caused by glucose oxidation alone. In other words, the total electric current should not be too high relative to the electric current from glucose oxidation alone. Conditioning CGM Working Electrode or Electrochemical Cell CGM working electrodes need conditioning before glucose sensing. Here, conditioning refers to the process of stabilizing CGM working electrodes for accurate glucose sensing. Upon completion of conditioning of a CGM working electrode, the electric current therefrom should settle at a level and should not be too high relative to the electric current from glucose. To provide accurate glucose level, a CGM system should use electric current measured after conditioning is finished. Conditioning of a CGM working electrode may take a long time. Commercially available enzymatic CGM working electrodes requires several hours to days for conditioning.

Desirable Rate of Electric Current Change

Given that the electric current from glucose oxidation in vivo is about tens of nano Ampere, for accurate glucose sensing, the decrease rate of the electric current from a CGM working electrode should be smaller than, for example, 20 nA (nano Ampere) per minute. For the sake of providing a reference point, the desirable rate of the electric current change should be a point at or below 20, 19, 18, 17, 16, 15, 14, 13, 12, 11, 10, 9, 8, 7, 6, 5, 4, 3 or 2 nA per minute. In embodiments, the rate of electric current change may be determined in a shorter or longer time period.

Desirable Level of Electric Current

Electric current from glucose oxidation in vivo is typically tens of nano Ampere. The desirable level of total electric current may change depending upon various factors including measurement accuracy, signal processing capability, data processing capability, etc. As these factors are further developed, the desirable level could increase. Nonetheless, given that the electric current from glucose oxidation in vivo is about tens of nano Ampere, for accurate glucose sensing, the electric current from a CGM working electrode should be smaller than, for example, 500 nA. For the sake of providing a reference point, the desirable electric current should be a point at or below 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110 or 100 nA.

Completion of Conditioning

A CGM system determines that conditioning of its CGM working electrode or its electrochemical cell is complete. The CGM system may determine completion of conditioning when the rate of electric current change is or stays at or below a predetermined value, e.g., a desirable rate of electric current change or decrease as set forth above. The CGM system determines completion of conditioning when the total electric current change stays for a predetermined time at or below a predetermined value, e.g., a desirable level of electric current as set forth above. The CGM system may determine completion of conditioning when the rate of electric current change is or stays at or below its predetermined value and further when the total electric current change stays for a predetermined time at or below its predetermined value, e.g., the rate of electric current change being less than 5 nA/min and the total electric current staying less than 400 nA for 1 minute.

Notifying Completion of Conditioning

A CGM system may notify its user of completion of conditioning. Upon or sometime after forming the electrochemical cell for glucose oxidation, the CGM system may begin monitoring the electric current from its CGM working electrode. When the electric current meets one or more requirements for the completion of conditioning, the CGM system may provide a notification to its user for notifying the completion of conditioning. The notification may be in any form including sound, vibration, light or information display. In addition or in the alternative, the CGM system may not provide any information indicating a glucose level prior to completion of conditioning.

Reducing Time for Conditioning CGM Working Electrode

Concentration Discontinuity of Small Electrolyte Ions

Figure 32:
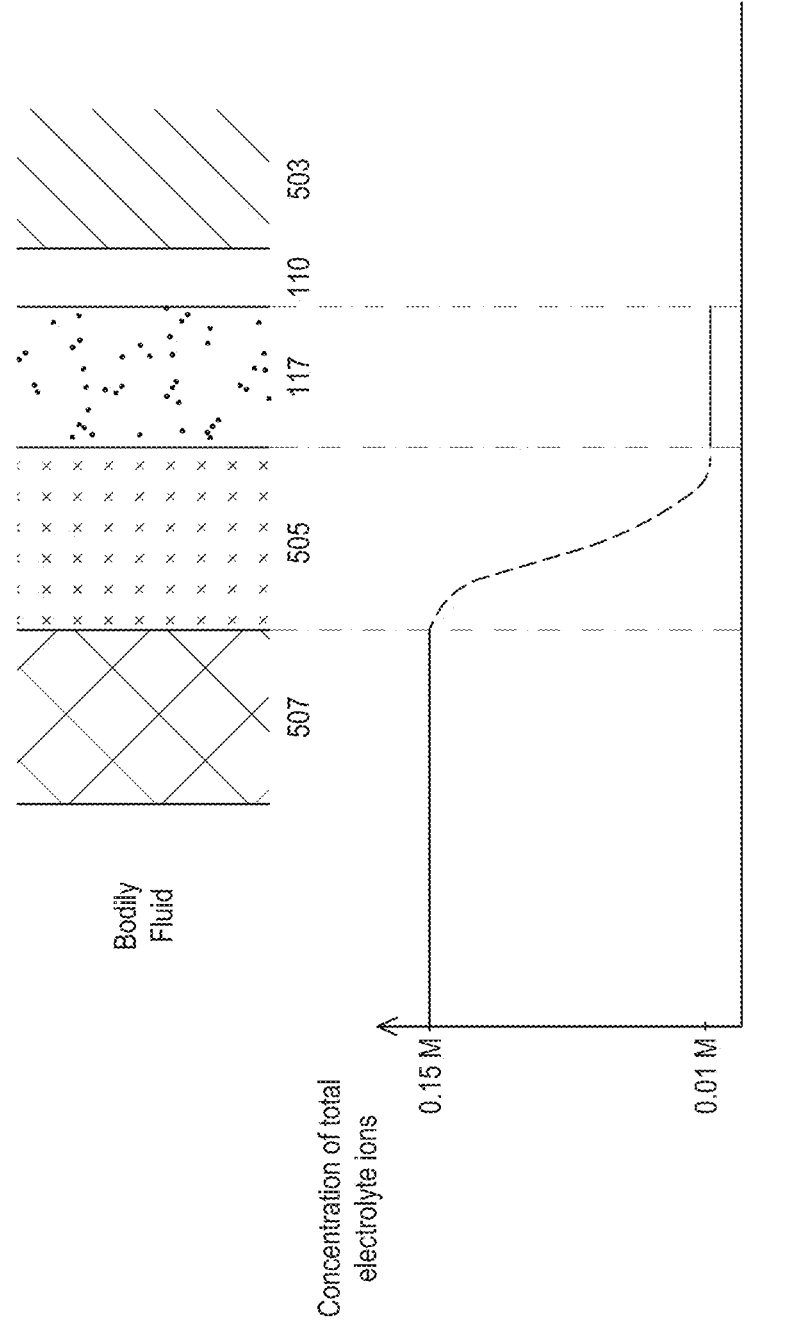
FIG. 32 illustrates electrolyte concentration drop across the thickness of an electrolyte ion-blocking layer according to an embodiment.

Human bodily fluid contains a significant amount of electrolyte ions of $Na^+$, $K^+$, $Ca^{2+}$, $Cl^-$, $PO_4^{3-}$ and $CO_3^{2-}$. In embodiments, the electrolyte ion-blocking layer 505 limits or inhibits the electrolyte ions of $Na^+$, $K^+$, $Ca^{2+}$, $Cl^-$, $PO_4^{3-}$ and $CO_3^{2-}$ from passing therethrough. As a result, between above the electrolyte ion-blocking layer 505 and below the same layer, the concentration of these electrolyte ions are significantly different. FIG. 32 conceptually illustrates the concentration discontinuity on both sides of the electrolyte ion-blocking layer 505. With the electrolyte ion-blocking layer 505, the combined concentration of the small electrolyte ions are significantly smaller in the nanoporous layer 117 than in the biocompatibility layer 507. Without the electrolyte ion-blocking layer 505, the combined concentration of the small electrolyte ions in the nanoporous layer 117 would be similar to that in the biocompatibility layer 507.

Concentration of Small Electrolyte Ions under Electrolyte Ion-Blocking Layer

In embodiments, the combined concentration of the electrolyte ions below the electrolyte ion-blocking layer 505 is greater than 0% but lower than about 1, 2, 3, 4, 5, 6, 7, 8, 9, 10, 11, 12, 13, 14, 15, 16, 17, 18, 19 or 20% of the combined concentration of the same electrolyte ions above the electrolyte ion-blocking layer 505. The combined concentration below the electrolyte ion-blocking layer 505 may be within a range formed by selecting any two numbers (two % values) listed in the immediately previous sentence. As illustrated in FIG. 32, for example, the combined concentration of the electrolyte ions in human interstitial bodily fluid (i.e., above the electrolyte ion-blocking layer 505) is about 0.1 M or higher; in contrast, the combined concentration of the electrolyte ions below the electrolyte ion-blocking layer 505 is about 0.01 M or lower. The combined concentration of the electrolyte ions below the electrolyte ion-blocking layer 505 may be obtained by measuring double-layer capacitance of the nanoporous layer 117 and applying the measured value to the Gouy-Chapman formula, as discussed in detail in *Ionic Strength-Controlled Virtual Area of Mesoporous Platinum Electrode*, Boo et al, J. AM. CHEM. Soc. 2004, 126, 4524-4525.

Acceleration of Ionic Equilibrium in Nanoporous Layer

As discussed, the ion-blocking layer 505 establishes or creates a substantial discontinuity in the combined concentration of the small electrolyte ions between over the electrolyte ion-blocking layer 505 and under the same layer. The low concentration of the small electrolyte ions significantly excels conditioning of the CGM working electrode 501, particularly conditioning of the nanoporous layer 117. Although any aspects of the invention are not bound by any theory or belief, the low concentration of the small electrolyte ions may accelerate ionic equilibrium in nano-sized structures and surfaces of the nanoporous layer 117 that would not occur in larger scale such as micro-sized structures and surfaces. As the ionic equilibrium is accelerated in the nanoporous layer 117, the time for reaching ionic equilibrium or steady state inside the nano-structures of the nanoporous layer 117 would be shorter at a lower concentration of the electrolyte ions with the existence of the electrolyte ion-blocking layer 505 than at a higher concentration without the electrolyte ion-blocking layer 505.

Significantly Shorter Time for Conditioning

With the acceleration of ionic equilibrium in the nanoporous layer 117, the electrolyte ion-blocking layer 505 significantly enhances and facilitates conditioning of the non-enzymatic CGM working electrode 501 of FIG. 31, i.e., shortening the time for reaching a desirable electric current and/or a desirable rate of electric current change, i.e., steady state. According to embodiments, a fraction of time is needed for the completion of conditioning when using a non-enzymatic CGM working electrode 505 with the electrolyte ion-blocking layer 505 compared to when using the same non-enzymatic CGM working electrodes without an electrolyte ion-blocking layer 505.

Conditioning Time

When the desirable rate of electric current change is 5 nA/min or less, a non-enzymatic CGM working electrode without an electrolyte ion-blocking layer 505 take about 3 hours in serum that contains electrolyte ions at 0.1 M or higher; in contrast, a non-enzymatic CGM working electrode with an electrolyte ion-blocking layer 505 takes less than at or about 1 hour and 30 minutes, 1 hour and 25 minutes, 1 hour and 20 minutes, 1 hour and 15 minutes, 1 hour and 10 minutes, 1 hour and 5 minutes, 1 hour, 55 minutes, 50 minutes, 45 minutes, 40 minutes, 35 minutes, or 30 minutes in the same serum. When the desirable rate of electric current change is 3 nA/min or less, a non-enzymatic CGM working electrode without an electrolyte ion-blocking layer 505 take more than 5 hours in serum that contains electrolyte ions at 0.1 M or higher; in contrast, a non-enzymatic CGM working electrode with an electrolyte ion-blocking layer 505 takes less than at or about 1 hour and 30 minutes, 1 hour and 25 minutes, 1 hour and 20 minutes, 1 hour and 15 minutes, 1 hour and 10 minutes, 1 hour and 5 minutes, 1 hour, 55 minutes, 50 minutes, 45 minutes, 40 minutes, 35 minutes, 30 minutes, 25 minutes, 15 minutes or 10 minutes in the same serum. When the desirable rate of electric current change is 2 nA/min or less, a non-enzymatic CGM working electrode without an electrolyte ion-blocking layer 505 take more than 5 hours or 10 hours in serum that contains electrolyte ions at 0.1 M or higher; in contrast, a non-enzymatic CGM working electrode with an electrolyte ion-blocking layer 505 takes less than at or about 1 hour and 30 minutes, 1 hour and 25 minutes, 1 hour and 20 minutes, 1 hour and 15 minutes, 1 hour and 10 minutes, 1 hour and 5 minutes, 1 hour, 55 minutes, 50 minutes, 45 minutes, 40 minutes, 35 minutes, 30 minutes, 25 minutes, 15 minutes or 10 minutes in the same serum.

Unexpected Results

Without proper conditioning, a CGM working electrode may not provide electric current for an accurate glucose level. Reducing the time for conditioning is a very important practical consideration in developing and manufacturing a CGM working electrode. This is because proper conditioning of a CGM working electrode may take hours, if not tens of minutes, and because there is a tendency that people would want to know their glucose level immediately after inserting the electrode in their body. Referring to examples discussed later, the time for conditioning CGM working electrode is reduced from about 3, 5 or 10 hours to less than 30 minutes by including an electrolyte ion-blocking layer 505 alone with all the other conditions being the same. This is very significant improvement and unexpectedly high achievement.

Specifics of Electrolyte Ion-Blocking Layer

The electrolyte ion-blocking layer 505 of a non-enzymatic CGM working electrode includes or is made of at least one porous, hydrophobic polymer including poly(methyl methacrylate) (PMMA), poly(hydroxyethyl methacrylate) (PHEMA), and poly(methyl methacrylate-co-ethylene glycol dimethacrylate) (PMMA-EG-PMMA). Additional examples of the porous, hydrophobic polymer include a copolymer of methylmethacrylate and butylmethacrylate, and polymers obtained from polymerization of one or more monomers including methylmethacrylate, ethylmethacrylate, propylmethacrylate, butylmethacrylate, pentylmethacrylate, hexylmethacrylate, cyclohexylmethacrylate, 2-ethylhexylmethacrylate, methylacrylate, ethylacrylate, propylacrylate, butylacrylate, pentylacrylate, hexylacrylate, cyclohexylacrylate, 2-ethylhexylacrylate, etc. The average molecular weight for these polymers is about 5,000, 10,000, 20,000, 30,000, 40,000, 50,000, 60,000, 70,000, 80,000, 90,000, 100,000, 110,000, 120,000, 130,000, 140,000, 150,000, 160,000, 170,000, 180,000, 190,000, 200,000, 210,000, 220,000, 230,000, 240,000, 250,000, 260,000, 270,000, 280,000, 290,000, 300,000, 310,000, 320,000, 330,000, 340,000, 350,000, 360,000, 370,000, 380,000, 390,000 or 400,000. In embodiments, the molecular weight may be within a range formed by selecting any two numbers listed in the immediately previous sentence. The electrolyte ion-blocking layer may have a thickness of about 0.1, 0.5, 1, 1.5, 2, 2.5, 3, 3.5, 4, 4.5, 5, 5.5, 6, 6.5, 7, 7.5, 8, 8.5, 9, 9.5 or 10 In embodiments, the thickness may be within a range formed by selecting any two numbers (two thickness values) listed in the immediately previous sentence, e.g., between about 2 and about 5 μm, ranging between about 1 and about 3 μm, etc.

Ion Concentration Drop has No Effect in Enzymatic Glucose Sensing Electrode

In an enzymatic CGM system, a CGM working electrode includes a glucose-specific enzyme for oxidation of glucose molecules. The enzymatic CGM working electrode may include a functional layer containing a porous, hydrophobic material that may effectively drop concentration of electrolyte ions under the functional layer. In the enzymatic CGM system, however, the concentration drop by the functional layer may not provide a reduction of the time for conditioning of the CGM electrode that relates to ionic equilibrium in nano-sized surfaces or structures. This is because the enzymatic CGM system uses enzymes for oxidizing glucose molecules and does not require a nanoporous layer for glucose oxidation. Accordingly, even if a porous, hydrophobic layer is included in an enzymatic CGM working electrode, even if such a layer causes discontinuity of electrolyte ion concentration across its thickness, and further even if there is some reduction of time for conditioning of the enzymatic CGM working electrode, such reduction would not be equated to the reduction of time for conditioning in the non-enzymatic CGM working electrode 501 having both the electrolyte ion blocking layer 505 and nanoporous layer 117.

CGM Subcutaneous Electrode Module

CGM Electrode Unit

In embodiments, the CGM system includes an electrode unit or module for subcutaneously contracting bodily fluid of a subject. The electrode unit may include a single body accommodating one or more electrodes that would contact the bodily fluid when inserted into the subject's body. The single body may be flexible.

Construction of CGM Electrode Unit

Figure 33:
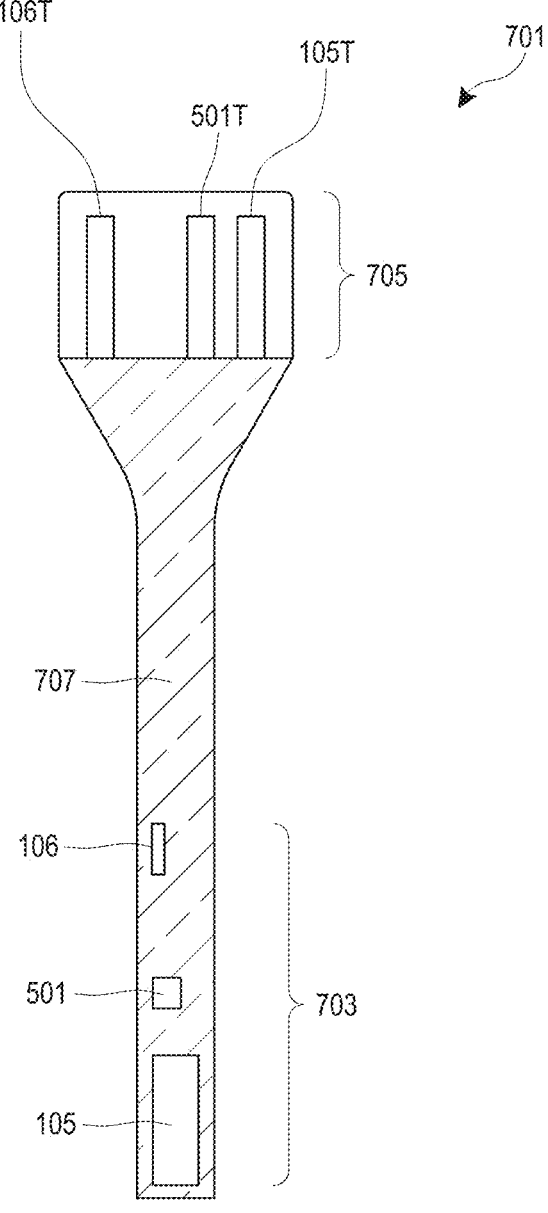
FIG. 33 illustrates a CGM electrode unit according to an embodiment.

FIG. 33 illustrates a CGM electrode unit 701 according to an embodiment. The CGM electrode unit 701 includes a subcutaneous portion 703 and a contact terminal portion 705. The subcutaneous portion 703 is for inserting into the subject's body and includes a working electrode 501, a counter electrode 105 and a reference electrode 106 that are exposed via openings formed through an insulating layer 707 for subcutaneously contacting bodily fluid. The contact terminal portion 705 is for staying outside the subject's body and for engaging or connecting with a counterpart device. The contact terminal portion 703 includes a working electrode terminal 501T, a counter electrode terminal 105T and a reference electrode terminal 106T that are electrically connected to the working electrode 501, counter electrode 105 and reference electrode 106, respectively, underneath the insulation layer 707. Here, each of the working electrode 501, counter electrode 105 and reference electrode 106 may have features and characteristics as discussed in the present disclosure, although not limited thereto.

Fabricating CGM Electrode Unit

Figure 34:
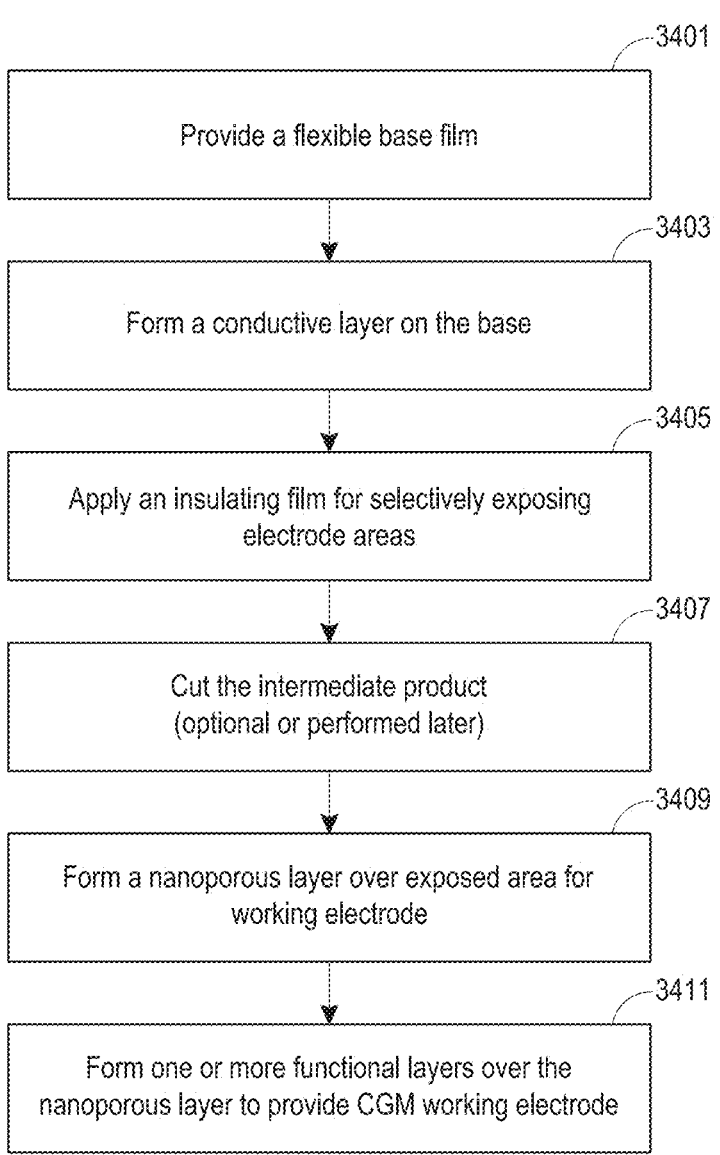
FIG. 34 is a flowchart for fabricating a CGM electrode unit according to an embodiment.
Figure 35:
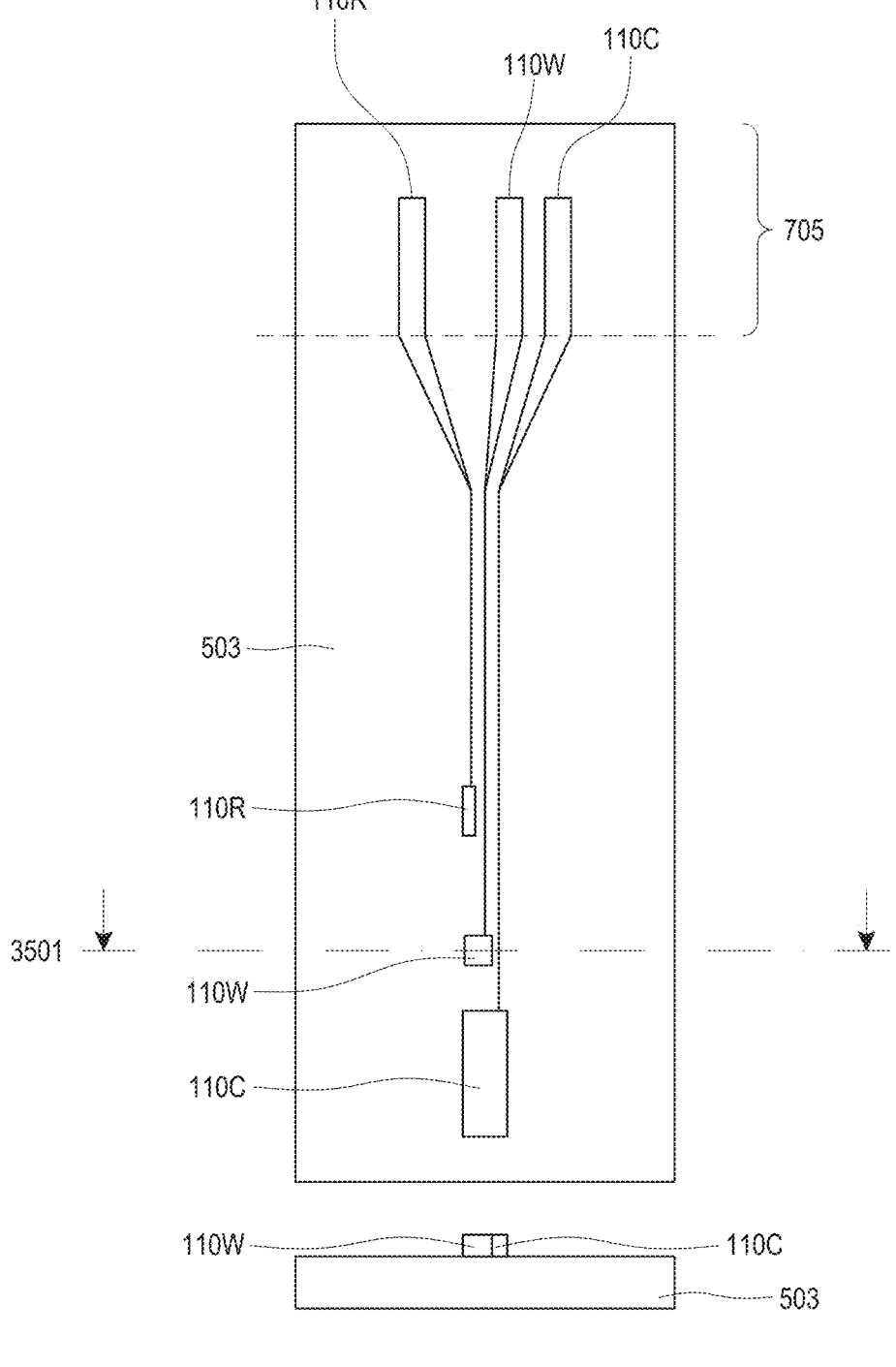
FIGS. 35-37 illustrate top and cross-sectional views of intermediate products at various stages of fabricating the CGM electrode of FIG. 33, in which each cross-section is taken along the line 3501 and viewed in the arrow direction.

FIG. 34 is a flowchart for fabricating the CGM electrode unit 701 according to an embodiment. At step 3401, an electrically insulative, flexible film is provided for a base or electrode base 503 (also in FIG. 31). Subsequently at step 3403, a conductive layer is formed on the base 503 in predetermined shapes 110R, 110W and 110C as illustrated in FIG. 35. Subsequently as step 3405, an insulation film 707 is applied over the conductive layer to selectively expose portions or areas of the conductive layer as in FIG. 36. Subsequently at step 3407, the intermediate product is cut to provide the shape as illustrated in FIG. 37. At step 3409, a nanoporous layer 117 is formed on an exposed area for the working electrode 501. Subsequently at 3411, one or more functional layers are formed on the nanoporous layer 117 to provide a laminated construction of the non-enzymatic CGM working electrode 501 as in FIG. 31. Further, a salt layer may be formed on the exposed area for the reference electrode 106. In embodiments, cutting the intermediate product at step 3407 may be performed after step 3409 or 3411.

Conductive Layer—Multiple Conductive Elements

FIG. 35 provides a top view of an intermediate product after step 3403 according to an embodiment and its cross-section taken along the line 3501 and viewed in the arrow direction. As illustrated, the conductive layer formed on the base 503 has three separate elements 110C, 110W and 110R in predetermined shapes, i.e., conductive layer element 110C for counter electrode, conductive layer element 110W for working electrode, and conductive layer element 110R for reference electrode. Each of the conductive layer elements 110C, 110W and 110R includes a conductive portion reserved for a contact terminal (in the contact terminal portion 705 of FIG. 33), a conductive portion reserved for an electrode (in the subcutaneous portion 703 of FIG. 33), and a conductive connection between the two conductive portions.

Making Conductive Layer

The conductive layer may be in a single layer of an electrically conductive material or formed of multiple sublayers of different conductive materials. In embodiments, either or both of the conductive layer element 110C for counter electrode and the conductive layer element 110W for working electrode are formed of at least two sublayers, e.g., a silver layer and a conductive carbon layer over the silver layer. In embodiments, the conductive layer element 110R for reference electrode is formed in a single layer, e.g. a silver layer. The conductive layer 110 or its sublayers may be formed by printing a conductive ink on or over the base 503 and subsequent drying. A sublayer formed on another sublayer may be also formed by printing a conductive material for that sublayer. The conductive layer elements 110W, 110C and 110R of FIG. 35 are all in a single layer; for the purpose of showing alternatives, however, in FIGS. 36-38, the conductive layer elements 110W and 110C have a two-sublayer construction, i.e., carbon layer 1605 over silver layer 1603 (see also FIG. 16A).

Insulation Film

Figure 36:
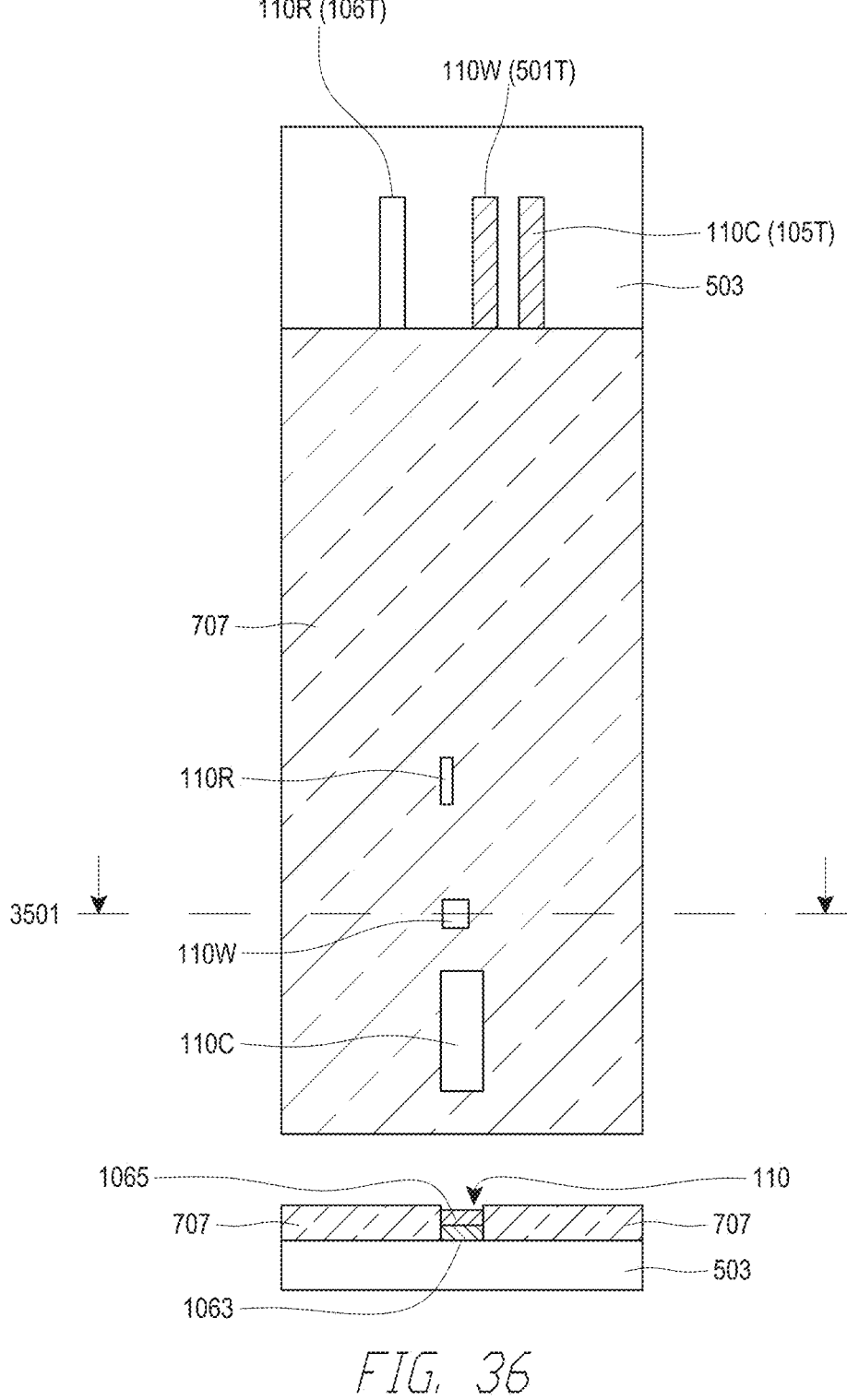
Figure 37:
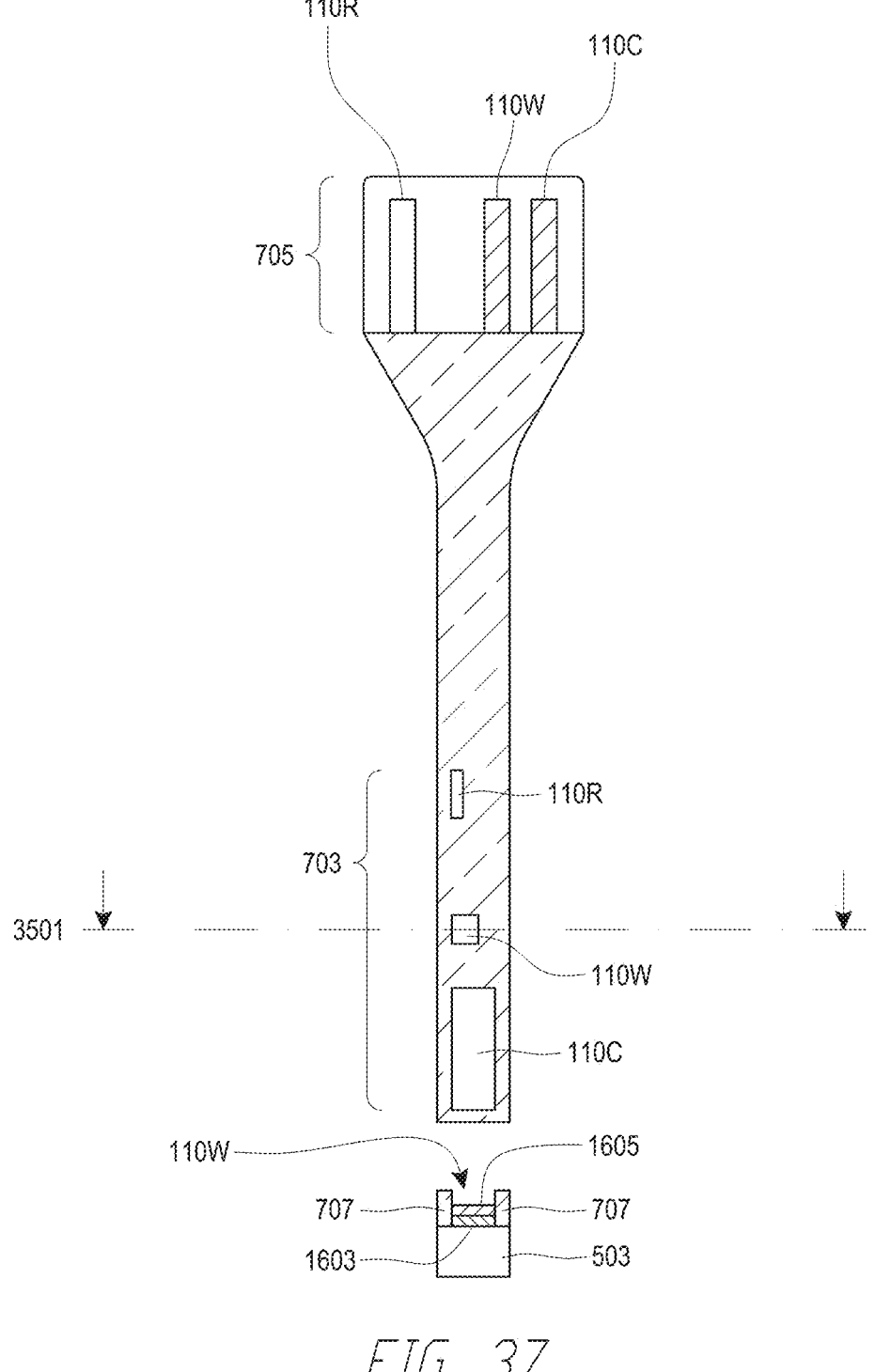

FIG. 36 illustrates an intermediate product after placing the insulation film according to an embodiment. The insulation film 707 may be pre-cut with openings in the subcutaneous portion 703 of FIG. 33 for exposing conductive portions reserved for the counter electrode 105, working electrode 501 and reference electrode 106. The insulating film 707 does not cover the contact terminal portion 705 of FIG. 33 and accordingly exposes the terminal portion of each of the conductive layer elements 110C, 110W and 110R, which become 105T, 501T and 106T, respectively. The conductive connections of the conductive layer elements 110C, 110W and 110R are covered with the insulation film 707. An adhesive layer (not illustrated) may be interposed between the base film 503 and the insulation film 707. The insulation film 707 may be an adhesive-coated film.

Cutting

At step 3407, the intermediate product of FIG. 36 is subject to cutting to remove unnecessary portions of the insulation film 707 and base 503, for example, by die cutting. FIG. 37 illustrates the resulting product, in which the contact terminal portion 705 (proximal end portion of the CGM electrode unit 701) is wider than the subcutaneous portion 703 (distal end portion of the CGM electrode unit 701). In embodiments, the distal portion has a width of about 0.5, 0.6, 0.7, 0.8, 0.9, 1.0, 1.1, 1.2, 1.3, 1.4, 1.5, 1.6, 1.7, 1.8, 1.9 or 2.0 mm in the direction along the line 3501. In embodiments, the width may be within a range formed by selecting any two numbers listed in the immediately previous sentence, e.g., between about 1.0 mm and about 1.5 mm. In embodiments, the CGM electrode unit 701 has a length of about 4, 5, 6, 7, 8, 9, 10, 11, 12, 13, 14, 15, 16, 17, 18, 19, 20, 21, 22, 23, 24, 25, 26, 27, 28, 29 or 30 mm in a direction between the distal end and proximal end thereof. In embodiments, the length may be within a range formed by selecting any two numbers listed in the immediately previous sentence, e.g., between about 10 mm and about 20 mm.

Forming Nanoporous Layer

Figure 38A:
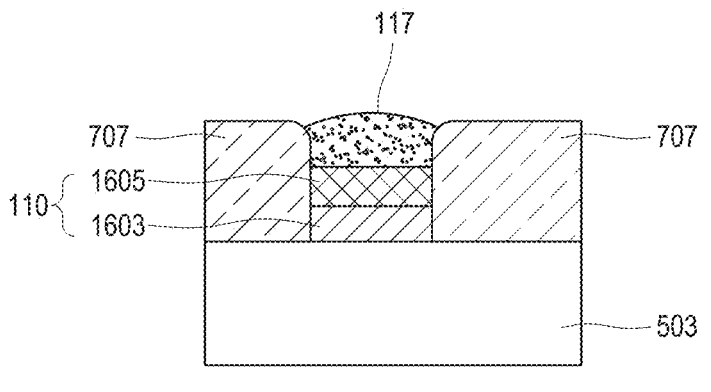
FIGS. 38A and 38B illustrate a cross-section of an intermediate product after forming nanoporous layer and a CGM working electrode with functional layers, respectively, according to embodiments.

At step 3409, a nanoporous layer 117 is formed on the conductive layer element 110W exposed for working electrode. FIG. 38A illustrates a cross-section of the intermediate product taken along the line 3501 in the arrow direction after forming the nanoporous layer 117. In embodiments, the nanoporous layer 117 is formed by dispensing cluster colloid containing nanoparticle clusters dispersed in liquid over the conductive layer 110 and drying the liquid off therefrom. In the alternative, another form of the nanoporous layer 117 may be formed using a different method as disclosed herein. In some embodiments, cutting at step 3407 may be performed subsequent to forming the nanoporous layer 117.

Functional Layer(s) for Working Electrode

Figure 38B:
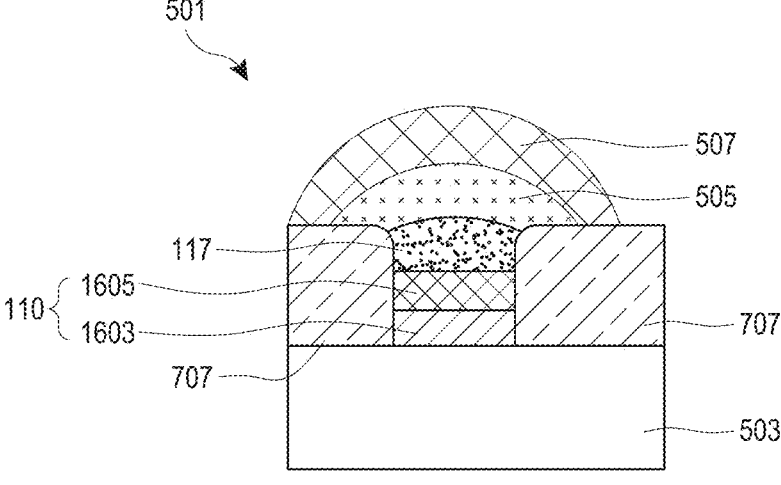

Subsequent to forming the nanoporous layer 117, one or more functional layers are formed on the nanoporous layer 117 to provide the non-enzymatic CGM working electrode 501 as in FIG. 31. A maltose blocking layer 301 may be formed on the nanoporous layer 117, although not limited thereto. An electrolyte ion-blocking layer 505 may be formed over the nanoporous layer 117 for the improvement in conditioning the resulting CGN working electrode 501, although not limited thereto. Further, a biocompatibility layer 507 may be formed over the nanoporous layer 117, more specifically over the electrolyte ion-blocking layer 505, although not limited thereto. FIG. 38B illustrates a cross-section of the CGM working electrode 501 including electrolyte ion-blocking layer 505 and biocompatibility layer 507.

Reference and Counter Electrodes

In embodiments, a salt layer, e.g., AgCl may be formed on the conductive layer element 110R exposed for the reference electrode 106. Forming the salt layer may be performed any time after forming the conductive layer element 110R. In embodiments, the counter electrode 105 may not require an additional treatment over the conductive layer element 110C.

Subcutaneous Insertion of CGM Electrode Unit

In embodiments, the subcutaneous portion 703 (distal portion) of the CGM electrode unit 701 is subcutaneously inserted into the subject's body with or without use of an insertion tool that is known in the art or will be developed in the future. With proper subcutaneous insertion, the working electrode 501, reference electrode 106 and counter electrode 105 of the subcutaneous portion 703 contact the subject's interstitial bodily fluid while the terminal portion 705 of the CGM electrode unit 701 stays outside the subject's body.

Counterpart Device

Subsequently, in embodiments, the terminal portion 705 is engaged or connected with a counterpart device (not illustrated) that includes counterpart ports or terminals corresponding to the working electrode terminal 501T, counter electrode terminal 105T and reference electrode terminal 106T. In embodiments, the counterpart device further includes an electrical circuit that completes the electrochemical cell of FIG. 1 together with the CGM electrode unit 701 for continuous monitoring glucose module. In some embodiments, in addition to the electrical circuit for completing an electrochemical cell, the counterpart device may include at least one processor for processing data including electric current obtained from the electrochemical cell to convert to a standardized number representing a glucose level. In some embodiments, the counterpart device includes a wireless module for wirelessly sending data to another wireless device such as a smartphone or computing device.

BGM Disposable Strip

Single Point in Time Devices

Glucose sensing may be performed in vitro at a single point in time. A single-point-in-time glucose-sensing system measures a glucose level in a test fluid, most commonly blood. Accordingly, the system is referred to as a blood glucose monitoring (BGM) system. The BGM systems include a single-use disposable cartridge or strip.

Disposable Cartridge

Figure 39:
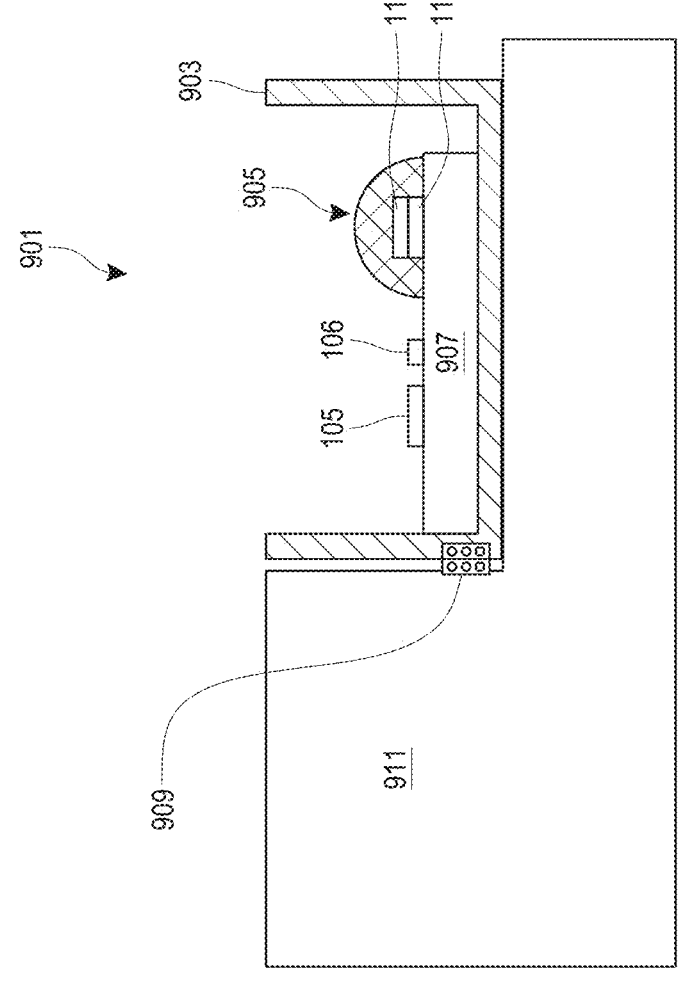
FIG. 39 illustrates a disposable glucose-sensing cartridge according to embodiments.

FIG. 39 illustrates a BGM disposable cartridge 901 and a sensing module 911 for a single-point-in-time glucose-sensing system according to embodiments. The disposable cartridge 901 includes a test fluid reservoir 903, a counter electrode 105, a reference electrode 106, and a cartridge working electrode 905 formed on a base 907 that provides a structural support for the electrodes 105, 106 and 905. Electric connections (not shown) are formed between the electrodes and a connector 909 through the base 907.

Sensing Module

In embodiments, the disposable cartridge 901 is designed to electrically and/or mechanically couple with the sensing module 911 via the connector 909. The sensing module 911 may include electric circuitry (not shown) for a voltage source 109 and a current sensor 108. When the disposable cartridge 901 is properly connected to the sensing module 911, the electrodes 105, 106 and 905 are connected to the circuit of the sensing module 911 in a manner similar to FIG. 1.

Working Electrode

The working electrode 905 according to an embodiment, which includes a conductive layer 110 and a nanoporous layer 117. The working electrode 905 further includes a filter layer 913 to filter and screen cells, lipid and large molecules contained in the test fluid. In embodiments, the filter layer 913 may be made of or include woven cloth, cotton or other materials that can screen cells, lipid and other large components of blood while passing glucose therethrough.

Working Electrode does not Include

In embodiments, the working electrode 905 contains no glucose-specific enzyme. Further, the working electrode 905 contains no surfactant and no electron mediator that may be necessary in enzymatic glucose sensing. Further, given that the working electrode 905 is an in vitro device, it does not require a biocompatibility layer either.

Calibration of Working Electrode

Electric Current from Working Electrode

According to embodiments, the non-enzymatic working electrode with a nanoporous glucose-oxidation layer generates electric current caused by oxidation of glucose contained in a test liquid. In practice, the electric current from the non-enzymatic working electrode includes 1) electric current caused by glucose oxidation alone (glucose-oxidation current), 2) electric current caused by interfering chemical entities if the test fluid contains such, and 3) electric current caused by interactions between the electrochemical cell and other chemical entities contained in the test fluid.

Glucose Levels in Bodily Fluid

Normal glucose levels in healthy individuals are between 4.0 and 6.0 mM (between 72 and 108 mg/dL). Considering diabetic patients, the glucose levels may range between 4.0 and 20 mM (between 72 and 360 mg/dL).

Glucose-Oxidation Current

In embodiments, at steady state (after conditioning) in a test fluid containing 4.0-20 mM glucose, when applying a bias voltage between about 0.2 V and about 0.45 V, the electric current from glucose oxidation alone (glucose-oxidation current) is at a level higher than 10 nA/mMcm$^2$. In the glucose concentration range of 4.0-20 Mm, the nanoporous glucose-oxidation layer (hence, the non-enzymatic working electrode) generates the glucose-oxidation current at about 0.5, 1.0, 1.5, 2.0, 2.5, 3.0, 3.5, 4.0, 4.5, 5.0, 5.5 or 6.0 nA for 1 mM of glucose contained in the test fluid. In embodiments, the glucose-oxidation current from 1 mM of glucose contained in the test fluid may be within a range formed by any two numbers in the immediately preceding sentence, e.g., between about 1.5 nA and 2.5 nA. Accordingly, for the glucose concentration range of 4.0-20 mM, the glucose-oxidation current from the non-enzymatic working electrode may be between about 2.0 nA (4.0×0.5) and about 120 nA (20×6.0). In embodiments, the glucose-oxidation current may be about 2.0, 4.0, 8.0, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118 or 120 Na. In embodiments, the glucose-oxidation current from 4.0-20 mM glucose contained in the test fluid may be within a range formed by any two numbers in the immediately preceding sentence, e.g., between about 1.5 nA and 2.5 nA.

Calibration of Electric Current and Glucose Concentration

In embodiments, for the same glucose concentration in the test fluid, the glucose-oxidation current may differ from one nanoporous glucose-oxidation layer to another, depending upon their particular manufacturing conditions. Also, in a particular nanoporous glucose-oxidation layer, the glucose-oxidation current is generally linearly correlated with the glucose concentration, although it may not be so linear throughout the concentration or electric current range. In embodiments, for each batch of nanoporous glucose-oxidation layers manufactured using the same of conditions, one or more nanoporous glucose-oxidation layers are tested to determine the correlation profile between glucose-oxidation current and glucose concentration for the particular batch. Later in the process of glucose sensing or monitoring using a nanoporous glucose-oxidation layer from the same batch, the correlation profile is used in computing or determining a glucose level in a test fluid.

Second Working Electrode

Ascorbic Acid

Ascorbic acid is known as Vitamin C and plays an important role in the human body. Ascorbic acid is prone to oxidation and is readily oxidized at a low oxidation potential. Ascorbic acid may interfere with glucose sensing from bodily fluid.

Currently No Layer Available for Blocking Ascorbic Acid

Given that ascorbic acid is negatively charged, a negatively charged layer has been proposed to repel ascorbic acid while passing glucose. However, no glucose-sensing electrode is commercially available to block ascorbic acid so far.

Two Working Electrodes

Figure 40:
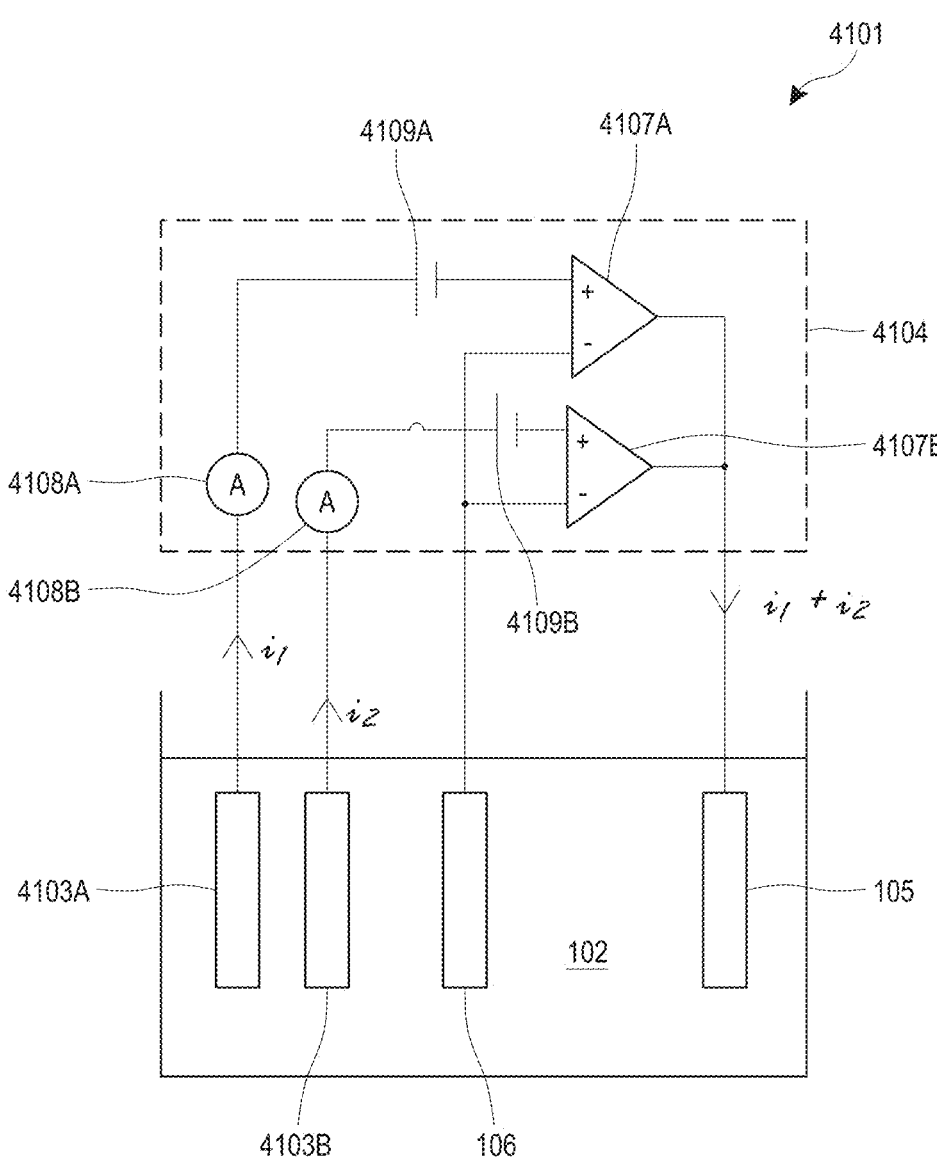
FIG. 40 illustrates a two-electrode glucose-sensing system according to an embodiment.

In embodiments, a glucose sensor or sensing system includes at least one additional working electrode in addition to the working electrode 103 of FIG. 1. FIG. 40 conceptually illustrates a two-working electrode glucose-sensing system 4101. In this system, a first working electrode 4103A, a second working electrode 4103B, a counter electrode 105 and a reference electrode 106 are connected to a potentiostat 4104, which includes electric circuitry for functioning as op-amps 4107A and 4107B, current sensors 4108A and 4108B, and voltage sources 4109A and 4109B for the two working electrodes 4103A and 4103B.

Operation of Two-Working Electrode System

In embodiments, oxidation of both glucose and ascorbic acid occurs at the first working electrode 4103A. Accordingly, electric current from the first working electrode 4103A represents the combined concentration of glucose and ascorbic acid in the test fluid 102. On the other hand, at the second working electrode 4103B, oxidation of the ascorbic acid occurs but oxidation of glucose does not occur. Accordingly, electric current from the second working electrode 4103B represents only the concentration of ascorbic acid in the same test fluid 102. The difference between the two electric current values represents the concentration or level of glucose contained in the test fluid 102.

First Working Electrode (Glucose Working Electrode)

In some embodiments, the first working electrode (glucose working electrode) 4103A includes the nanoporous layer 117 over the conductive layer 110, as in FIG. 3. The nanoporous layer 117 may include clustered nanoporous structure, although not limited thereto. In other embodiments, the first working electrode 4103A may include an enzyme layer containing glucose-specific enzyme for oxidizing glucose, as in FIG. 2, instead of the nanoporous layer 117 of FIG. 3. In either embodiment, the first working electrode 4103A does not include a negatively charged membrane or any other membrane for inhibiting ascorbic acid from passing therethrough.

Second Working Electrode (No-Glucose Working Electrode)

The second working electrode (no-glucose working electrode) 4103B includes a conductive layer 110 but does not include any layers or features for effectively causing oxidation of glucose. In embodiments, the second working electrode 4103B includes neither the nanoporous layer 117 nor a glucose-specific enzyme for oxidizing glucose. However, oxidation of ascorbic acid occurs at the conductive layer 110. In embodiments, the conductive layer 110 includes a conductive carbon layer formed on a silver layer, although not limited thereto.

The Same Bias Voltage for Two Electrodes

In embodiments, the same bias voltage is applied to both the first and second working electrodes 4103A and 4103B relative to the reference electrode 106. This is to provide an environment to cause about the same level of oxidation of ascorbic acid to occur at both the first and second working electrodes 4103A and 4103B. Assuming the same level of oxidation occurs for ascorbic acid at each of the first and second working electrodes 4103A and 4103B, the difference between electric current from the first working electrode 4103A and electric current from the second working electrode 4103B should represent the oxidation of glucose at the first working electrode 4103A.

Addressing Interference of Additional Chemical Entities

The two-electrode system 4101 can be used to address the interference of more than one chemical entity. In embodiments, by adjusting the bias voltage, the first working electrode 4103A may oxidize not only glucose and ascorbic acid but also an additional interfering chemical entity such as acetaminophen. Likewise, the second working electrode 4103B oxidizes not only ascorbic acid but also the additional interfering chemical entity at the same time. Here, neither of the first and second working electrodes includes any membrane for inhibiting the additional interfering chemical entity. Then, the electric current from the first working electrode 4103A represents oxidation of glucose, ascorbic acid and acetaminophen, and the electric current from the second working electrode 4103B represents oxidation of ascorbic acid and acetaminophen. The difference between the electric currents represents oxidation of glucose, cancelling off the interference of acetaminophen and ascorbic acid.

Bias Voltage

In embodiments, any bias voltage value within the range of 0.2-0.45 V may be used for addressing the interference. In some embodiments, a bias voltage value within the range of 0.2-0.32 V may be used for addressing the interference of ascorbic acid alone given that acetaminophen may not be oxidized in the nanoporous metal layer at that bias voltage range as discussed in more detail below.

Different Bias Voltages

In embodiments, the two-electrode system 4101 may adopt different bias voltages for the first and second working electrodes. For example, a first bias voltage is applied to the first working electrode 4103A, and a second bias voltage is applied to the second working electrode 4103B. With the different bias voltages, the electric current from oxidation of ascorbic acid at the second working electrode 4103B may not be the same or equivalent to the current component by oxidation of ascorbic acid at the first working electrode 4103A. Thus, the current from glucose oxidation may not be the simple difference between the currents from the two electrodes. In embodiments, however, the two-electrode system 4101 has or is connected to hardware and software for computing an accurate glucose concentration using the different bias voltages, the current values from the first and second working electrodes 4103A and 4103B, data indicative of oxidation potential of ascorbic acid at the different bias voltages, etc.

Concomitant Detections

In some embodiments, detection of the current from the first working electrode 4103A and detection of the current from the second working electrode 4103B occur at the same time, simultaneously, concurrently or concomitantly. In other embodiments, either with one current sensor or two current sensors, the detections may occur at different times with a time gap as long as the concentration fluctuation of the concerned chemical entities is negligible over the time gap. Skilled artisans in the art would appreciate how long the time gap can be without too much of the risk of being inaccurate. For example, the time gap is less than 1, 2, 3, 4, 5, 6, 7, 8, 9 or 10 seconds, or the time gap is less than 1, 2, 3, 4, 5, 6, 7, 8, 9 or 10 minutes.

Recording Concentration of Interfering Chemical

In embodiments, the two-electrode system 4101 includes or is to be connected to hardware and software (not shown) that is configured to store current values from the first and second working electrodes 4103A and 4103B and/or to store respective concentrations of glucose and ascorbic acid obtained from the current values. In some embodiments where oxidation of both ascorbic acid and acetaminophen occurs at the second working electrode 4103B, the hardware and software is configured to store the concentration of glucose and a combined concentration of ascorbic acid and acetaminophen.

Applicable to CGM

Figure 41:
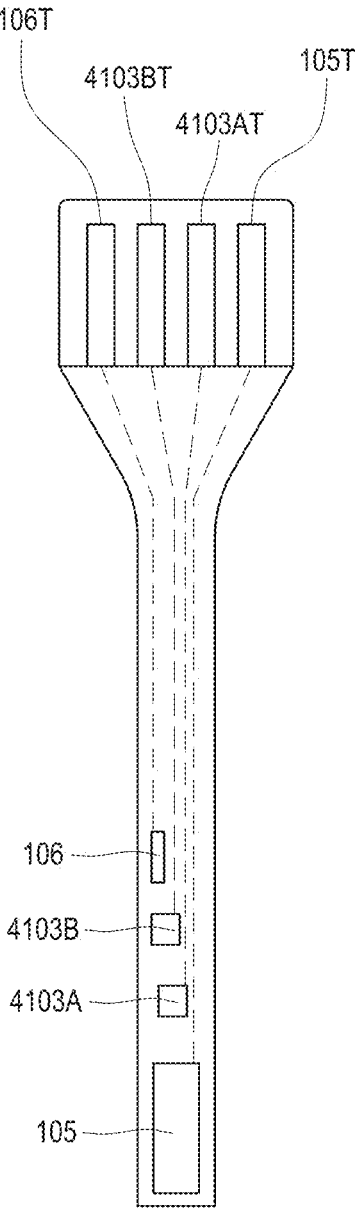
FIG. 41 illustrates a CGM electrode unit for a two-electrode glucose-sensing system according to an embodiment.

The two-electrode system 4101 may be implemented in a CGM electrode unit for in vivo glucose sensing. FIG. 41 illustrates a CGM electrode unit 4201 including the first and second working electrodes 4103A and 4103B, which are connected to first and second working electrode terminals 4103AT and 4103BT respectively.

Applicable to BGM

The two-electrode system 4101 may be implemented in a BGM disposable cartridge or strip for in vitro glucose sensing. In embodiments, the disposable cartridge 901 of FIG. 39 may include two working electrodes. In such embodiments, the cartridge working electrode 905 works as the first working electrode 4103A. The second working electrode 4103B may be added to the base 907 for contacting the test fluid. Further, the corresponding sensing module 911 may include circuitry for receiving signals from the first and second working electrodes from the BGM disposable cartridge.

First and Second Working Electrodes Must Operate Together

In the two-electrode system 4101, there must be two current values: one from the first working electrode 4103A and the other from the second working electrode 4103B in order to obtain a glucose level in the test fluid. For CGM, each of the first and second working electrodes 4103A and 4103B must operate continuously or repeatedly to provide glucose levels. Accordingly, the system is distinguished from any electrochemical sensing systems having a spare sensing electrode that is occasionally used for various reasons.

Interference by Acetaminophen

Acetaminophen

Acetaminophen is one of the most commonly used over-the-counter medications. Further, acetaminophen is widely used in combinational drugs as an active pharmaceutical ingredient.

Well-Recognized Problem

Given the popularity of acetaminophen, it is possible that the drug can be taken by patients who also need to detect their blood glucose level. Considering that many glucose sensing devices are used by patients themselves, not by healthcare professionals, incorrect readings caused by acetaminophen can lead to serious consequences. The industry for electrochemical glucose sensing has known this problem and been interested in solving it.

No Good Solution

There have been many attempts to solve this problem. Thus far, however, no solution has convinced the industry to adopt. No membrane has been adopted to selectively screen acetaminophen from reaching the electrode. Thus, there is a long-felt-but-unmet need.

Explanation for No Good Solution

The commercially available electrochemical glucose sensing technologies simply cannot address this issue at all. This is at least in part because electrochemical glucose-sensing systems are technically very complex. The working electrode has laminated components, each of which has its own function and does not interfere with the other components. It would be difficult to find a solution addressing this problem involving acetaminophen without affecting the functions of other components and overall performance of the working electrode. In addition to the technical complexity, developing a product like this for market launching is very expensive in view of the rigorous regulatory approval process in this industry. Accordingly, once a working product has been approved and launched in the market, significant changes to any working component of the approved product would be difficult to make.

Non-enzymatic Glucose-Sensing System Addressing Acetaminophen

In embodiments, a non-enzymatic electrochemical glucose-sensing system selectively oxidizes glucose and at the same time does not oxidize acetaminophen without introducing any additional membrane for this result. Referring back to FIGS. 3 and 31, the working electrode 103NE, 501 includes the conductive layer 110 and the nanoporous layer 117. The working electrode may include one or more additional functional layers over the nanoporous layer 117.

No Acetaminophen Screening Membrane

In embodiments, the working electrode 103NE does not include, over the nanoporous layer 117, a membrane, film or layer that is designed to selectively screen, repel or block acetaminophen while allowing glucose to pass therethrough. Thus, when the working electrode 103NE contacts the test fluid containing acetaminophen, both glucose and acetaminophen will contact the nanoporous layer 117 and will be able to enter nano-sized pores for oxidation therein.

Bias Voltages for Oxidation of Glucose and Acetaminophen

In the glucose-sensing system according to embodiments, glucose is oxidized in the nanoporous layer 117 at a bias voltage between about 0.2 V and about 0.45 V. On the other hand, acetaminophen is oxidized at a bias voltage greater than 0.33, 0.34, 0.35 or 0.36 V. The bias voltage may be adjusted to cause oxidation of glucose and to avoid oxidation of acetaminophen at the same time.

Bias Voltage for Selective Oxidation of Glucose and No Oxidation of Acetaminophen In embodiments, the bias voltage applied to the conductive layer 110 relative to the reference electrode 106 is set to cause oxidation of glucose but not to cause oxidation of acetaminophen when both contact the nanoporous layer 117. For selective oxidation of glucose and selective non-oxidation of acetaminophen, in embodiments, the bias voltage is set at or about 0.20, 0.21, 0.22, 0.23, 0.24, 0.25, 0.26, 0.27, 0.28, 0.29, 0.30, 0.31 or 0.32 V. In embodiments, the bias voltage may be within a range formed by selecting any two numbers (two voltage values) listed in the immediately previous sentence, e.g., between 0.28 V and 0.30 V, between about 0.27 V and about 0.31 V, between 0.26 V and 0.30 V, between about 0.28 V and about 0.32 V, etc. In embodiments, the bias voltage is lower than 0.30, 0.31 or 0.32 V.

Bias Voltage in Enzymatic Sensing Electrode

For the sake of contrast, enzymatic glucose sensors apply the bias voltage in the range of 0.5-0.6 V. In the enzymatic sensing sensors, this bias voltage does not cause oxidation of glucose at its sensing electrode or elsewhere. Rather, glucose-specific enzymes oxidize glucose molecules, which generates electron to an electron mediator that is oxidized at the conductive layer by the bias voltage. Thus, the bias voltage is to cause oxidation of the electron mediator in the enzymatic electrode.

EXAMPLES

Now various aspects and features of the invention are further discussed in connection with examples and experiments.

Preparing Reverse Micelle Phase

Example 1.1

A platinum aqueous solution was prepared by dissolving 0.500 g (0.965 mmol) of chloroplatinic acid hexahydrate H$_2$PtCl$_6$.6H$_2$O (from Sigma-Aldrich) in 24.5 g of purified water with stirring. 25 g of surfactant, Triton X-100™ (from Sigma-Aldrich) was added to the platinum aqueous solution to provide an aqueous composition containing surfactant and platinum ions. The concentration of the platinum ions in the aqueous composition was about 0.02 M. A reverse micelles phase was prepared in the aqueous composition by adjusting the temperature to 70° with stirring.

Example 1.2

A reverse micelle phase is prepared by repeating Example 1.1 except that PtCl$_4$.6H$_2$O is used, in replacement of H$_2$PtCl$_6$.6H$_2$O, in an amount to provide the platinum ion concentration about 0.02 M in the aqueous composition.

Example 1.3

A reverse micelle phase is prepared by repeating Example 1.1 except that H$_2$PtCl$_2$(OH)$_4$ is used, in replacement of H$_2$PtCl$_6$.6H$_2$O, in an amount to provide the platinum ion concentration about 0.02 M in the aqueous composition.

Example 1.4

A reverse micelle phase is prepared by repeating Example 1.1 except that H$_2$Pt(SO$_4$)(OH)$_4$.6H$_2$O is used, in replacement of H$_2$PtCl$_6$.6H$_2$O, in an amount to provide the platinum ion concentration about 0.02 M in the aqueous composition.

Example 1.5

A reverse micelle phase is prepared by repeating Example 1.1 except that TiCl$_4$.6H$_2$O is used, in replacement of H$_2$PtCl$_6$.6H$_2$O, in an amount to provide the titanium ion concentration about 0.02 M in the aqueous composition.

Example 1.6

A reverse micelle phase is prepared by repeating Example 1.1 except that NP-40™ is used as surfactant, in replacement of Triton X-100, to provide the platinum ion concentration about 0.02 M in the aqueous composition and further except that the amount of surfactant and the temperature are adjusted to achieve a reverse micelle phase of the surfactant.

Example 1.7

A reverse micelle phase is prepared by repeating Example 1.1 except that polysorbate 80 is used as surfactant, in replacement of Triton X-100, to provide the platinum ion concentration about 0.02 M in the aqueous composition and further except that the amount of surfactant and the temperature are adjusted to achieve a reverse micelle phase of the particular surfactant.

Example 1.8

A reverse micelle phase is prepared by repeating Example 1.1 except that isoceteth-20 is used as surfactant, in replacement of Triton X-100, to provide the platinum ion concentration about 0.02 M in the aqueous composition and further except that the amount of surfactant and the temperature are adjusted to achieve a reverse micelle phase of the particular surfactant.

58

Example 1.9

A reverse micelle phase is prepared by repeating Example 1.1 except that poloxamer 407 is used as surfactant, in replacement of Triton X-100, to provide the platinum ion concentration about 0.02 M in the aqueous composition and further except that the amount of surfactant and the temperature are adjusted to achieve a reverse micelle phase of the particular surfactant.

Example 1.10

A reverse micelle phase is prepared by repeating Example 1.1 except that monolaurin is used as surfactant, in replacement of Triton X-100, to provide the platinum ion concentration about 0.02 M in the aqueous composition and further except that the amount of surfactant and the temperature are adjusted to achieve a reverse micelle phase of the particular surfactant.

Preparing Reducing Agent

Example 2.1

A reducing agent aqueous solution was prepared by adding 30 g (0.170 mol) of ascorbic acid as a reducing agent to 250 ml of purified water with stirring. The reducing agent solution was heated to 70° C. The concentration of the ascorbic acid in the reducing agent aqueous solution was 0.6 M, which is equivalent to 60 times the concentration of metal ions of Examples 1.1 through 1.10.

Example 2.2

A reducing agent aqueous solution was prepared by repeating Example 2.1 except that form aldehyde is used as reducing agent in replacement of ascorbic acid. The amount of form aldehyde is adjusted to provide its concentration in the reducing agent aqueous solution about 0.6 M.

Example 2.3

A reducing agent aqueous solution was prepared by repeating Example 2.1 except that acetic acid is used as reducing agent in replacement of ascorbic acid. The amount of acetic acid is adjusted to provide its concentration in the reducing agent aqueous solution about 0.6 M.

Example 2.4

A reducing agent aqueous solution was prepared by repeating Example 2.1 except that hypophosphite is used as reducing agent in replacement of ascorbic acid. The amount of hypophosphite is adjusted to provide its concentration in the reducing agent aqueous solution about 0.6 M.

Forming Nanoparticle Colloid

Example 3.1

The reducing agent aqueous solution prepared in Example 2.1 was added to the aqueous composition of Example 1.1 at 70° C. soon after the reverse micelle phase was prepared. In the resulting liquid composition, the concentration of platinum ions was about 0.0028 M, and the concentration of ascorbic acid was about 0.50 M. The resulting liquid composition was continuously stirred for about 4 hours at 70° C. A black platinum colloid was obtained.

Examples 3.2-3.10

Example 3.1 is repeated using the reverse micelle phases prepared in Examples 1.2-1.10, in replacement of the reverse micelle phase prepared in Example 1.1, which provides metal colloids of Examples 3.2-3.10, respectively.

Particle Size Analysis of Nanoparticle Colloid

Example 4.1

Korea Polymer Testing and Research Institute (KOPTRI) performed a dynamic light-scattering particle size analysis for the platinum colloid obtained from Example 3.1 using Zeta-potential & particle size analyzer ELS-Z2 of Photal Otsuka Electronics. For the analysis, a sample of the Example 3.1 platinum colloid was dispersed in purified water having refractive index of 1.3328, viscosity of 0.8878 cp, and dielectric constant of 78.3 at 25° C.

Figure 14:
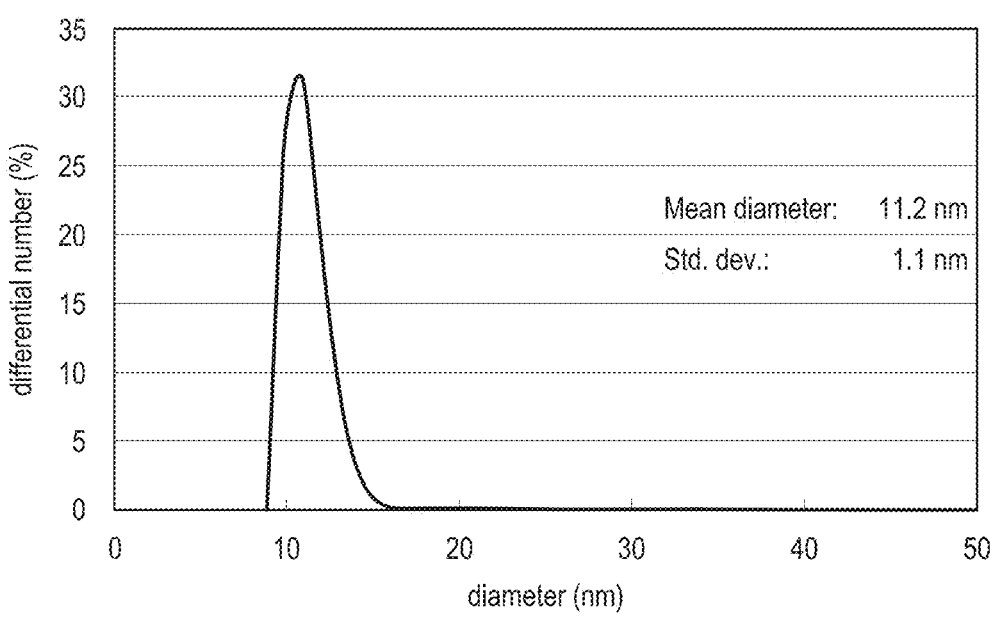
FIG. 14 shows a particle size distribution for nanoparticle-surfactant colloid prepared according to an embodiment.

FIG. 14 shows particle size distribution for the colloid obtained from Example 3.1. The particle diameters are primarily between about 9 nm and about 14 nm. This size distribution is interpreted as representing the reverse micelles. The size distribution does not show diameter sizes of 1-5 nm, which is interpreted as most platinum nanoparticles being contained or encompassed inside the reverse micelles. Similar results were obtained from multiple runs of the experiments according to Examples 1.1, 2.1 and 3.1.

Examples 4.2-4.10

The analysis of Example 4.1 is repeated using each colloid prepared in Examples 3.2-3.10, in replacement of the colloid prepared in Example 3.1. A particle size distribution for each of the colloid prepared in Examples 3.2-3.10 is obtained.

Removing Surfactant

Example 5.1

50 ml of 0.3 M HCl aqueous solution was added to 60 ml of the platinum colloid prepared in Example 3.1. The acid-added platinum colloid was centrifuged for 10 minutes at 3800 rpm. Subsequently, clear supernatant was discarded, and black bottom portion was collected. The sequence of adding HCl aqueous solution, centrifugation and collecting black bottom portion was repeated four additional times to remove the surfactant and obtain a platinum colloid.

Subsequently, the resulting platinum colloid was washed with purified water to remove HCl. 50 ml of purified water was added to the collected platinum colloid. The water-added platinum colloid was centrifuged for 10 minutes at 3800 rpm. Then, clear supernatant was discarded, and black bottom portion was collected. The sequence of adding purified water, centrifugation and collecting black bottom portion was repeated four additional times to remove HCl and obtain an HCl-washed platinum colloid.

Examples 5.2-5.10

Example 5.1 is repeated using the nanoparticle colloid obtained from Examples 3.2-3.10, in replacement of the nanoparticle colloid prepared in Example 3.1 to collect colloids of Examples 5.2-5.10 respectively.

Example 5.11

Example 5.1 is repeated using 0.3 M $HNO_3$ aqueous solution in replacement of HCl aqueous solution.

Example 5.12

Example 5.1 is repeated using 0.3 M NaOH aqueous solution in replacement of HCl aqueous solution.

Particle Size Analysis of Cluster Colloid

Example 6.1

Korea Polymer Testing and Research Institute (KOPTRI) performed a dynamic light-scattering particle size analysis for the platinum colloid obtained from Example 5.1 using Zeta-potential & particle size analyzer ELS-Z2 of Photal Otsuka Electronics as in Example 4.1. For the analysis, a sample of the Example 5.1 colloid was dispersed in water having refractive index of 1.3328, viscosity of 0.8878 cp, and dielectric constant of 78.3 at 25° C.

Figure 15:
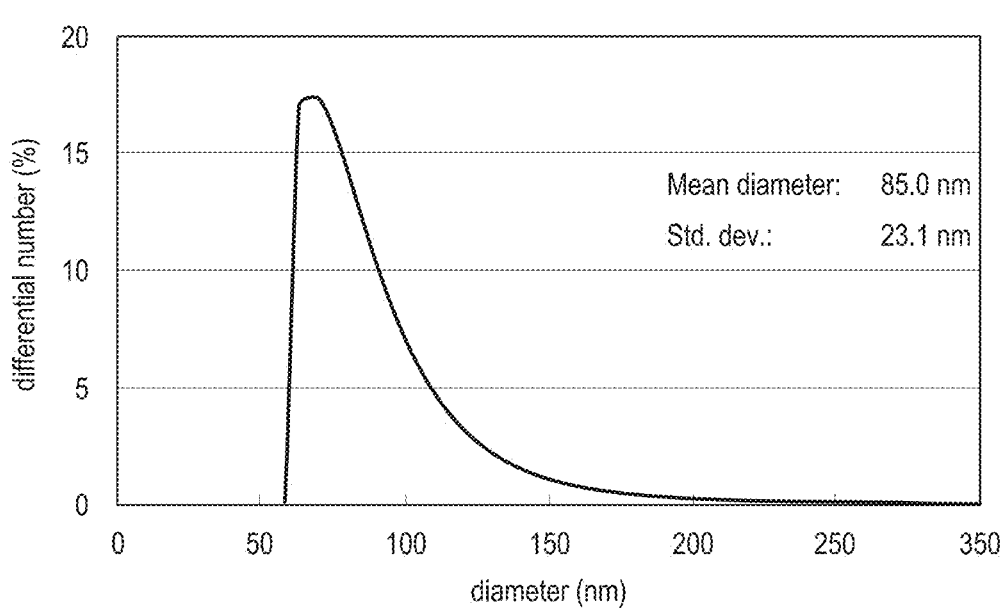
FIG. 15 shows a particle size distribution for cluster colloid prepared according to an embodiment.

FIG. 15 shows particle size distribution for the colloid obtained from Example 5.1. The particle diameters are primarily between about 60 nm and about 200 nm. This size distribution is interpreted as representing irregularly shaped clusters formed of nanoparticles. Considering that the particle size in Example 4.1 is primarily between about 9 nm and about 14 nm (the size of a reverse micelle and not of clusters), it is understood that clusters were formed by the processes of Example 5.1, in which surfactant molecules were detached from platinum nanoparticles by addition of acidic solution and the surfactant was removed by centrifugation and collection of bottom portion. Similar results were obtained from multiple runs of the experiments according to Examples 1.1, 2.1, 3.1 and 5.1.

Examples 6.2-6.10

Example 6.1 is repeated using each colloid prepared in Examples 3.2-3.10, in replacement of the colloid prepared in Example 3.1. A particle size distribution for each colloid prepared in Examples 3.2-3.10 is obtained.

Recovery of Platinum—Yield

Example 7

The cluster colloid obtained in Example 5.1 was subjected to drying. The dry weight of the colloid was 0.143 g. The resulting colloid in Example 5.1 was prepared from 60 ml of the nanoparticle colloid prepared in Example 3.1, which contained 0.188 g. In the overall process, the yield of platinum was 76.1%.

Making Electrode with Clustered Nanoporous Layer

Example 8.1—Electrode Base

Figure 16A:
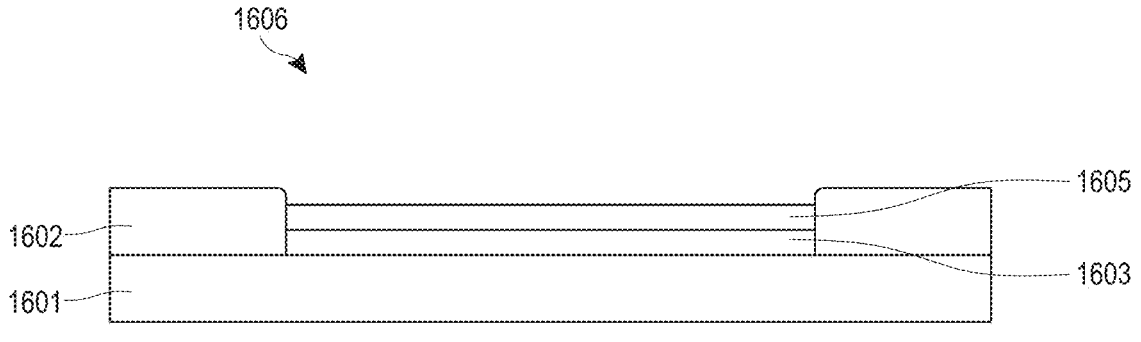
FIGS. 16A and 16B illustrate a cross-section of an electrode base and a non-enzymatic glucose-sensing working electrode, respectively, according to embodiments.

A silver layer 1603 and a conductive carbon layer 1605 were formed on a substrate 1601 made of polyimide as illustrated in FIG. 16A. The silver layer 1603 was formed in a thickness of about 20 μm by printing a silver ink containing silver particles. The conductive carbon layer 1605 was formed in a thickness of about 20 μm by printing a carbon ink containing carbon particles. A polyimide insulation film 1602 was laminated over the substrate 1601 around the silver layer 1603 and conductive carbon layer 1605 to provide the electrode base 1606.

Example 8.2—Forming Nanoporous Layer

Figure 16B:
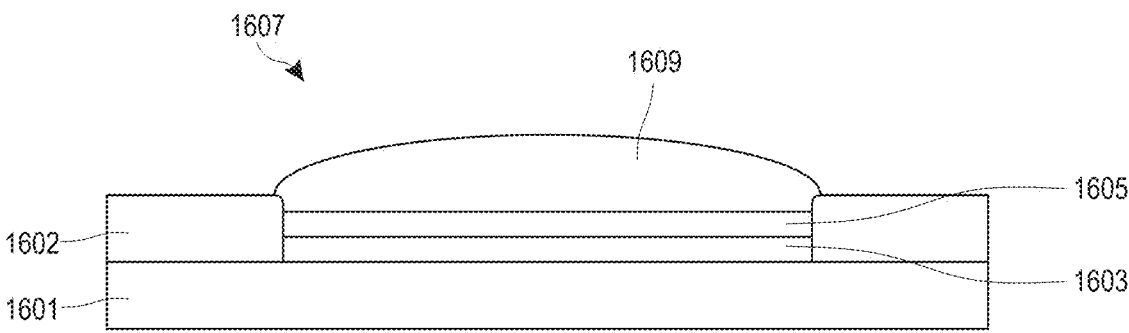

The cluster colloid obtained in Example 5.1 was diluted to the concentration of 60 mg/ml. Using a micro-syringe, 0.2 μL of the diluted cluster colloid was dropped on the conductive carbon layer of the electrode base 1606. The electrode base with the colloid dropped thereon was placed in an oven at 60° C. for 30 minutes to form an electrode 1607 including a platinum nanoporous layer 1609 as illustrated in FIG. 16B.

Example 8.3—Roughness Factor

The electrochemical cell of FIG. 1 was prepared using electrochemical analyzer CHI660 from CH Instruments Inc. as potentiostat 104 and using the electrode 1607 prepared in Example 8.2 as working electrode 103, a platinum wire as counter electrode 105, and Ag/AgCl (3 M KCl) as reference electrode 106. The silver layer 1603 of the electrode 1607 was connected to the potentiostat 104. Instead of the test fluid 102, 1M $H_2SO_4$ aqueous solution was added to the electrochemical cell of FIG. 1.

Cyclic voltammetry was performed with potential sweeping between −0.2 V and +1.2 V. The real surface area of the platinum nanoporous layer was obtained by measuring the amount of proton adsorbed to the surfaces of platinum nanoporous layer using the cyclic voltammetry. The top surface area (geometric area) of the platinum nanoporous layer was measured. Roughness factor was calculated by dividing the real surface area by the geometric area. The roughness factor of the nanoporous layer obtained from Example 8.2 was 1147.

Example 8.4—Repeating Examples 8.1-8.2

Examples 8.1 was repeated multiple times to prepare additional electrode bases. Example 8.2 was repeated multiple times using the additional electrode bases to prepare additional electrodes 1607 including a platinum nanoporous layer 1609.

Example 8.5—Repeating Example 8.3

Example 8.3 was repeated for the five electrodes 1607 prepared in Example 8.4. The roughness factor values of the nanoporous layers were 1187, 1171, 1143, 1190 and 1119.

Example 8.6—SEM Photographs

Figure 17A:
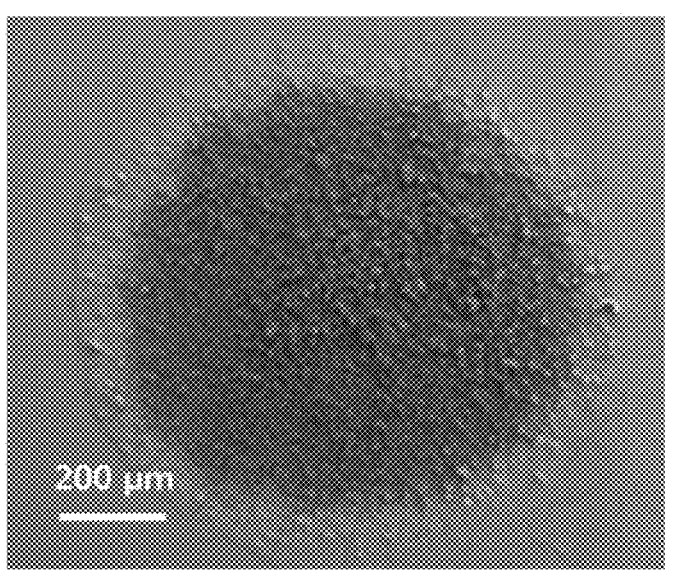
Figure 17B:
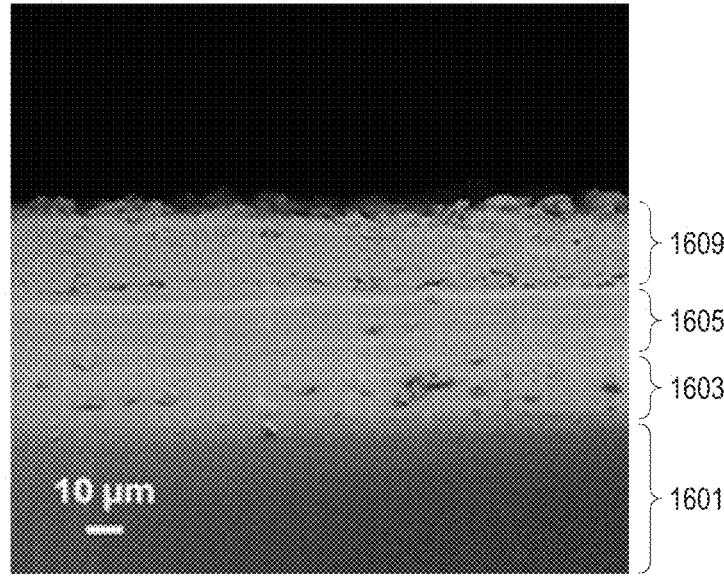

FIG. 17A is an SEM photograph taken from the top of an electrode 1607 obtained from Example 8.4. The darker center represents the area of the conductive carbon layer. FIG. 17B is an SEM photograph of a cross-section of the electrode 1607 showing the platinum nanoporous layer 1609, carbon conductive layer 1605 and silver layer 1603 in sequence from the top. FIG. 17C includes three SEM photographs of another electrode 1607 prepared in Example 8.4. These three photographs are taken from the top in different magnifications.

Sensing Glucose in PBS

Example 9.1—Preparing Solutions of Glucose and Other Test Materials

D-(+)-glucose powder purchased from Sigma-Aldrich was dissolved in purified water to prepare 1 M glucose stock solution. Ascorbic acid purchased from Sigma-Aldrich was dissolved in purified water to prepare 0.05 M ascorbic Sigma-Aldrich acid aqueous solution. Acetaminophen purchased from Sigma-Aldrich was dissolved in purified water to prepare 0.05 M acetaminophen aqueous solution. Maltose purchased from Sigma-Aldrich was dissolved in purified water to prepare 0.5 M maltose aqueous solution.

Example 9.2—Preparing PBS 500 ml aqueous solution containing 0.1 M $NaH_2PO_4$ and 0.15 M NaCl in purified water was prepared. 500 ml aqueous solution containing 0.1 M $Na_2HPO_4$ and 0.15 M NaCl in purified water was prepared. The two aqueous solutions were mixed to prepare 1 L stock phosphate buffered saline (PBS) in pH 7.4.

Example 9.3—Preparing Glucose-Sensing System in PBS 20 ml of the PBS prepared in Example 9.2 was placed in a beaker, in which the temperature of PBS was maintained at 37° C. The electrochemical cell of FIG. 1 was prepared using electrochemical analyzer CHI660 from CH Instruments Inc. as potentiostat 104 and using the electrode 1607 prepared in Example 8.4 as working electrode 103, a platinum wire as counter electrode 105, and Ag/AgCl (3 M KCl) as reference electrode 106. The silver layer 1603 of the electrode 1607 was connected to the potentiostat 104. The electrodes were submerged into PBS and electrically connected to the electrochemical analyzer.

Example 9.4—Measuring Electric Current

Figure 18:
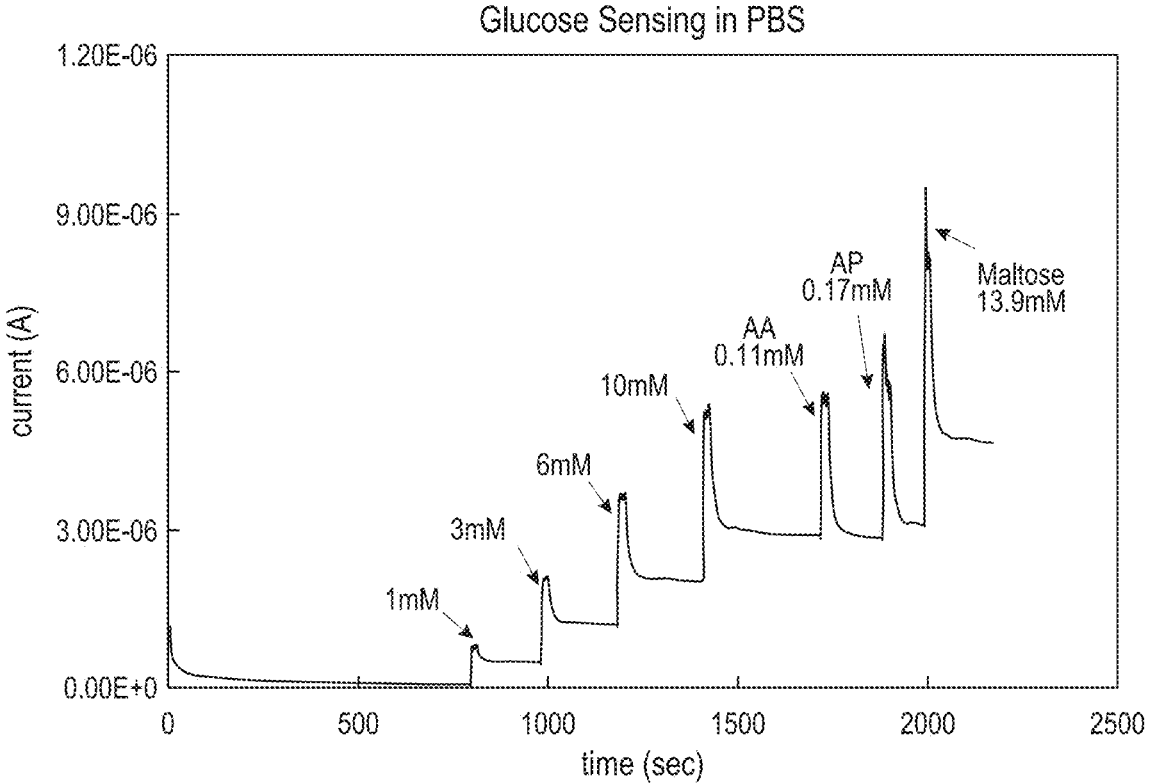
FIG. 18 is a profile of electric current generated by oxidation of glucose and other materials in PBS according to embodiments.

In the system prepared in Example 9.3, the bias voltage of 0.4 V was applied between the working electrode 103 (electrode 1607) and the reference electrode 106. Upon application of the bias voltage, electric current from the working electrode 103 was continuously measured. The electrochemical cell was kept for 12 minutes for conditioning the glucose-sensing system in PBS without addition of any substance thereto. Subsequently, the current value of 0.087 μA was taken for no glucose contained in the PBS. FIG. 18 shows the electric current profile obtained from the electrochemical cell for Examples 9.5-9.11 below. In FIG. 18, "AA" represents ascorbic acid, and "AP" represents acetaminophen.

Example 9.5—Sensing 1 mM Glucose in PBS

After conditioning of the glucose-sensing system, 20 μl of the glucose stock solution prepared in Example 9.1 was added to the PBS of Example 9.3 to make 1 mM glucose in the PBS. Immediately after the addition, the glucose-added PBS was stirred for 3-4 seconds, which caused temporary peaks of electric current. The electric current from the working electrode was continuously measured. When the current became stable, the current value of 0.54 μA was taken for 1 mM glucose in PBS.

Example 9.6—Sensing 3 mM Glucose in PBS

After the current became stable in Example 9.5, 40 μl of the glucose stock solution prepared in Example 9.1 was added to the PBS resulting from Example 9.4 to make the total glucose 3 mM in the PBS. Immediately after the addition, the glucose-added PBS was stirred for 3-4, seconds, which caused temporary peaks of electric current. The electric current from the working electrode was continuously measured. When the current became stable, the current value of 1.19 μA was taken for 3 mM glucose in PBS.

Example 9.7—Sensing 6 mM Glucose in PBS

After the current became stable in Example 9.6, 60 μl of the glucose stock solution prepared in Example 9.1 was added to the PBS resulting from Example 9.5 to make the total glucose 6 mM in the PBS. Immediately after the addition, the glucose-added PBS was stirred for 3-4, seconds, which caused temporary peaks of electric current. The electric current from the working electrode was continuously measured. When the current became stable, the current value of 2.09 μA was taken for 6 mM glucose in PBS.

Example 9.8—Sensing 10 mM Glucose in PBS

After the current became stable in Example 9.7, 80 μl of the glucose stock solution prepared in Example 9.1 was added to the PBS resulting from Example 9.6 to make the total glucose 10 mM in the PBS. Immediately after the addition, the glucose-added PBS was stirred for 3-4, seconds, which caused temporary peaks of electric current. The electric current from the working electrode was continuously measured. When the current became stable, the current value of 2.89 μA was taken for 10 mM glucose in PBS.

Example 9.9—Sensing 0.11 mM Ascorbic Acid in PBS

After the current became stable in Example 9.8, 44 μl of the ascorbic acid aqueous solution prepared in Example 9.1 was added to the PBS resulting from Example 9.7 to make 0.11 mM ascorbic acid (AA) in the PBS. Immediately after the addition, the ascorbic acid-added PBS was stirred for 3-4, seconds, which caused temporary peaks of electric current. The electric current from the working electrode was continuously measured. When the current became stable, the current value of 2.93 μA was taken for the sum of 10 mM glucose and 0.11 mM ascorbic acid in PBS.

Example 9.10—Sensing 0.17 mM Acetaminophen in PBS

After the current became stable in Example 9.9, 68 μl of the acetaminophen aqueous solution prepared in Example 9.1 was added to the PBS resulting from Example 9.8 to make 0.17 mM acetaminophen (AP) in the PBS. Immediately after the addition, the acetaminophen-added PBS was stirred for 3-4, seconds, which caused temporary peaks of electric current. The electric current from the working electrode was continuously measured. When the current became stable, the current value of 3.21 μA was taken for the sum of 10 mM glucose, 0.11 mM ascorbic acid and 0.17 mM acetaminophen in PBS.

Example 9.11—Sensing 13.9 mM Maltose in PBS

After the current became stable in Example 9.10, 556 μl of the maltose aqueous solution prepared in Example 9.1 was added to the PBS resulting from Example 9.9 to make 13.9 mM maltose in the PBS. Immediately after the addition, the maltose-added PBS was stirred for 3-4, seconds, which caused temporary peaks of electric current. The electric current from the working electrode was continuously measured. When the current became stable, the current value of 4.74 μA was taken for the sum of 10 mM glucose, 0.11 mM ascorbic acid, 0.17 mM acetaminophen and 13.9 mM maltose in PBS.

Example 9.12—Glucose Level Formula

In Examples 9.5-9.11, the current values represent and correspond to the concentrations of glucose in the PBS. Similar experiments are conducted many more times for the glucose-sensing system prepared in the same manner using the same and other glucose concentrations to obtain data of current values and corresponding glucose concentrations. A correlation between glucose concentration and current value in the PBS is obtained by processing the data. Glucose concentrations are computed using the correlation and the current values obtained from Examples 9.5-9.11.

Sensing Glucose in Serum

Example 10.1—Preparing Glucose-Sensing System in Serum

Human serum was purchased from Sigma-Aldrich. The glucose content in the serum was measured using YSI. It was determined that the serum contained 5.8 mM glucose therein, which corresponds to blood glucose level 104 mg/dl. 10 ml of the serum was placed in a beaker, in which the temperature of the serum was maintained at 37° C. An electrochemical cell was prepared as in Example 9.3 except that one electrode 1607 prepared in Example 8.4 was used as working electrode 103 and further except that the working, reference and counter electrodes were submerged into the serum.

Example 10.2—Pre-Conditioning Glucose-Sensing System in Serum 0.4 V bias voltage was applied between the working electrode 103 and the reference electrode 106 of the electrochemical cell prepared in Example 10.1. The bias voltage was maintained for over 3 hours in the electrochemical system for conditioning the system, i.e., waiting for the background current to become low enough for sensing glucose oxidation. Subsequently, the bias voltage was disconnected from the system.

Example 10.3—Measuring Electric Current

Figure 19:
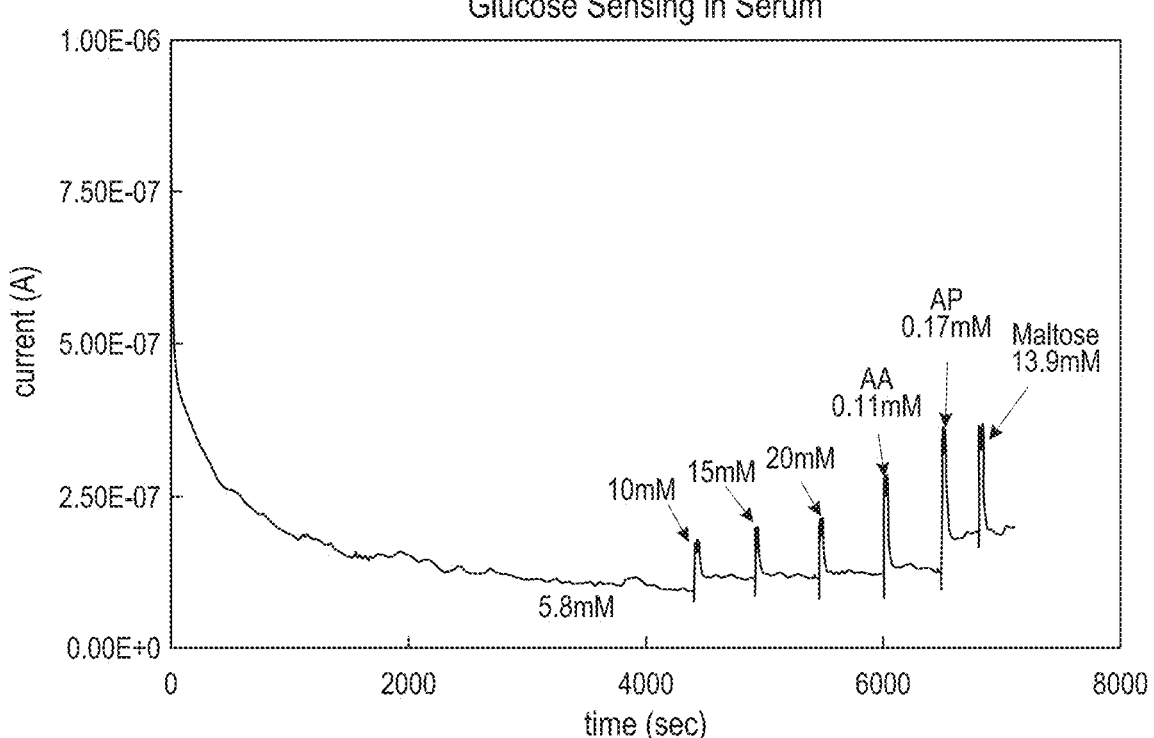
FIG. 19 is a profile of electric current generated by oxidation of glucose and other materials in human serum according to embodiments.

Soon after removing the bias voltage in Example 10.2, the same bias voltage was reapplied to the system, and measuring of electric current from the working electrode began. The electrochemical cell was kept for 1.2 hours for further conditioning the glucose-sensing system in the serum without adding any substance thereto. When the current became stable, the current value of 96 nA was taken for 5.8 mM glucose originally contained in serum. FIG. 19 shows a profile of the electric current measured from the electrochemical cell of Examples 10.4-10.9 below. In FIG. 19, "AA" represents ascorbic acid, and "AP" represents acetaminophen.

Example 10.4—Sensing 10 mM Glucose in Serum

After conditioning of the glucose-sensing system, 42 μl of the glucose stock solution prepared in Example 9.1 was added to the serum of Example 10.2 to make the total glucose 10 mM in the serum. Immediately after the addition, the glucose-added serum was stirred for 3-4, seconds, which caused temporary peaks of electric current. The electric current from the working electrode was continuously measured. When the current became stable, the current value of 110 nA was taken for 10 mM glucose in serum.

Example 10.5—Sensing 15 mM Glucose in Serum

After the current became stable in Example 10.4, 50 μl of the glucose stock solution prepared in Example 9.1 was added to the serum of Example 10.3 to make the total glucose 15 mM in the serum. Immediately after the addition, the glucose-added serum was stirred for 3-4, seconds, which caused temporary peaks of electric current. The electric current from the working electrode was continuously measured. When the current became stable, the current value of 132 nA was taken for 15 mM glucose in serum.

Example 10.6—Sensing 20 mM Glucose in Serum

After the current became stable in Example 10.5, 50 μl of the glucose stock solution prepared in Example 9.1 was added to the serum of Example 10.4 to make the total glucose 20 mM in the serum. Immediately after the addition, the glucose-added serum was stirred for 3-4, seconds, which caused temporary peaks of electric current. The electric current from the working electrode was continuously measured. When the current became stable, the current value of 159 nA was taken for 20 mM glucose in serum.

Example 10.7—Sensing 0.11 mM Ascorbic Acid in Serum

After the current became stable in Example 10.6, 22 μl of the ascorbic acid aqueous solution prepared in Example 9.1 was added to the serum resulting from Example 10.5 to make 0.11 mM ascorbic acid (AA) in the serum. Immediately after the addition, the ascorbic acid-added serum was stirred for 3-4, seconds, which caused temporary peaks of electric current. The electric current from the working electrode was continuously measured. When the current became stable, the current value of 163 nA was taken for the sum of 20 mM glucose and 0.11 mM ascorbic acid in serum.

Example 10.8—Sensing 0.17 mM Acetaminophen in Serum

After the current became stable in Example 10.7, 34 μl of the acetaminophen aqueous solution prepared in Example 9.1 was added to the serum resulting from Example 10.6 to make 0.17 mM acetaminophen (AP) in the serum. Immediately after the addition, the acetaminophen-added serum was stirred for 3-4, seconds, which caused temporary peaks of electric current. The electric current from the working electrode was continuously measured. When the current became stable, the current value of 223 nA was taken for the sum of 20 mM glucose, 0.11 mM ascorbic acid and 0.17 mM acetaminophen in serum.

Example 10.9—Sensing 13.9 mM Maltose in Serum

After the current became stable in Example 10.8, 278 μl of the maltose aqueous solution prepared in Example 9.1 was added to the serum resulting from Example 10.7 to make 13.9 mM maltose in the serum. Immediately after the addition, the maltose-added serum was stirred for 3-4, seconds, which caused temporary peaks of electric current. The electric current from the working electrode was continuously measured. When the current became stable, the current value of 231 nA was taken for the sum of 20 mM glucose, 0.11 mM ascorbic acid, 0.17 mM acetaminophen and 13.9 mM maltose in serum.

Example 10.10—Glucose Level Formula

In Examples 10.4-10.9, the current values represent and correspond to the concentrations of glucose in the serum. Similar experiments are conducted many more times for the glucose-sensing system prepared in the same manner using the same and other glucose concentrations to obtain data of current values and corresponding glucose concentrations. A correlation between glucose concentration and current value in the serum is obtained by processing the data. Glucose concentrations are computed using the correlation and the current values obtained from Examples 10.4-10.9.

Non-Clustered Nanoporous Layers

Example 11.1—Electroplating from Reverse Micelle Phase

This disclosure hereby incorporates herein the examples and discussions of the U.S. Pat. No. 8,343,690 ('690 patent) in its entirety. The experiments appearing at columns 6 through 9 of the '690 patent are specifically incorporated herein as examples for making nanoporous layer by electroplating and using the layer for glucose sensing.

Example 11.2—Electroplating from Hexagonal Phase

This disclosure hereby incorporates herein the disclosure of U.S. Pat. No. 7,892,415 ('415 patent) in its entirety. The experiments appearing at columns 5 through 6 of the '415 patent are specifically incorporated herein as examples for making hexagonal structured nanoporous layer by electroplating and using the layer for glucose sensing.

Example 11.3—Electroplating from Hexagonal Phase

This disclosure hereby incorporates herein the disclosure of "Electrochemistry Communications, Vol. 4, Issue 8, August 2002, pages 610-612" in its entirety.

Example 11.4—Chemical Deposition from Hexagonal Phase

This disclosure hereby incorporates herein the disclosure of "Science, Vol. 278, Oct. 31, 1997, pages 838-840" in its entirety.

Making Maltose-Blocking Layer

Example 12.1—Preparing Aqueous mPD Solutions

M-phenylenediamine (mPD) purchased from Sigma-Aldrich was dissolved in purified water to provide aqueous mPD solutions containing mPD in 0.1, 0.3, 0.5, 1.0, 2.0 and 5.0 mM.

Example 12.2—Preparing for Cyclic Voltammetry

An electrochemical cell was prepared using electrochemical analyzer CHI Multi 1030C from CH Instruments Inc. as potentiostat 104 and using the electrode 1607 prepared in Example 8.4 as working electrode 103, a platinum wire as counter electrode 105, and Ag/AgCl (3 M KCl) as reference electrode 106. The counter electrode 105 and reference electrode 106 were electrically connected to form a two-electrode system.

Example 12.3—Electrochemical Polymerization at 0.1 mM, 10 mV/sec

In the electrochemical cell prepared in Example 12.2, the 0.1 mM aqueous mPD solution prepared in Example 12.1 was added instead of the test fluid 102. Cyclic voltammetry was performed with potential sweeping between +0.5 V and +1.0 V at the scanning rate of 10 mV/sec for two sweeping segments as illustrated in FIG. 22, which resulted in a poly-mPD maltose-blocking layer 301 on the nanoporous layer 117.

Example 12.4—Electrochemical Polymerization at 0.1 mM, 100 mV/sec

Example 12.3 was repeated except that the scanning rate was 100 mV/sec, which formed a poly-mPD layer on the nanoporous layer 117.

Example 12.5—Electrochemical Polymerization at 0.1 mM, 200 mV/sec

Example 12.3 was repeated except that the scanning rate was 200 mV/sec, which formed a poly-mPD layer on the nanoporous layer 117.

Example 12.6—Electrochemical Polymerization at 0.3 mM, 10 mV/sec

Example 12.3 was repeated except that the 0.3 mM aqueous mPD solution prepared in Example 12.1 was added instead of the 0.1 mM aqueous mPD solution, which formed a poly-mPD layer on the nanoporous layer 117.

Example 12.7—Electrochemical Polymerization at 0.3 mM, 100 mV/sec

Example 12.6 was repeated except that the scanning rate was 100 mV/sec, which formed a poly-mPD layer on the nanoporous layer 117.

Example 12.8—Electrochemical Polymerization at 0.3 mM, 200 mV/sec

Example 12.6 was repeated except that the scanning rate was 200 mV/sec, which formed a poly-mPD layer on the nanoporous layer 117.

Example 12.9—Electrochemical Polymerization at 0.5 mM, 10 mV/sec

Example 12.3 was repeated except that the 0.5 mM aqueous mPD solution prepared in Example 12.1 was added instead of the 0.1 mM aqueous mPD solution, which formed a poly-mPD layer on the nanoporous layer 117.

Example 12.10—Electrochemical Polymerization at 0.5 mM, 100 mV/sec

Example 12.6 was repeated except that the scanning rate was 100 mV/sec, which formed a poly-mPD layer on the nanoporous layer 117.

Example 12.11—Electrochemical Polymerization at 0.5 mM, 200 mV/sec

Example 12.6 was repeated except that the scanning rate was 200 mV/sec, which formed a poly-mPD layer on the nanoporous layer 117.

Example 12.12—Electrochemical Polymerization at 1.0 mM, 10 mV/sec

Example 12.3 was repeated except that the 1.0 mM aqueous mPD solution prepared in Example 12.1 was added instead of the 0.1 mM aqueous mPD solution, which formed a poly-mPD layer on the nanoporous layer 117.

Example 12.13—Electric Shock

Figure 23:
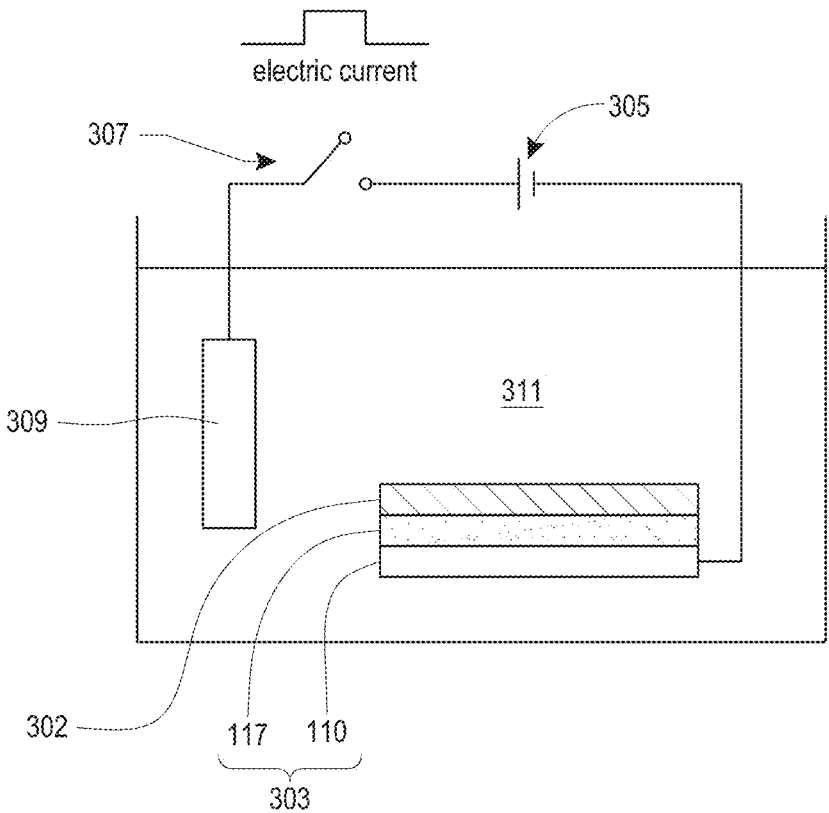
FIG. 23 illustrates a chronoamperometry setup for an electric shock treatment to adjust porosity of a porous polymer layer according to an embodiment.

The electrochemical cell of FIG. 23 was prepared for chronoamperometry using the poly-mPD layer prepared in Example 12.12 as the porous polymer layer 302 and 1 M $H_2SO_4$ aqueous solution as the electrolyte solution. Electric shock was applied to the porous polymer layer 302 by applying a single pulse from +0.0 V to +1.0 with the pulse width of 1.0 sec.

Example 12.14—Electrochemical Polymerization at 1.0 mM, 100 mV/sec and Electric Shock Example 12.6 was repeated except that the scanning rate was 100 mV/sec, which formed a poly-mPD layer on the nanoporous layer 117. Subsequently, Example 12.13 was repeated using the poly-mPD layer formed on the nanoporous layer.

Example 12.15—Electrochemical Polymerization at 1.0 mM, 200 mV/sec and Electric Shock Example 12.6 was repeated except that the scanning rate was 200 mV/sec, which formed a poly-mPD layer on the nanoporous layer 117. Subsequently, Example 12.13 was repeated using the poly-mPD layer formed on the nanoporous layer.

Example 12.16—Electrochemical Polymerization at 2.0 mM, 10 mV/sec and Electric Shock Example 12.3 was repeated except that the 2.0 mM aqueous mPD solution prepared in Example 12.1 was added instead of the 0.1 mM aqueous mPD solution, which formed a poly-mPD layer on the nanoporous layer 117. Subsequently, Example 12.13 was repeated using the poly-mPD layer formed on the nanoporous layer.

Example 12.17—Electrochemical Polymerization at 2.0 mM, 100 mV/sec and Electric Shock Example 12.6 was repeated except that the scanning rate was 100 mV/sec, which formed a poly-mPD layer on the nanoporous layer 117. Subsequently, Example 12.13 was repeated using the poly-mPD layer formed on the nanoporous layer.

Example 12.18—Electrochemical Polymerization at 2.0 mM, 200 mV/sec and Electric Shock Example 12.6 was repeated except that the scanning rate was 200 mV/sec, which formed a poly-mPD layer on the nanoporous layer 117. Subsequently, Example 12.13 was repeated using the poly-mPD layer formed on the nanoporous layer.

Example 12.19—Electrochemical Polymerization at 5.0 mM, 10 mV/sec and Electric Shock Example 12.3 was repeated except that the 5.0 mM aqueous mPD solution prepared in Example 12.1 was added instead of the 0.1 mM aqueous mPD solution, which formed a poly-mPD layer on the nanoporous layer 117. Subsequently, Example 12.13 was repeated using the poly-mPD layer formed on the nanoporous layer.

Example 12.20—Electrochemical Polymerization at 5.0 mM, 100 mV/sec and Electric Shock Example 12.6 was repeated except that the scanning rate was 100 mV/sec, which formed a poly-mPD layer on the nanoporous layer 117. Subsequently, Example 12.13 was repeated using the poly-mPD layer formed on the nanoporous layer.

Example 12.21—Electrochemical Polymerization at 5.0 mM, 200 mV/sec and Electric Shock Example 12.6 was repeated except that the scanning rate was 200 mV/sec, which formed a poly-mPD layer on the nanoporous layer 117. Subsequently, Example 12.13 was repeated using the poly-mPD layer formed on the nanoporous layer.

Sensing Glucose without Interference by Maltose

Example 13.1—Preparing Serum

Human serum was purchased from Sigma-Aldrich. The glucose content in the serum was measured using YSI. It was determined that the serum contained 5.8 mM glucose therein, which corresponds to blood glucose level 104 mg/dl.

Example 13.2—Preparing Glucose-Sensing System in Serum 10 ml of the serum prepared in Example 13.1 was placed in a beaker, in which the temperature of the serum was maintained at 37° C. An electrochemical cell was prepared as in Example 10.2 except that the working electrode 103 includes a poly-mPD maltose-blocking layer 301 on nanoporous layer as prepared in Example 12.3 using 0.1 mM mPD solution and scanning rate of 10 mV/sec.

Example 13.1—Preparing Glucose-Sensing System in Serum

An electrochemical cell was prepared by repeating Example 10.2 except that the working electrode 103 includes a poly-mPD maltose-blocking layer 301 on nanoporous layer as prepared in Example 12.3 (using 0.1 mM mPD solution and scanning rate of 10 mV/sec) and further except that the working, reference and counter electrodes were submerged into the serum.

Example 13.2—Conditioning Glucose-Sensing System in Serum

In the electrochemical cell system prepared in Example 13.1, bias voltage 0.4 V was applied between the working electrode 103 and the reference electrode 106. The bias voltage was maintained for over 3 hours in the electrochemical system for pre-conditioning the system. Subsequently, the bias voltage was disconnected from the system and reconnected. Upon re-application of the bias voltage, measuring of electric current from the working electrode began. The electrochemical cell was kept for further conditioning the glucose-sensing system in the serum. When the current became stable, the current value of 96 nA was measured for 5.8 mM glucose originally contained in serum.

Example 13.3—Electrode with Maltose-Blocking Layer (0.1 mM, 10 mV/sec)

Figure 25:
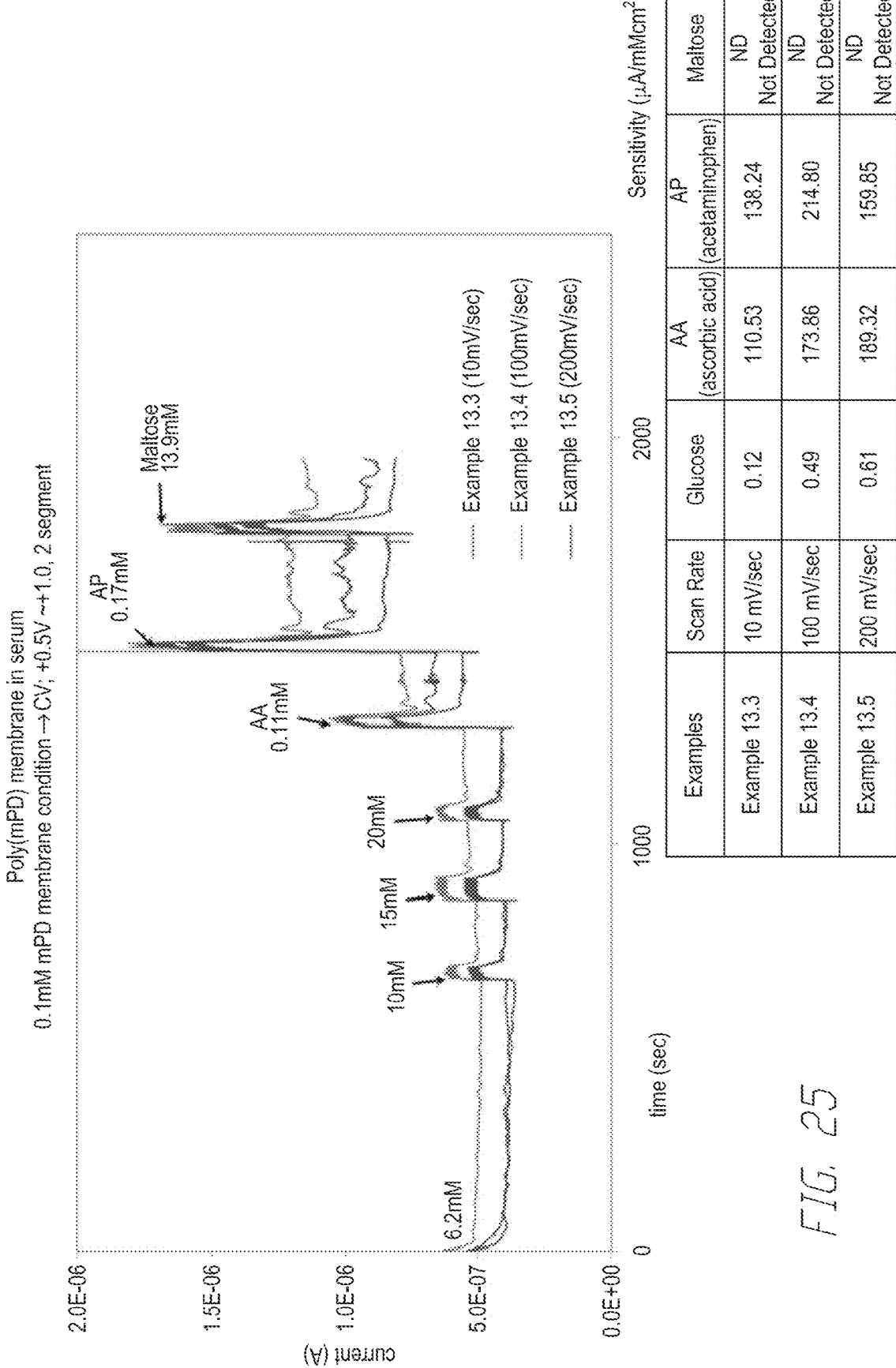

In the system prepared in Example 13.2, the glucose stock solution prepared as in Example 9.1 was added to the serum to make the total glucose concentration 10 mM in the serum. Subsequently, the glucose stock solution added further to make the total glucose concentration 15 mM and 20 mM in the serum with a time interval between the additions. Subsequently, the ascorbic acid aqueous solution prepared in Example 9.1 was added to the serum to make 0.11 mM ascorbic acid in the serum. Subsequently, the acetaminophen aqueous solution prepared in Example 9.1 was added to the resulting serum to make 0.17 mM acetaminophen in the serum. Further subsequently, the maltose aqueous solution prepared in Example 9.1 was added to the resulting serum to make 13.9 mM maltose in the serum. Immediately after each addition, the serum was stirred for 3-4 seconds, which caused temporary peaks of electric current. FIG. 25 shows the electric current monitored in this example in red. A change of electric current was observed in response to each addition of glucose, ascorbic acid (AA) and acetaminophen (AP). However, after the addition of maltose, no electric current change greater than 5 nA/mMcm$^2$ was observed except the peaks caused by stirring. Accordingly, the maltose-blocking layer in this example effectively blocked maltose while not interrupting sensing of glucose.

Example 13.4—Electrode with Maltose-Blocking Layer (0.1 mM, 100 mV/sec)

Examples 13.1-13.3 were repeated except that the working electrode 103 included a maltose-blocking layer that was prepared as in Example 12.4 (using 0.1 mM mPD solution at scanning rate of 100 mV/sec). FIG. 25 shows the electric current monitored in this example in green. A change of electric current was observed in response to each addition of glucose, ascorbic acid and acetaminophen. However, after the addition of maltose, no electric current change greater than 5 nA/mMcm$^2$ was observed except the peaks caused by stirring. The maltose-blocking layer in this example effectively blocked maltose while not interrupting sensing of glucose.

Example 13.5—Electrode with Maltose-Blocking Layer (0.1 mM, 200 mV/sec)

Examples 13.1-13.3 were repeated except that the working electrode 103 included a maltose-blocking layer that was prepared as in Example 12.5 (using 0.1 mM mPD solution at scanning rate of 200 mV/sec). FIG. 25 shows electric current monitored in this example in purple. A change of electric current was observed in response to each addition of glucose, ascorbic acid and acetaminophen. However, after the addition of maltose, no electric current change greater than 5 nA/mMcm$^2$ was observed except the peaks caused by stirring. The maltose-blocking layer in this example effectively blocked maltose while not interrupting sensing of glucose.

Example 13.6—Electrode with Maltose-Blocking Layer (0.3 mM, 10 mV/sec)

Figure 26:
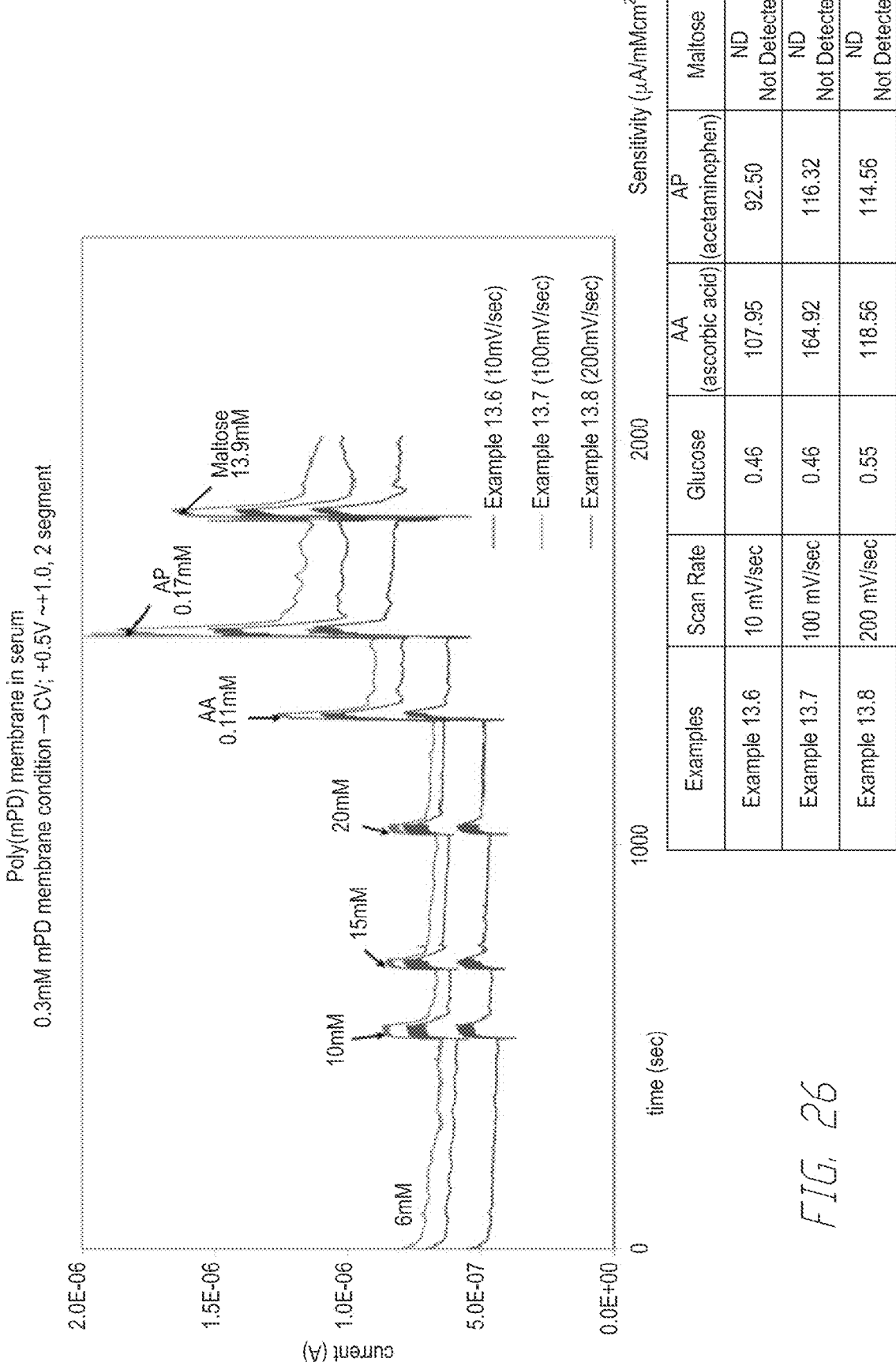

Examples 13.1-13.3 were repeated except that the working electrode included maltose-blocking layer prepared in Example 12.6 (using 0.3 mM mPD solution at scanning rate of 10 mV/sec). FIG. 26 shows the electric current monitored in this example in red. A change of electric current was observed in response to each addition of glucose, ascorbic acid and acetaminophen. However, after the addition of maltose, no electric current change greater than 5 nA/mMcm$^2$ was observed except the peaks caused by stirring. The maltose-blocking layer in this example effectively blocked maltose while not interrupting sensing of glucose.

Example 13.7—Electrode with Maltose-Blocking Layer (0.3 mM, 100 mV/sec)

Examples 13.1-13.3 were repeated except that the working electrode included maltose-blocking layer prepared in Example 12.7 (using 0.3 mM mPD solution at scanning rate of 100 mV/sec). FIG. 26 shows the electric current monitored in this example in green. A change of electric current was observed in response to each addition of glucose, ascorbic acid and acetaminophen. However, after the addition of maltose, no electric current change greater than 5 nA/mMcm$^2$ was observed except the peaks caused by stirring. The maltose-blocking layer in this example effectively blocked maltose while not interrupting sensing of glucose.

Example 13.8—Electrode with Maltose-Blocking Layer (0.3 mM, 200 mV/sec)

Examples 13.1-13.3 were repeated except that the working electrode included maltose-blocking layer prepared in Example 12.8 (using 0.3 mM mPD solution at scanning rate of 200 mV/sec). FIG. 26 shows the electric current monitored in this example in purple. A change of electric current was observed in response to each addition of glucose, ascorbic acid and acetaminophen. However, after the addition of maltose, no electric current change greater than 5 nA/mMcm$^2$ was observed except the peaks caused by stirring. The maltose-blocking layer in this example effectively blocked maltose while not interrupting sensing of glucose.

Example 13.9—Electrode with Maltose-Blocking Layer (0.5 mM, 10 mV/sec)

Examples 13.1-13.3 were repeated except that the working electrode included maltose-blocking layer prepared in Example 12.9 (using 0.5 mM mPD solution at scanning rate of 10 mV/sec). FIG. 27 shows the electric current monitored in this example in red. A change of electric current was observed in response to each addition of glucose, ascorbic acid and acetaminophen. However, after the addition of maltose, no electric current change greater than 5 nA/mMcm$^2$ was observed except the peaks caused by stirring. The maltose-blocking layer in this example effectively blocked maltose while not interrupting sensing of glucose.

Example 13.10—Electrode with Maltose-Blocking Layer (0.5 mM, 100 mV/sec)

Examples 13.1-13.3 were repeated except that the working electrode included maltose-blocking layer prepared in Example 12.9 (using 0.5 mM mPD solution at scanning rate of 100 mV/sec). FIG. 27 shows the electric current monitored in this example in green. A change of electric current was observed in response to each addition of glucose, ascorbic acid and acetaminophen. However, after the addition of maltose, no electric current change greater than 5 nA/mMcm$^2$ was observed except the peaks caused by stirring. The maltose-blocking layer in this example effectively blocked maltose while not interrupting sensing of glucose.

Example 13.11—Electrode with Maltose-Blocking Layer (0.5 mM, 200 mV/sec)

Examples 13.1-13.3 were repeated except that the working electrode included maltose-blocking layer prepared in Example 12.11 (using 0.5 mM mPD solution at scanning rate of 200 mV/sec). FIG. 27 shows the electric current monitored in this example in purple. A change of electric current was observed in response to each addition of glucose, ascorbic acid and acetaminophen. However, after the addition of maltose, no electric current change greater than 5 nA/mMcm$^2$ was observed except the peaks caused by stirring. The maltose-blocking layer in this example effectively blocked maltose while not interrupting sensing of glucose.

Example 13.12—Electrode with Maltose-Blocking Layer (1.0 mM, 10 mV/sec)

Examples 13.1-13.3 were repeated except that the working electrode included maltose-blocking layer that was prepared in Example 12.12 (using 1.0 mM mPD solution at scanning rate of 10 mV/sec) and further subjected to electric shock as in Example 12.13. FIG. 28 shows the electric current monitored in this example in red. A change of electric current was observed in response to each addition of glucose, ascorbic acid and acetaminophen. However, after the addition of maltose, no electric current change greater than 5 nA/mMcm$^2$ was observed except the peaks caused by stirring. The maltose-blocking layer in this example effectively blocked maltose while not interrupting sensing of glucose.

Example 13.13—Electrode with Maltose-Blocking Layer (1.0 mM, 100 mV/sec)

Examples 13.1-13.3 were repeated except that the working electrode included maltose-blocking layer prepared in Example 12.14 (using 1.0 mM mPD solution at scanning rate of 100 mV/sec) and further with electric shock as in Example 12.13. FIG. 28 shows the electric current monitored in this example in green. A change of electric current was observed in response to each addition of glucose, ascorbic acid and acetaminophen. However, after the addition of maltose, no electric current change greater than 5 $nA/mMcm^2$ was observed except the peaks caused by stirring. The maltose-blocking layer in this example effectively blocked maltose while not interrupting sensing of glucose.

Example 13.14—Electrode with Maltose-Blocking Layer (1.0 mM, 200 mV/sec)

Examples 13.1-13.3 were repeated except that the working electrode included maltose-blocking layer prepared in Example 12.15 (using 1.0 mM mPD solution at scanning rate of 200 mV/sec) and further with electric shock. FIG. 28 shows the electric current monitored in this example in purple. A change of electric current was observed in response to each addition of glucose, ascorbic acid and acetaminophen. However, after the addition of maltose, no electric current change greater than 5 $nA/mMcm^2$ was observed except the peaks caused by stirring. The maltose-blocking layer in this example effectively blocked maltose while not interrupting sensing of glucose.

Example 13.15—Electrode with Maltose-Blocking Layer (2.0 mM, 10 mV/sec)

Figure 29:
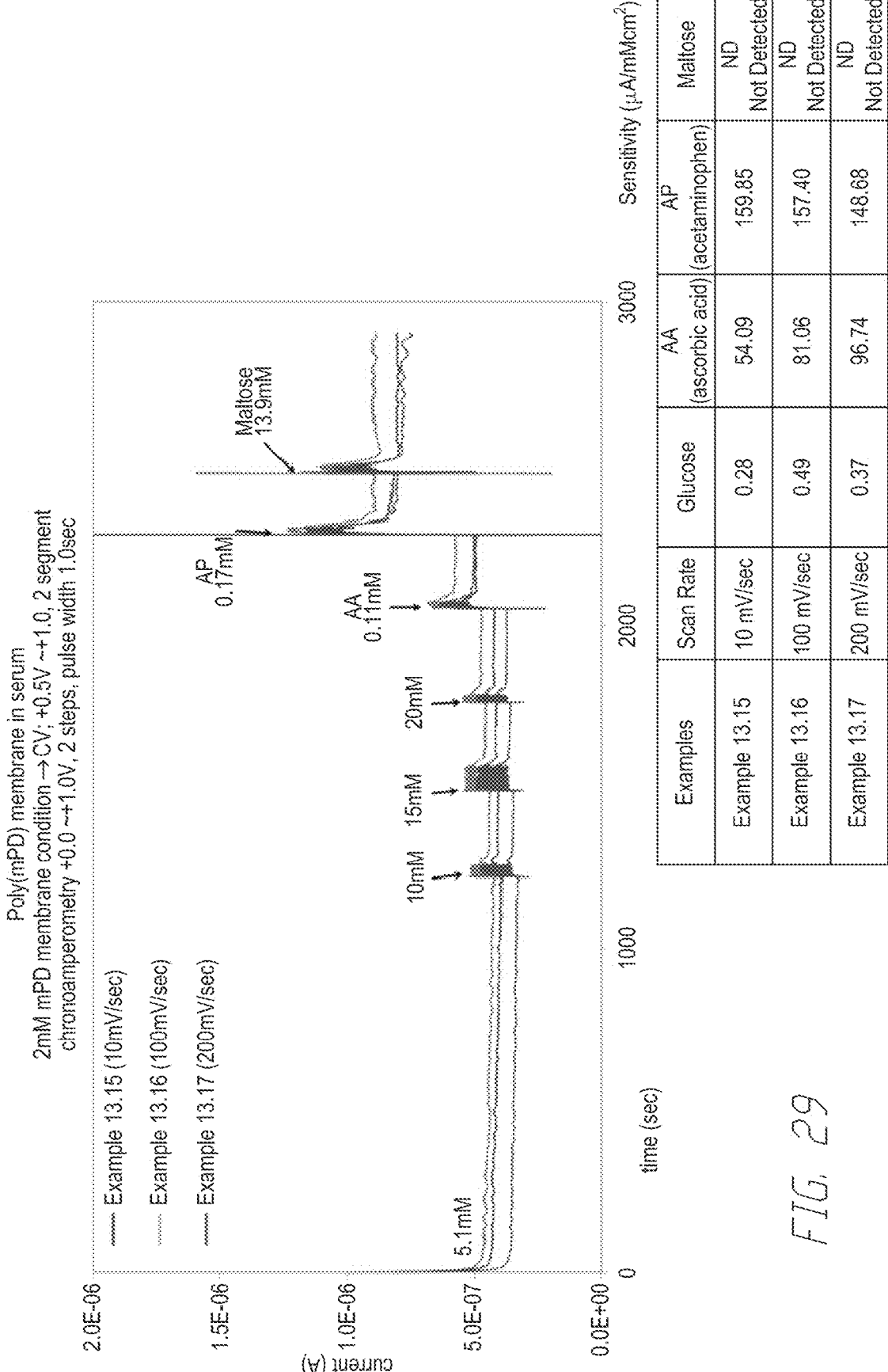

Examples 13.1-13.3 were repeated except that the working electrode included maltose-blocking layer that was prepared in Example 12.16 (using 2.0 mM mPD solution at scanning rate of 10 mV/sec) and further with electric shock as in Example 12.15. FIG. 29 shows the electric current monitored in this example in red. A change of electric current was observed in response to each addition of glucose, ascorbic acid and acetaminophen. However, after the addition of maltose, no electric current change greater than 5 $nA/mMcm^2$ was observed except the peaks caused by stirring. The maltose-blocking layer in this example effectively blocked maltose while not interrupting sensing of glucose.

Example 13.16—Electrode with Maltose-Blocking Layer (2.0 mM, 100 mV/sec)

Examples 13.1-13.3 were repeated except that the working electrode included maltose-blocking layer prepared in Example 12.17 (using 2.0 mM mPD solution at scanning rate of 100 mV/sec) and further with electric shock as in Example 12.15. FIG. 29 shows the electric current monitored in this example in green. A change of electric current was observed in response to each addition of glucose, ascorbic acid and acetaminophen. However, after the addition of maltose, no electric current change greater than 5 $nA/mMcm^2$ was observed except the peaks caused by stirring. The maltose-blocking layer in this example effectively blocked maltose while not interrupting sensing of glucose.

Example 13.17—Electrode with Maltose-Blocking Layer (2.0 mM, 200 mV/sec)

Examples 13.1-13.3 were repeated except that the working electrode included maltose-blocking layer prepared in Example 12.18 (using 2.0 mM mPD solution at scanning rate of 200 mV/sec) and further with electric shock as in Example 12.15. FIG. 29 shows the electric current monitored in this example in purple. A change of electric current was observed in response to each addition of glucose, ascorbic acid and acetaminophen. However, after the addition of maltose, no electric current change greater than 5

$nA/mMcm^2$ was observed except the peaks caused by stirring. The maltose-blocking layer in this example effectively blocked maltose while not interrupting sensing of glucose.

Example 13.18—Electrode with Maltose-Blocking Layer (5.0 mM, 10 mV/sec)

Figure 30:
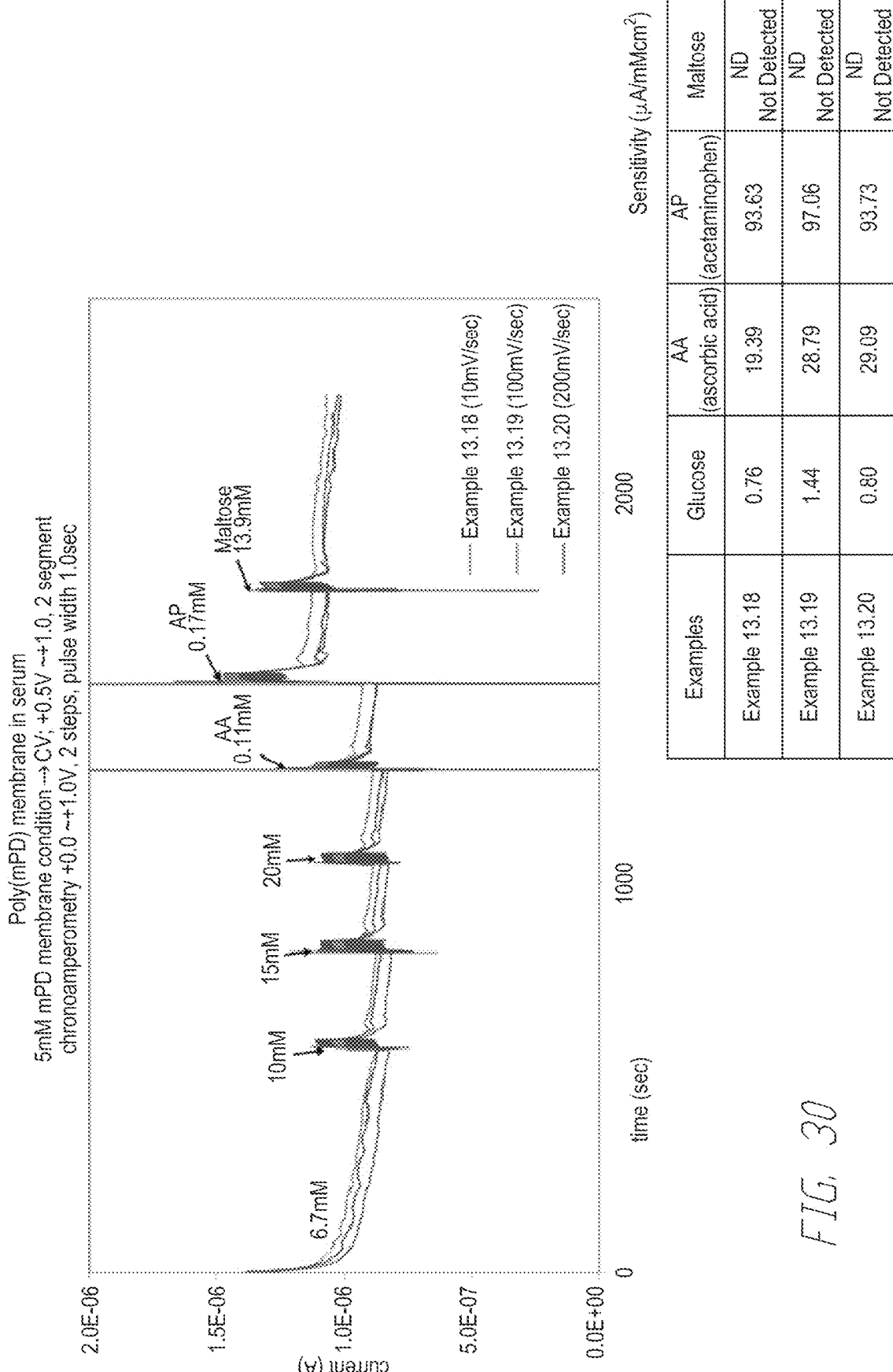

Examples 13.1-13.3 were repeated except that the working electrode included maltose-blocking layer that was prepared in Example 12.19 (using 5.0 mM mPD solution at scanning rate of 10 mV/sec) and further with electric shock as in Example 12.15. FIG. 30 shows the electric current monitored in this example in red. A change of electric current was observed in response to each addition of glucose, ascorbic acid and acetaminophen. However, after the addition of maltose, no electric current change greater than 5 $nA/mMcm^2$ was observed except the peaks caused by stirring. The maltose-blocking layer in this example effectively blocked maltose while not interrupting sensing of glucose.

Example 13.19—Electrode with Maltose-Blocking Layer (5.0 mM, 100 mV/sec)

Examples 13.1-13.3 were repeated except that the working electrode included maltose-blocking layer prepared in Example 12.20 (using 5.0 mM mPD solution at scanning rate of 100 mV/sec) and further with electric shock as in Example 12.15. FIG. 30 shows the electric current monitored in this example in green. A change of electric current was observed in response to each addition of glucose, ascorbic acid and acetaminophen. However, after the addition of maltose, no electric current change greater than 5 $nA/mMcm^2$ was observed except the peaks caused by stirring. The maltose-blocking layer in this example effectively blocked maltose while not interrupting sensing of glucose.

Example 13.20—Electrode with Maltose-Blocking Layer (5.0 mM, 200 mV/sec)

Examples 13.1-13.3 were repeated except that the working electrode included maltose-blocking layer prepared in Example 12.21 (using 5.0 mM mPD solution at scanning rate of 200 mV/sec) and further with electric shock as in Example 12.15. FIG. 30 shows the electric current monitored in this example in purple. A change of electric current was observed in response to each addition of glucose, ascorbic acid and acetaminophen. However, after the addition of maltose, no electric current change greater than 5 $nA/mMcm^2$ was observed except the peaks caused by stirring. The maltose-blocking layer in this example effectively blocked maltose while not interrupting sensing of glucose.

Example 13.21—Electrode with Maltose-Blocking Layer (1.0 mM, 10 mV/sec)

Example 13.12 is repeated except that the poly-mPD layer prepared in Example 12.12 (using 1.0 mM mPD solution at scanning rate of 10 mV/sec) is not subjected to electric shock.

Example 13.22—Electrode with Maltose-Blocking Layer (1.0 mM, 100 mV/sec)

Example 13.12 is repeated except that the poly-mPD layer prepared in Example 12.14 (using 1.0 mM mPD solution at scanning rate of 100 mV/sec) is not subjected to electric shock.

Example 13.23—Electrode with Maltose-Blocking Layer (1.0 mM, 200 mV/sec)

Example 13.12 is repeated except that the poly-mPD layer prepared in Example 12.15 (using 1.0 mM mPD solution at scanning rate of 200 mV/sec) is not subjected to electric shock.

Example 13.24—Electrode with Maltose-Blocking Layer (2.0 mM, 10 mV/sec)

Example 13.12 is repeated except that the poly-mPD layer prepared in Example 12.16 (using 2.0 mM mPD solution at scanning rate of 10 mV/sec) is not subjected to electric shock. No change of electric current is observed in response to each addition of glucose, which means the poly-mPD layer effectively blocks glucose.

Example 13.25—Electrode with Maltose-Blocking Layer (2.0 mM, 100 mV/sec)

Example 13.12 is repeated except that the poly-mPD layer prepared in Example 12.17 (using 2.0 mM mPD solution at scanning rate of 100 mV/sec) is not subjected to electric shock. No change of electric current is observed in response to each addition of glucose, which means the poly-mPD layer effectively blocks glucose.

Example 13.26—Electrode with Maltose-Blocking Layer (2.0 mM, 200 mV/sec)

Example 13.12 is repeated except that the poly-mPD layer prepared in Example 12.18 (using 2.0 mM mPD solution at scanning rate of 200 mV/sec) is not subjected to electric shock. No change of electric current is observed in response to each addition of glucose, which means the poly-mPD layer effectively blocks glucose.

Example 13.27—Electrode with Maltose-Blocking Layer (5.0 mM, 10 mV/sec)

Example 13.12 is repeated except that the poly-mPD layer prepared in Example 12.19 (using 5.0 mM mPD solution at scanning rate of 10 mV/sec) is not subjected to electric shock. No change of electric current is observed in response to each addition of glucose, which means the poly-mPD layer effectively blocks glucose.

Example 13.28—Electrode with Maltose-Blocking Layer (5.0 mM, 100 mV/sec)

Example 13.12 is repeated except that the poly-mPD layer prepared in Example 12.20 (using 5.0 mM mPD solution at scanning rate of 100 mV/sec) is not subjected to electric shock. No change of electric current is observed in response to each addition of glucose, which means the poly-mPD layer effectively blocks glucose.

Example 13.29—Electrode with Maltose-Blocking Layer (5.0 mM, 200 mV/sec)

Example 13.12 is repeated except that the poly-mPD layer prepared in Example 12.21 (using 5.0 mM mPD solution at scanning rate of 200 mV/sec) is not subjected to electric shock. No change of electric current is observed in response to each addition of glucose, which means the poly-mPD layer effectively blocks glucose.

Alternative Electric Shock

Example 14.1—Electric Shock in Two Pulses

Example 12.13 is repeated except that two pulses with the pulse width of 0.5 sec. with an interval of 0.5 sec.

Example 14.2—Electric Shock in Two Pulses

Example 14.1 is repeated except that each pulse is from +0.0 V to +2.0 V.

Example 14.3—Electric Shock in Multiple Pulses

Example 12.13 is repeated except that a series of 10 pulses with the pulse width of 0.1 sec. with an interval of 0.1 sec. between two pulses.

Example 14.4—Electric Shock in Multiple Pulses

Example 14.1 is repeated except that each pulse is from +0.0 V to +2.0 V.

Example 14.5—Electric Shock in a Single Ramp

Example 12.13 is repeated except that the electric potential gradually increases from +0.0 V to +1.0 V, during the period of 1 sec.

Example 14.6—Electric Shock in Multiple Ramps

Example 14.5 is repeated except that the ramp electric potential is repeated 5 times with an interval of 0.1 between two ramps.

Example 14.7—Electric Shock in a Single Ramp

Example 12.13 is repeated except that the electric potential gradually increases from +0.0 V to +2.0 V, during the period of 2 sec.

Example 14.8—Electric Shock in Multiple Ramps

Example 14.7 is repeated except that the ramp electric potential is repeated 5 times with an interval of 0.1 between two ramps.

Conditioning Working Electrode

Example 15.1—Preparing Glucose-Sensing System in Serum

Example 10.2 was repeated to prepare an electrochemical cell for glucose sensing in serum. The working electrode 103 was one of the electrodes 1607 (including platinum nanoporous layer 1609) prepared in Example 8.4 and does not include an electrolyte ion-blocking layer.

Example 15.2—Conditioning Working Electrode (No Electrolyte Ion-Blocking Layer)

Figure 42A:
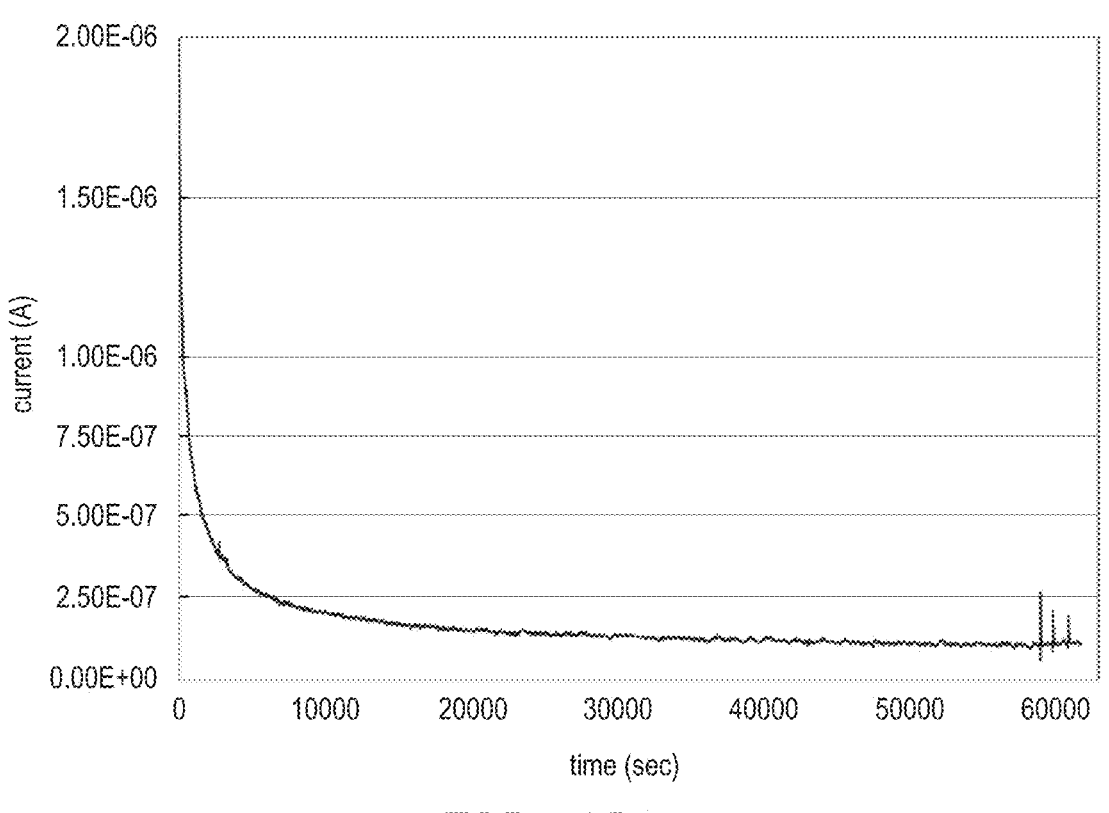
FIG. 42A is a profile of electric current generated by oxidation of glucose according to an embodiment in which the working electrode does not include an electrolyte ion-blocking layer.
Figure 42B:
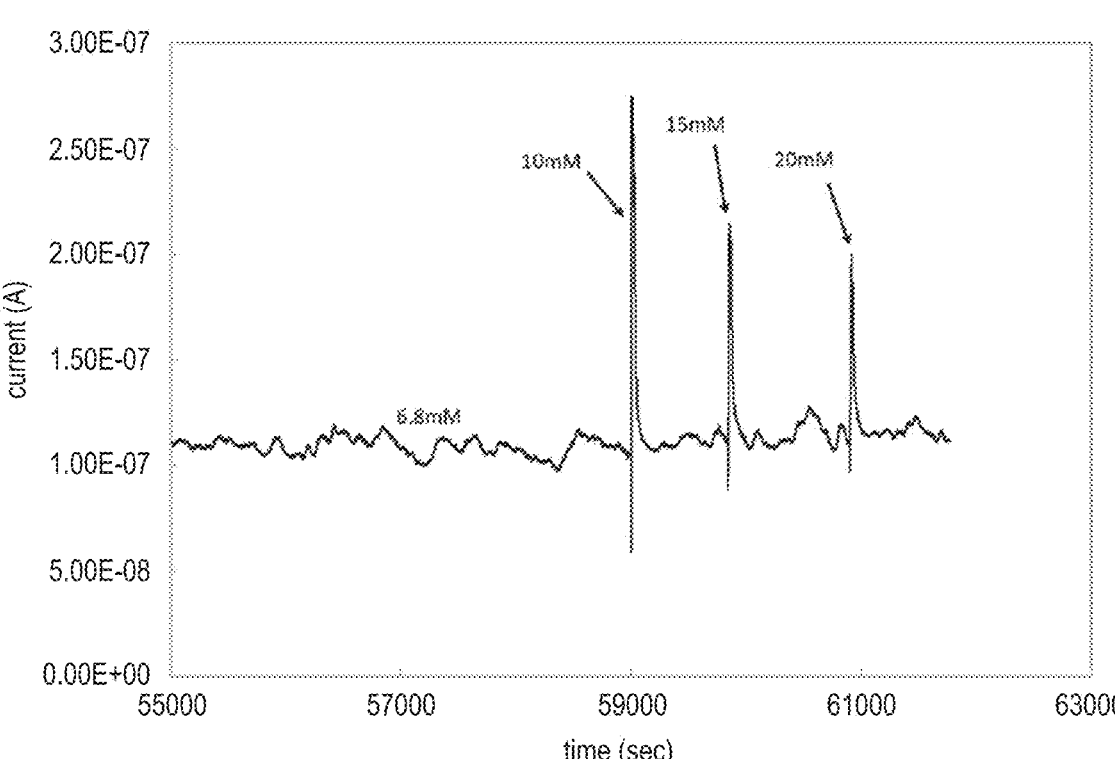
FIG. 42B is an enlarged view of a portion of the profile of FIG. 42A.

In the electrochemical cell prepared in Example 15.1, the bias voltage of 0.4 V was applied between the working electrode 103 and the reference electrode 106. Unlike in Example 10.3, immediately upon applying the bias voltage, electric current from the working electrode was continuously measured. FIG. 42A shows a profile of the electric current profile measured from the electrochemical cell, in which the working electrode 103 does not include an electrolyte ion-blocking layer. Referring to FIG. 42A, at 10,000 seconds (about 3 hours), 20,000 seconds and 30,000 seconds, the electric current still decreases at a significant rate. FIG. 42B is an enlarged view of the profile of FIG. 42A and shows that the glucose stock solution prepared as in Example 9.1 was added well after the completion of conditioning of the working electrode.

Example 15.3—Preparing Working Electrode with PMMA Electrolyte Ion-Blocking Layer PMMA purchased from Sigma-Aldrich (Product No. 445746) was dissolved in dimethylformamide (DMF) to provide 2 wt % PMMA solution. Using a micro-syringe, 0.2 μL of the PMMA solution was dropped on the platinum nanoporous layer 1609 of one of the electrodes 1607 prepared in Example 8.4. When the solvent dried off, a PMMA electrolyte ion-blocking layer 505 was formed on the platinum nanoporous layer 1609.

Example 15.4—Preparing Glucose-Sensing System in Serum

Example 10.2 was repeated for preparing an electrochemical cell for glucose sensing in serum except that the working electrode with PMMA electrolyte ion-blocking layer prepared in Example 15.1 was used as working electrode 103.

Example 15.5—Conditioning Working Electrode

Figure 43:
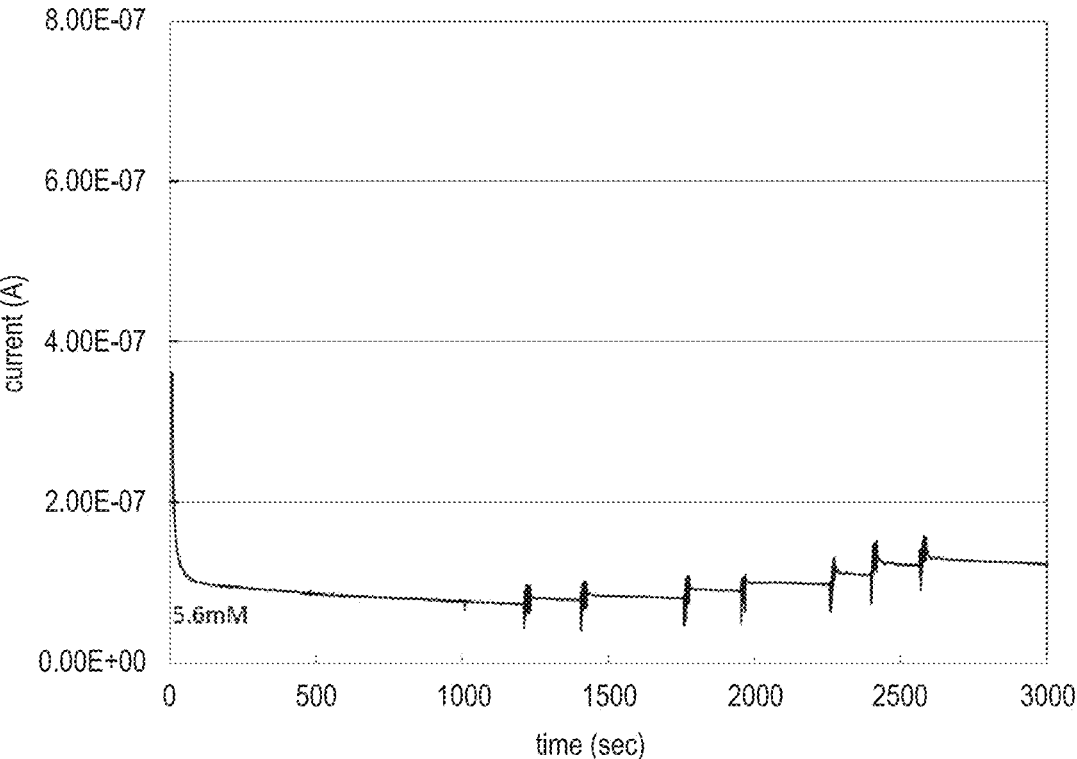
FIG. 43 is a profile of electric current generated by oxidation of glucose according to an embodiment in which the working electrode includes an electrolyte ion-blocking layer.

In the electrochemical cell prepared in Example 15.4, the bias voltage of 0.4 V was applied between the working electrode 103 and the reference electrode 106. Immediately upon applying the bias voltage, electric current from the working electrode was continuously measured. FIG. 43 shows a profile of the electric current measured from the electrochemical cell, in which the working electrode 103 includes an electrolyte ion-blocking layer. The glucose stock solution prepared as in Example 9.1 was added well after the completion of conditioning of the working electrode. The peaks in FIG. 43 represent stirring after each addition.

Example 15.6—Comparing Conditioning Time

Figure 44:
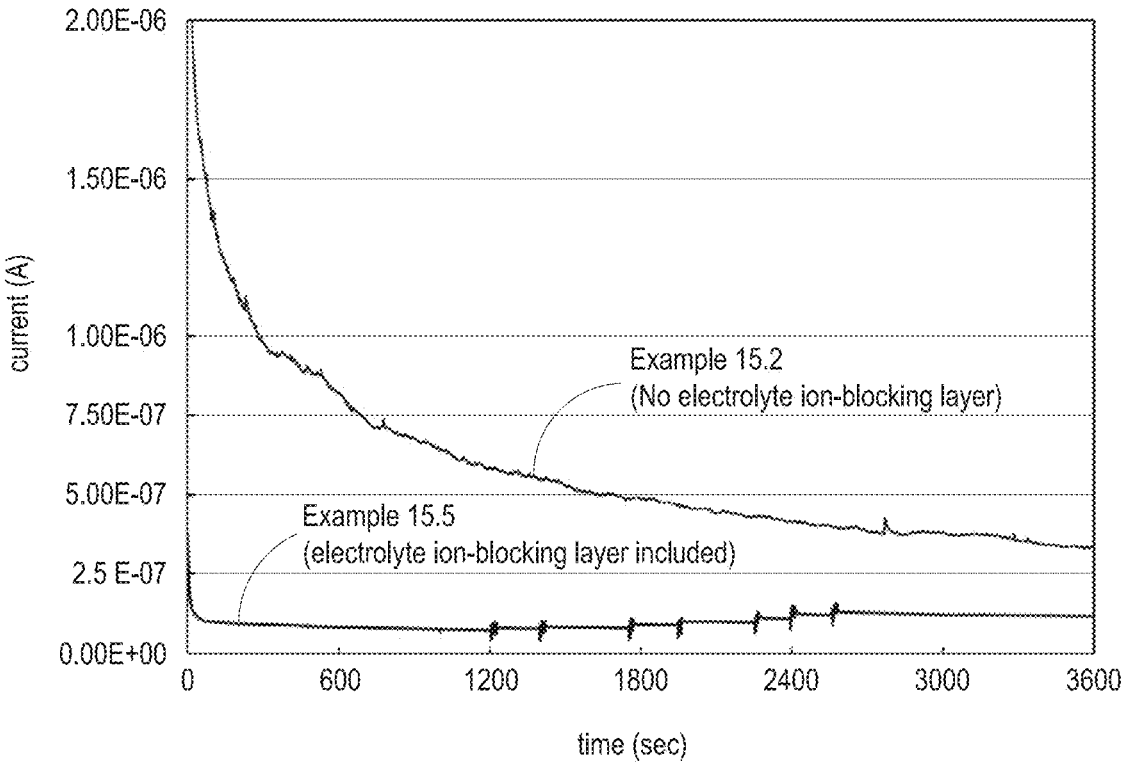
FIG. 44 is a comparison of time for conditioning working electrodes with and without an electrolyte ion-blocking layer.

FIG. 44 overlays the electric current profiles of FIG. 42 (Example 15.2) and FIG. 43 (Example 15.5). The electric current of Example 15.5 (including an electrolyte ion-blocking layer) has settled and stabilized in about 600 sec whereas the electric current of Example 15.2 (no electrolyte ion-blocking layer) decreases at a significant rate in the same time frame.

Example 15.7—Preparing Working Electrode with PHEMA Layer

PHEMA purchased from Sigma-Aldrich (Product No. 529265) was dissolved in dimethylformamide (DMF) to provide 2 wt % PHEMA solution. Using a micro-syringe, 0.2 μL of the PHEMA solution was dropped on the platinum nanoporous layer 1609 of one of the electrodes 1607 prepared in Example 8.4. When the solvent dried off, a PHEMA electrolyte ion-blocking layer 505 was formed on the platinum nanoporous layer 1609.

Example 15.8—Preparing Working Electrode with PMMA-EG-PMMA Layer

PMMA-EG-PMMA purchased from Sigma-Aldrich (Product No. 463183) was dissolved in dimethylformamide (DMF) to provide 2 wt % PMMA-EG-PMMA solution. Using a micro-syringe, 0.2 μL of the PMMA-EG-PMMA solution was dropped on the platinum nanoporous layer 1609 of one of the electrodes 1607 prepared in Example 8.4. When the solvent dried off, a PMMA-EG-PMMA electrolyte ion-blocking layer 505 was formed on the platinum nanoporous layer 1609.

Example 15.8—Preparing Glucose-Sensing Systems and Conditioning in Serum

Electrochemical cells for glucose sensing in serum were prepared by repeating Example 15.4 except that the working electrodes prepared in Examples 15.7 and 15.8 were used as working electrode 103. Further, Example 15.5 was repeated for the prepared electrochemical cells.

Making CGM Subcutaneous Electrode Unit

Example 16.1—Forming Conductive Layer on Base

A polyimide film with the thickness of 150 μm was used as a base substrate 503. A silver layer 1603 was printed on the polyimide film to provide about 20 μm thickness of silver conductive elements 110C, 110W and 110R in the shapes as illustrated in FIG. 35. Subsequently, a conductive carbon layer 1605 was printed on the silver conductive elements 110C and 110W in the thickness of about 20 μm. No carbon layer was formed on the silver layer conductive element 110R.

Example 16.2—Placing Insulation Layer and Cutting

A polyimide film with the thickness of 50 μm was used as an insulation layer 707. The polyimide film was cut in a size to cover the intermediate product of FIG. 35 while exposing the terminal portion 705. The polyimide film was punctured to provide three openings for exposing areas for working, reference and counter electrodes. Subsequently, the pre-cut polyimide was placed over the intermediate product of FIG. 35 such that the adhesive layer contacts the polyimide base 503 for providing the intermediate product of FIG. 36. Subsequently, the polyimide base 503 and polyimide insulation layer 707 outside the conductive elements were cut to provide an intermediate product of FIG. 37.

Example 16.3—Forming Clustered Nanoporous Layer

The cluster colloid obtained in Example 5.1 was diluted to 60 mg/ml with purified water. Using a micro-syringe, 0.2 μL of the diluted cluster colloid was dropped on the carbon layer 1605 exposed through one opening for the working electrode 501 of the intermediate product prepared in Example 16.2. The cluster colloid dropped on the carbon layer 1605 was dried to provide the clustered nanoporous layer 117, resulting in an intermediate product of FIG. 38A.

Example 16.4—Forming Electrolyte Ion-Blocking Layer

PMMA purchased from Sigma-Aldrich (Product No. 445746) was dissolved in dimethylformamide (DMF) to provide 2 wt % PMMA solution. Using a micro-syringe, 0.2 μL of the PMMA solution was dropped on the nanoporous layer 117 of the intermediate product prepared in Example 16.3. When the solvent dried off, the PMMA electrolyte ion-blocking layer 505 was formed on the nanoporous layer 117.

Example 16.5—Forming Biocompatibility Layer

A biocompatibility layer (pHEMA) is formed on the electrolyte ion-blocking layer 505 as illustrated in FIG. 38B, resulting in a non-enzymatic CGM electrode unit of FIG. 33.

Example 16.6—Forming Biocompatibility Layer pHEMA purchased from Sigma-Aldrich (Product No. 192066) was dissolved in dimethylsulfoxide (DMSO) to provide 0.5 wt % pHEMA solution. Using a micro-syringe, 1.0 μL of the pHEMA solution was dropped on the electrolyte ion-blocking layer 505 of the intermediate product prepared in Example 16.4. When the solvent dried off, the pHEMA biocompatibility layer 507 was formed as illustrated in FIG. 38B, resulting in a non-enzymatic CGM electrode unit 701 of FIG. 33.

CGM Animal Testing

Example 17.1—Preparation for CGM Animal Testing

Figure 45A:
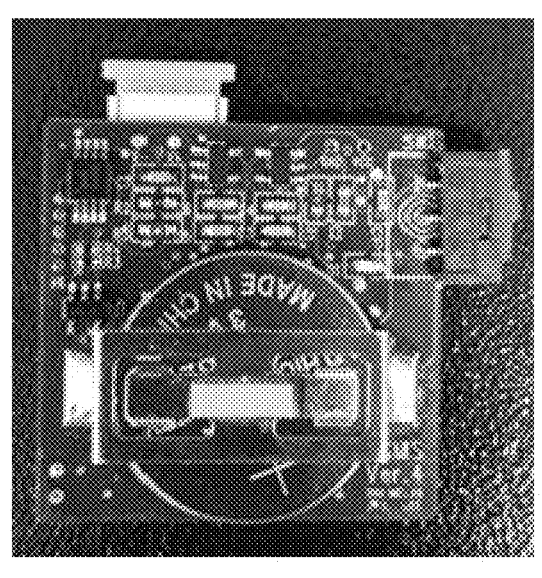
FIGS. 45A, 45B and 45C are photographs of a potentiostat according to an embodiment.
Figure 45B:
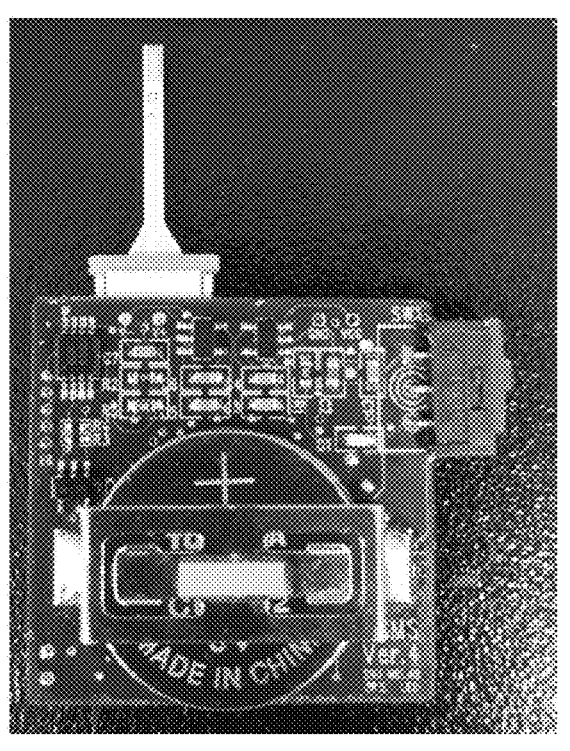
Figure 45C:
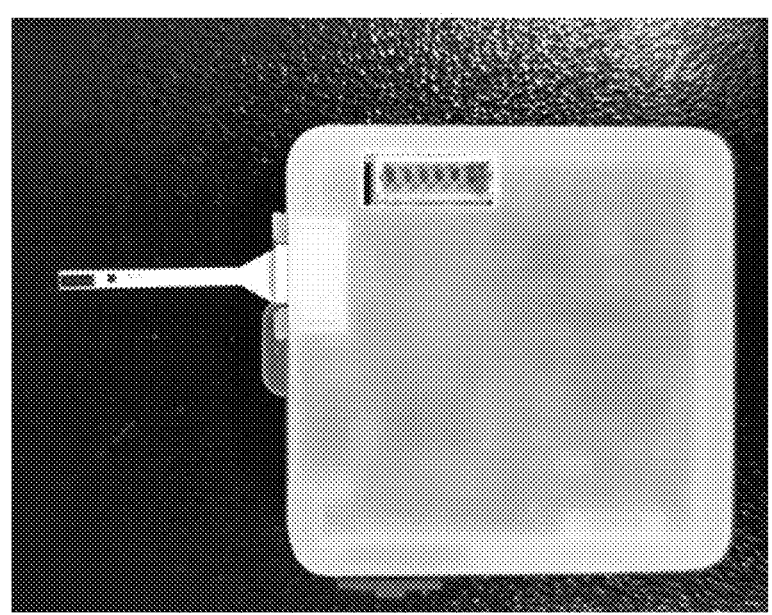

The non-enzymatic CGM electrode unit prepared in Example 16.6 was subcutaneously inserted into a rat's body such that the electrodes 103, 105 and 106 contact interstitial fluid of the rat. The CGM electrode unit 701 was connected to a UXN potentiostat developed by UXN Co., Ltd. (Applicant of the present application) and Seoul National University Hospital. FIG. 45A is a photograph of the UXN potentiostat. FIG. 45B is a photograph showing that the CGM electrode unit 701 is connected to the UXN potentiostat of FIG. 45A. FIG. 45C is a photograph showing that the UXN potentiostat with its case. The UXN potentiostat includes a wireless module for wirelessly communicating with a computer and can be wirelessly controlled by the computer. A glucose solution was prepared for injecting into the rat's vein to cause changes of the glucose level in the rat's blood and interstitial fluid.

Example 17.2—Continuous Monitoring of Rat's Glucose Level

Subcutaneous insertion of the CGM electrode unit 701 was maintained for 5 consecutive days. On the first day, the glucose solution was injected to the rat twice. On the following days, the glucose solution was injected once a day. The UXN potentiostat measured the electric current from the CGM electrode unit 701 over a time span of about 1.5 hours after the (first) injection each day. Also, every 2-5 minutes during the time span of about 1.5 hours, a small amount of the rat's blood was taken from its tail and applied to a test strip for Roche Accu Chek® blood glucose meter, which provided a glucose concentration in the blood.

Example 17.3—Plotting CGM Measurements and Blood Glucose of Rat

Figure 46:
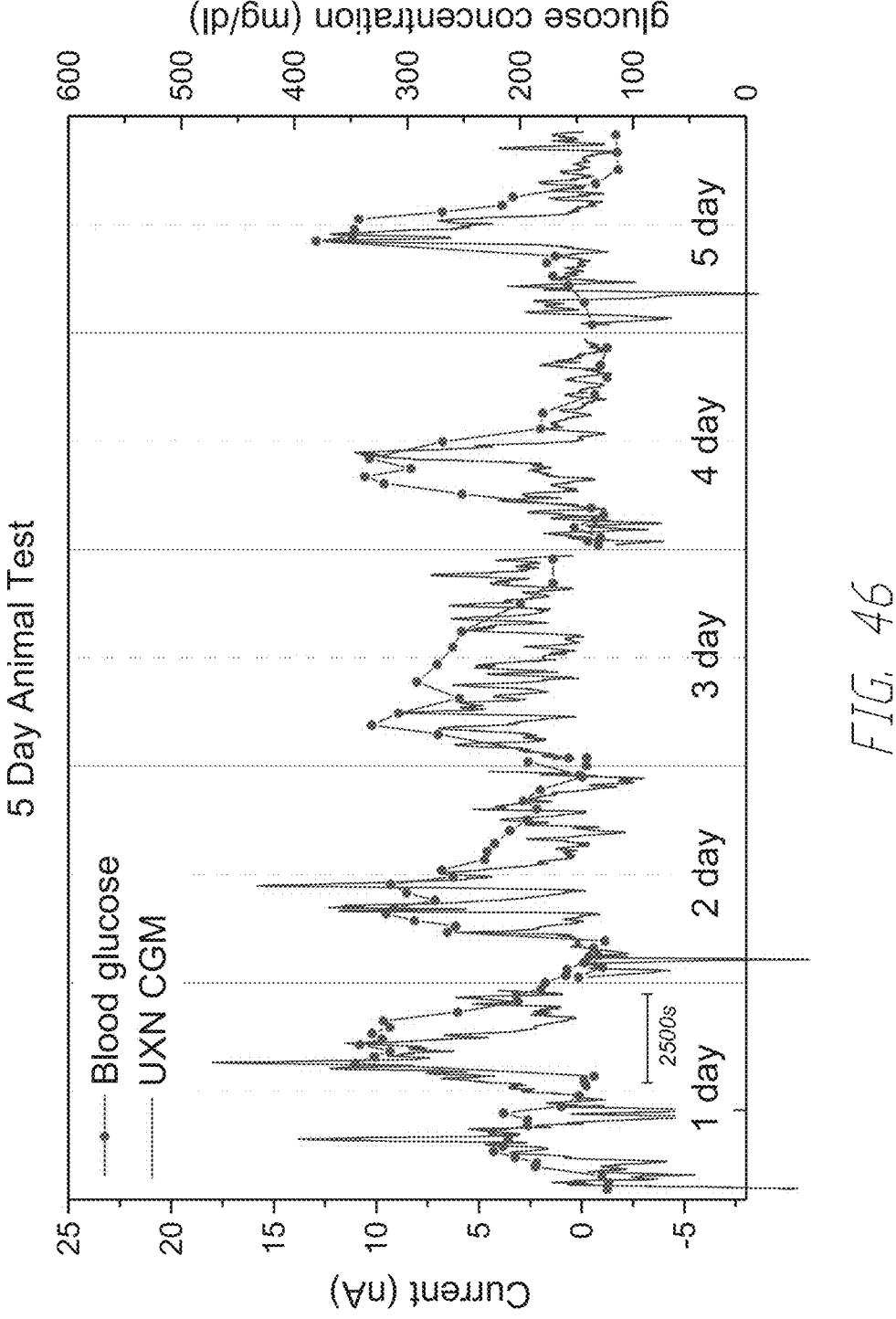
FIG. 46 is a graph showing CGM monitoring of a rat's glucose level using a non-enzymatic CGM electrode module according to an embodiment.

FIG. 46 shows the electric current from the CGM electrode module in blue that was measured by the UXN potentiostat in Example 17.2. The red dots of FIG. 46 represent the blood glucose concentrations obtained from the Roche Accu Chek® blood glucose meter. Given that there is a time lag of about 10 minutes between the glucose level in interstitial fluid and the glucose level in blood, the data were calibrated by shifting blue signals shifted relative to the red dots in time. It is understood that sharp peaks in the blue signals are primarily from the rat's physical movements during the measurements. Based on the graph of FIG. 45, there appears to be a strong correlation between the blood glucose concentrations using the Roche Accu Chek® blood glucose meter and the CGM monitoring using the non-enzymatic CGM electrode unit 701 prepared in Example 16.6.

Example 17.4—Clarke Error Grid Analysis

Figure 47:
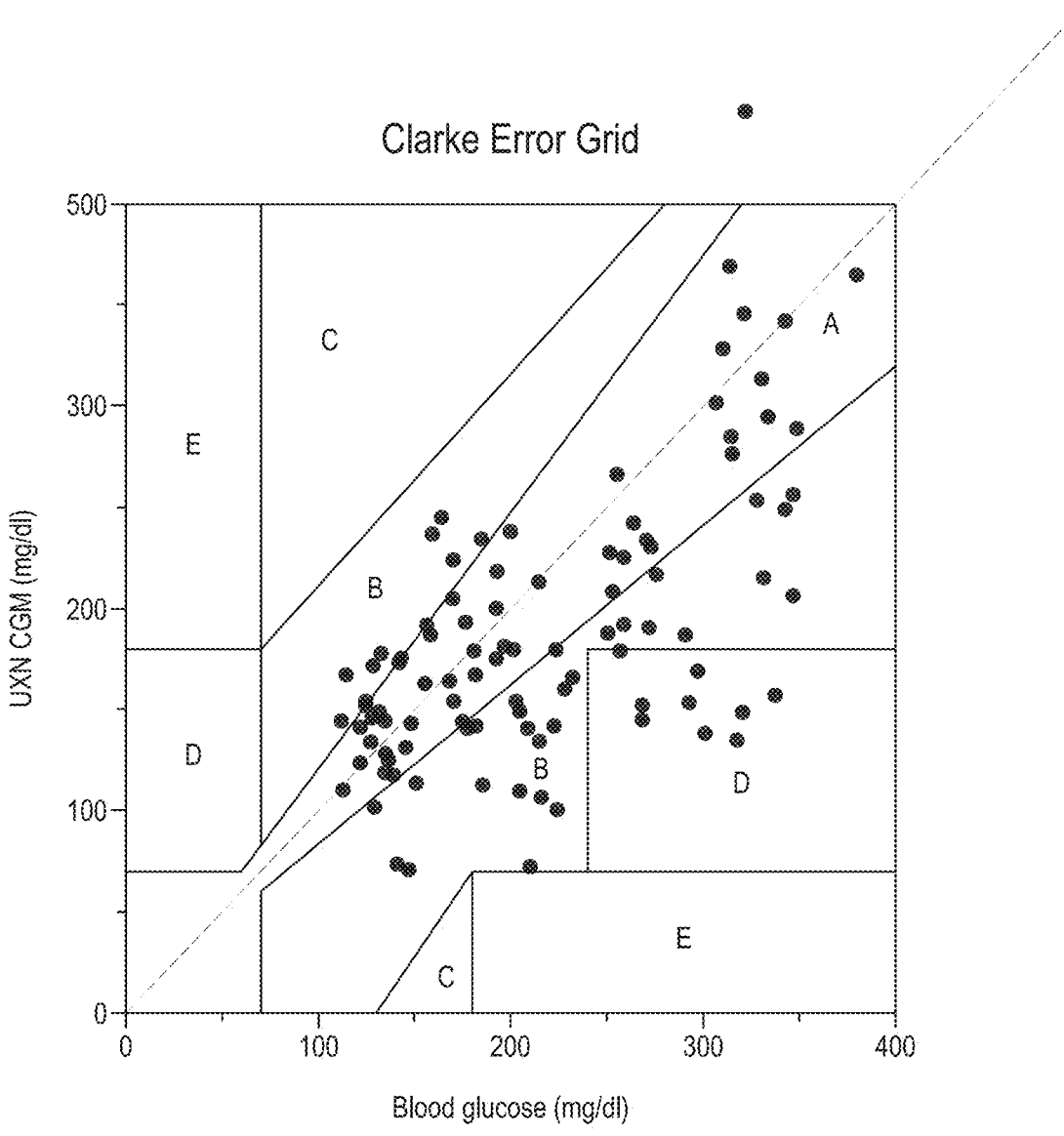
FIG. 47 is Clarke Error Grid for the non-enzymatic CGM electrode module according to an embodiment.

FIG. 47 is Clarke Error Grid for the non-enzymatic CGM electrode unit 701 prepared in Example 16.6 based on the measurements presented in the graph of FIG. 46. The reference sensor for this Clarke Error Grid Analysis is the Roche Accu-Chek® blood glucose meter. The grid has five regions. Region A includes values within 20% of the reference sensor; Region B includes values that are outside of Region A's 20% but would not lead to inappropriate treatment; Region C includes values that are potentially leading to unnecessary treatment; Region D includes values indicating a potentially dangerous failure to detect hypoglycemia or hyperglycemia; and Region E includes values that would confuse treatment of hypoglycemia for hyperglycemia and vice versa. As summarized in the table below the grid, the analysis shows that over 91% of the dots were in Region A and Region B.

Combination of Features

This disclosure provide a lot of discussions and information about many features relating to nanoporous structures and/or glucose sensing technologies. It is the intention of this disclosure to provide as many devices, systems and methods relating to those features. Two or more features disclosed above may be combined together to form a device, system or method to the extent they are combinable even if a particular combination is not presented in the present disclosure. Also, it is the intention of this disclosure to pursue claims directed to many of those features disclosed herein. Some of those features are presented in the form of claims in following section. Many claims are presented in dependent form by referring to one or more other claims. Applicant notes that some claims referring to multiple claims may encompass a combination of features that are in conflict with one another (hereinafter "improper combination"). However, Applicant recognizes that such claims may still encompass one or more combinations of features that do not have any conflicts with one another (hereinafter "proper combination"). By presenting claims that may encompass both proper and improper combinations, Applicant confirms its or inventor's possession of the proper combinations and intends to provide specific support for the proper combinations for later claiming of those proper combinations.

What is claimed is:

1. A glucose-sensing electrode comprising:
a substrate;
a glucose oxidation layer formed over the substrate and capable of oxidizing both glucose and maltose, wherein the glucose oxidation layer comprises numerous nanoparticles forming irregularly shaped bodies, wherein at least part of the irregularly shaped bodies are interconnected while forming unoccupied spaces inside of the glucose oxidation layer, and wherein the numerous nanoparticles are made of at least one selected from the group consisting of platinum (Pt), gold (Au), palladium (Pd), rhodium (Rh), titanium (Ti), ruthenium (Ru), tin (Sn), nickel (Ni), copper (Cu), indium (In), thallium (Tl), zirconium (Zr), iridium (Ir), and one or more oxides of each of the foregoing metals; and
means for blocking maltose that is configured for passing glucose therethrough while substantially blocking maltose from passing therethrough toward the glucose oxidation layer such that oxidation of glucose alone is substantially higher than oxidation of maltose alone in the glucose oxidation layer, wherein the means for blocking maltose is formed over the glucose oxidation layer.

2. The glucose-sensing electrode of claim 1, wherein at least part of the numerous nanoparticles has a generally oval or spherical shape with a length ranging between about 2 nm and about 5 nm,
wherein the unoccupied spaces inside of the glucose oxidation layer are irregularly shaped and connect with other unoccupied spaces inside the glucose oxidation layer.

3. The glucose-sensing electrode of claim 2, wherein, inside the irregularly shaped bodies, at least part of the nanoparticles are adjacent to each other without an intervening nanoparticle therebetween and apart from each other to define interparticular nanopores therebetween,
wherein at least part of the interparticular nanopores inside the irregularly shaped bodies are in a size ranging between about 0.5 nm and about 3 nm.

4. The glucose-sensing electrode of claim 2, wherein at least part of the irregularly shaped spaces are in a size ranging between about 100 nm and about 500 nm.

5. The glucose-sensing electrode of claim 1, wherein electric current caused by oxidation of glucose alone at the glucose oxidation layer is higher than 10 nA/mMcm$^2$ and oxidation of maltose alone at the glucose oxidation layer is lower than 5 nA/mMcm$^2$, when a bias voltage of 0.2-0.45 V is applied to the glucose oxidation layer relative to a reference electrode and when the glucose-sensing electrode contacts liquid containing glucose in a concentration of 4-20 mM and maltose in a concentration of 4-20 mM.

6. The glucose-sensing electrode of claim 1, wherein the glucose oxidation layer is capable of oxidizing glucose such that electric current caused by oxidation of glucose alone is higher than 10 nA/mMcm$^2$ when applying a bias voltage of 0.2-0.45 V and contacting liquid containing glucose in a concentration of 4-20 mM without the means for blocking maltose thereover,
wherein the glucose oxidation layer is further capable of oxidizing maltose such that electric current caused by oxidation of maltose alone is higher than 10 nA/mMcm$^2$ when applying a bias voltage of 0.2-0.45 V and when contacting liquid containing maltose in a concentration of 4-20 mM without the means for blocking maltose thereover.

7. The glucose-sensing electrode of claim 1, wherein the means for blocking maltose has a thickness between 10 nm and 40 nm.

8. The glucose-sensing electrode of claim 1, wherein the means for blocking maltose comprise poly-phenylenediamine (poly-PD) and has a thickness between 10 nm and 40 nm.

9. The glucose-sensing electrode of claim 1, further comprising an electrolyte ion-blocking layer formed over the means for blocking maltose and a biocompatibility layer formed over the electrolyte ion-blocking layer,
wherein the electrolyte ion-blocking layer comprises at least one selected from the group consisting of poly (methyl methacrylate) (PMMA), poly(hydroxyethyl methacrylate) (PHEMA), and poly(methyl methacrylate-co-ethylene glycol dimethacrylate) (PMMA-EG-PMMA),
wherein the electrolyte ion-blocking layer is configured to inhibit Na$^+$, K$^+$, Ca$^{2+}$, Cl$^-$, PO$_4^{3-}$ and CO$_3^{2-}$ contained in a liquid contacting the glucose-sensing electrode from diffusing toward the glucose oxidation layer such that a combined concentration of Na$^+$, K$^+$, Ca$^{2+}$, Cl$^-$, PO$_4^{3-}$ and CO$_3^{2-}$ has a profile with a substantial discontinuity between over the electrolyte ion-blocking layer and below the electrolyte ion-blocking layer.

10. The glucose-sensing electrode of claim 9, wherein when applying a bias voltage of 0.2-0.45 V thereto relative to a reference electrode, the glucose-sensing electrode is configured to cause oxidation of glucose in the glucose oxidation layer and configured to generate an electric current that is a sum of a glucose-oxidation current caused by the glucose oxidation alone and a background current caused by other electrochemical interactions of the liquid and the glucose-sensing electrode,
wherein, when the liquid contains glucose at a concentration of 4-20 mM (72-360 mg/dL), at steady state the glucose-oxidation current is at a level higher than 10 nA/mMcm$^2$.

11. The glucose-sensing electrode of claim 9, wherein the combined concentration below the electrolyte ion-blocking layer is greater than 0% and lower than about 10% of the combined concentration above the electrolyte ion-blocking layer.

12. The glucose-sensing electrode of claim 9, wherein the combined concentration below the electrolyte ion-blocking layer is greater than 0% and lower than about 5% of the combined concentration above the electrolyte ion-blocking layer.

13. The glucose-sensing electrode of claim 9, wherein the electrolyte ion-blocking layer comprises a porous and hydrophobic polymer layer that is configured to limit mobility of Na$^+$, K$^+$, Ca$^{2+}$, Cl$^-$, PO$_4^{3-}$ and CO$_3^{2-}$ therethrough while not limiting mobility of glucose molecules therethrough.

14. The glucose-sensing electrode of claim 1, wherein the glucose oxidation layer is capable of oxidizing both glucose and maltose without an enzyme specific to glucose or maltose in the glucose-sensing electrode.

15. The glucose-sensing electrode of claim 9, wherein the electrolyte ion-blocking layer is configured to facilitate conditioning of the glucose-sensing electrode such that conditioning of the glucose-sensing electrode is complete within 30 minutes from contacting a subject's bodily fluid with an application of a bias voltage of 0.2-0.45 V between the glucose-sensing electrode and a reference electrode.

16. An apparatus comprising:
a single integrated body comprising a subcutaneous portion and a terminal portion;
the subcutaneous portion comprising the glucose-sensing electrode of claim 1 and a reference electrode, each of which is exposed for contacting interstitial fluid of a first subject when the subcutaneous portion is subcutaneously inserted into the first subject's body; and
the terminal portion configured for coupling with a counterpart device and comprising a first terminal electrically connected to the glucose-sensing electrode and a second terminal electrically connected to the reference electrode.

17. An apparatus comprising:
a single integrated body comprising the glucose-sensing electrode of claim 1 and a reference electrode, the single integrated body further comprising a reservoir configured to at least temporarily hold a test fluid therein,
wherein the glucose-sensing electrode and the reference electrode are arranged in the single integrated body such that when the test fluid is held in the reservoir each of the glucose-sensing electrode and the reference electrode is configured to contact the test fluid.

18. A method of making the glucose-sensing electrode of claim 1, the method comprising:
providing the glucose oxidation layer capable of oxidizing both glucose and maltose; and
forming the means for blocking maltose over the glucose oxidation layer such that the means for blocking maltose has porosity configured for passing glucose therethrough while blocking maltose from passing therethrough toward the glucose oxidation layer such that oxidation of glucose alone is substantially higher than oxidation of maltose alone in the glucose oxidation layer and the oxidation of maltose does not interfere with determining a glucose level in a liquid containing glucose in a concentration of 4-20 mM and maltose in a concentration of 4-20 mM.

19. The method of claim 18, wherein forming the means for blocking maltose comprises performing electrochemical polymerization using the glucose oxidation layer as an electrode for the electrochemical polymerization.

20. The method of claim 18, wherein forming the means for blocking maltose comprises providing a polymer layer comprising poly-phenylenediamine (poly-PD) and adjusting the porosity of the polymer layer when electric current caused by oxidation of glucose alone in the glucose oxidation layer is expected to be lower than 10 $nA/mMcm^2$.

21. The method of claim 20, wherein adjusting the porosity comprises subjecting the polymer layer to at least one electric shock while the polymer layer contacts an acidic solution.

22. The method of claim 18, wherein forming the means for blocking maltose comprises polymerizing poly-phenylenediamine (poly-PD) from a liquid composition containing phenylenediamine at a concentration, wherein when the concentration is higher than a predetermined value, forming the means for blocking maltose further comprises adjusting the porosity of the means for blocking maltose.

23. The method of claim 22, wherein adjusting the porosity comprises subjecting the means for blocking maltose to at least one electric shock while the means for blocking maltose contacts an acidic solution.

24. The method of claim 18, wherein forming the means for blocking maltose comprises providing a polymer layer comprising poly-phenylenediamine (poly-PD) without further adjusting the porosity of the polymer layer when electric current caused by oxidation of glucose alone in the glucose oxidation layer is expected to be higher than 10 $nA/mMcm^2$.

25. The method of claim 18, wherein forming the means for blocking maltose comprises polymerizing poly-phenylenediamine (poly-PD) from a liquid composition containing phenylenediamine at a concentration, wherein when the concentration is lower than a predetermined value, the method does not comprise adjusting the porosity of the means for blocking maltose to form the means for blocking maltose.

26. The glucose-sensing electrode of claim 1, wherein the glucose oxidation layer is substantially free of a surfactant, wherein if any surfactant is contained in the glucose oxidation layer, the surfactant is in an amount smaller than 0.5 parts by weight with reference to 100 parts by weight of the nanoparticles.

27. The glucose-sensing electrode of claim 1, wherein the irregularly shaped bodies form a three-dimensional interconnected network of irregularly shaped bodies inside the glucose oxidation layer,
wherein the three-dimensional interconnected network of irregularly shaped bodies further comprises interparticular nanopores between adjacent nanoparticles in a size ranging between about 0.25 nm and about 4.5 nm.

28. The glucose-sensing electrode of claim 1, wherein the unoccupied spaces inside of the glucose oxidation layer are irregularly shaped and connect with other unoccupied spaces, which forms a three-dimensional interconnected network of irregularly shaped spaces inside the glucose oxidation layer,
wherein the unoccupied spaces forming the three-dimensional interconnected network of irregularly shaped spaces are individually in a size ranging between about 25 nm and about 700 nm.

29. The glucose-sensing electrode of claim 27, wherein the nanoparticles are primarily made of platinum (Pt) or gold (Au), wherein the interparticular nanopores are distributed inside the irregularly shaped bodies.

30. The glucose-sensing electrode of claim 28, wherein the unoccupied spaces of the three-dimensional interconnected network of irregularly shaped spaces are distributed substantially throughout in the glucose oxidation layer.

31. The glucose-sensing electrode of claim 1, wherein the means for blocking maltose comprises poly phenylenediamine (poly PD).

* * * * *